United States Patent [19]
Vermeulen et al.

[11] Patent Number: 5,872,104
[45] Date of Patent: Feb. 16, 1999

[54] COMBINATIONS AND METHODS FOR REDUCING ANTIMICROBIAL RESISTANCE

[75] Inventors: Nicolaas M. J. Vermeulen, Woodinville; Dennis E. Schwartz, Redmond, both of Wash.

[73] Assignee: Oridigm Corporation, Seattle, Wash.

[21] Appl. No.: 364,246

[22] Filed: Dec. 27, 1994

[51] Int. Cl.⁶ .................................................. A61K 31/70
[52] U.S. Cl. .............................. 514/29; 514/30; 514/35; 514/46
[58] Field of Search .............................. 514/29, 303, 30, 514/35, 46; 536/7.2

[56] References Cited

U.S. PATENT DOCUMENTS

| | | | |
|---|---|---|---|
| 2,870,138 | 1/1959 | Murray | 536/72 |
| 4,497,794 | 2/1985 | Klein et al. | 514/29 |
| 4,968,690 | 11/1990 | Marquez et al. | 514/303 |
| 5,132,291 | 7/1992 | Gruber | 574/43 |

FOREIGN PATENT DOCUMENTS

| | | |
|---|---|---|
| 0 052 705 | 6/1982 | Germany . |

OTHER PUBLICATIONS

Hasobe et al, "The Synergism of Nucleoside Antibiotics Combined with Guanine 7–N–Oxide Against a Rhabdovirus, Infectious Hematopoietic Necrosis Virus (IHNV)," The Journal of Antibiotics, vol. 39, No. 9, 1291–1297, 1986.

Kovacs, et al,"Potent Effect of Trimetrexate, a Lipid–Soluble Antigolate, on *Toxoplasma gondii*," The Journal of Infectious Diseases, vol. 155, No. 5, 1028–1032, May 1987.

Touze, J.E.,"Actualites Et Renouveau En Therapeutique Anti–Parasitaire," La Presse Medicale, vol. 23, No. 26, 1195–1198, Sep. 3–10, 1994.

*Primary Examiner*—Elli Peselev
*Attorney, Agent, or Firm*—Arnold, White & Durkee

[57] ABSTRACT

Disclosed are novel methods, combinations of agents and kits for use in killing, or inhibiting the growth of, microorganisms. Enhanced antimicrobial action is provided by using a methylation inhibitor, as exemplified by using an agent that inhibits methylation or maturation of bacterial RNA in combination with, e.g., a macrolide lincosamide streptogramin B (MLS) antibiotic. The methods and compositions described may be employed to reduce the resistance of susceptible microorganisms to antimicrobial agents and thus to treat animals or patients with infections.

132 Claims, 5 Drawing Sheets

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 15 base pairs (B) TYPE: nucleic acid
            (C) STRANDEDNESS: single
            (D) TOPOLOGY: linear (xi) SEQUENCE DESCRIPTION: SEQ ID NO:1:

AGGAGGAAAA ATATG                                                                15

(2) INFORMATION FOR SEQ ID NO:2:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (xi) SEQUENCE DESCRIPTION: SEQ ID NO:2:

TCCTCCTTTT TTATAC                                                               16

(2) INFORMATION FOR SEQ ID NO:3:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (xi) SEQUENCE DESCRIPTION: SEQ ID NO:3:

UCCUCCUUUU UUAUAC                                                               16

(2) INFORMATION FOR SEQ ID NO:4:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (xi) SEQUENCE DESCRIPTION: SEQ ID NO:4:

AGAGGGTTAT AATG                                                                 14

(2) INFORMATION FOR SEQ ID NO:5:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (xi) SEQUENCE DESCRIPTION: SEQ ID NO:5:

TCTCCCAACA CTAC                                                                 14

(2) INFORMATION FOR SEQ ID NO:6:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ix) FEATURE:
            (A) NAME/KEY: modified_base
            (B) LOCATION: (6, 10)
            (D) OTHER INFORMATION: /mod_base=OTHER
                / note= "N = A, G, C, or T"

(xi) SEQUENCE DESCRIPTION: SEQ ID NO:6:

GCGACNGGAN GGAAAGACCC C                                                         21

-continued ( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: (6, 10, 13-17)
        ( D ) OTHER INFORMATION: /mod_base=OTHER
            / note= "N = A, G, C, or T"

( x i ) SEQUENCE DESCRIPTION: SEQ ID NO:7:

CGCUGNCCUN CCNNNNNGGG G                                                  21

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: (6, 10)
        ( D ) OTHER INFORMATION: /mod_base=OTHER
            / note= "N = A, G, C, or T"

( x i ) SEQUENCE DESCRIPTION: SEQ ID NO:8:

GCGACNGGAN GGAAAGACCC C                                                  21

COMBINATIONS AND METHODS FOR REDUCING ANTIMICROBIAL RESISTANCE

BACKGROUND OF THE INVENTION

1. Field of the Invention

The present invention relates generally to the fields of bacteria, antimicrobials and antibiotics. More particularly, it provides novel methods, kits, and combinations of antimicrobial agents and inhibitors, for use in reducing the resistance of bacteria and other microorganisms to antimicrobial agents. In particular, the invention provides for enhanced bacterial killing using a macrolide, lincosamide and streptogramin B (MLS) antibiotic in combination with an agent that inhibits methylation, as exemplified by inhibiting methylation or maturation of bacterial RNA.

2. Description of the Related Art

The first antibiotics were used clinically in the 1940s and 195s, and their use has been increasing significantly since this period. Although an invaluable advance, antibiotic and antimicrobial therapy suffers from several problems, particularly when strains of various bacteria appear that are resistant to antibiotics. Interestingly, bacteria resistant to streptomycin were isolated about a year after this antibiotic was introduced (Waksman, 1945).

The development of antibiotic resistance is a serious and life-threatening event of worldwide importance. For example, strains of Staphylococcus are known that are immune to all antibiotics except one (Travis, 1994). Such bacteria often cause fatal hospital infections. Among other drug resistant organisms are: pneumococci that cause pneumonia and meningitis; Cryptosporidium and E. coli that cause diarrhea; and enterococci that cause blood-stream, surgical wound and urinary tract infections (Berkelman et. al., 1994).

Davies (1986) described seven basic biochemical mechanisms for naturally-occurring antibiotic resistance: (1) alteration (inactivation) of the antibiotic; (2) alteration of the target site; (3) blockage in the transport of the antibiotic; (4) by-pass of the antibiotic sensitive-step (replacement); (5) increase in the level of the inhibited enzyme (titration of drug); (6) sparing the antibiotic-sensitive step by endogenous or exogenous product; and (7) production of a metabolite that antagonizes action of inhibitor.

Certain bacteria become resistant to antibiotics by utilizing ribosomal mutations (Cunliffe, 1990), although some reports have stated that this type of resistance is of doubtful clinical significance (Spratt, 1994). Ribosomal mutations result in bacterial resistance to macrolide, lincosamide and streptogramin B (MLS) antibiotics, as has been observed in the resistance of various Staphylococcus, Streptococcus, Enterococcus, Bacillus and Mycoplasma strains to important antibiotics such as erythromycin (LeClercq & Courvalin, 1991).

The induction of erythromycin resistance generally leads to bacterial strains that express rRNA which does not bind to this type of antibiotic. Mainly, erythromycin resistance is due to the induction by macrolides of a methylase protein, which catalyzes the methylation of the binding site of erythromycin on the rRNA, thus preventing antibiotic binding. Despite intensive studies in this area, there remains few, if any, practical proposals as to how bacterial resistance to MLS antibiotics may be overcome.

SUMMARY OF THE INVENTION

The present invention seeks to overcome these and other drawbacks inherent in the prior art by providing new methods, combined compositions and kits, for use in reducing resistance to antimicrobials and antibiotics and for treating infections. The invention rests in the surprising use of one or more inhibitors of methylation in conjunction with an antimicrobial agent. The combination is used to impair the ability of a microorganism to methylate various substrates.

As the inventors contemplate that methylation, either at the DNA, RNA, protein or small molecule level, plays a role in all mechanisms of resistance of a microorganism to an antimicrobial agent, inhibition of methylation will be widely applicable to reducing resistance in any given microorganism or bacterium, and to treating a variety of diseases. For example, the organisms listed in Table 1 and Table 2 may be targeted using the antibiotics also listed in Table 1 and Table 2, amongst others, in combination with a methylation inhibitor. However, the invention is not limited to antibiotics and to bacteria alone, and is widely applicable to all microorganisms, including yeast and a variety of other pathogenic and even parasitic organisms.

The invention therefore encompasses methods, compositions and kits that include a methylation inhibitor capable of inhibiting any process listed in Table 1, as exemplified by the processes of antibiotic alteration, target site alteration and antibiotic transport. Also, as methylation inhibitors act to alter gene expression and protein synthesis, the invention includes methylation inhibitors that prevent the by-pass of antibiotic sensitive-steps, prevent an increase in the amount of an inhibited enzyme, prevent the production of an alternative endogenous or exogenous product, and prevent the production of a metabolite that antagonizes the action of inhibitor.

One particular example of the applicability of the invention is in providing methods and combinations for use in reducing the resistance of bacteria to macrolide, lincosamide, and streptogramin B (MLS) antibiotics, or in enhancing the sensitivity of susceptible strains to such antibiotics. In this case, the inhibitor will primarily inhibit methylation of bacterial rRNA, thus rendering the bacterium susceptible to antibiotic rRNA binding and allowing bacterial protein synthesis to be inhibited.

The various embodiments of the invention include methods, combined compositions and kits for reducing the resistance of a microorganism to an antimicrobial agent, as exemplified by reducing the antibiotic resistance of an MLS-susceptible bacterium to an MLS antibiotic. Also provided are methods, compositions and therapeutic kits for killing microorganisms, such as bacteria, and particularly, MLS-susceptible bacteria; and methods for treating infections and diseases caused by microorganisms, including treating MLS-susceptible bacterial infections and diseases. By way of example only, certain infections that may be treated using the invention are listed in Table 3.

To reduce the resistance of a microorganism to an antimicrobial agent, as exemplified by reducing the resistance of a bacterium to an antibiotic, or to kill a microorganism or bacterium, one would generally contact the microorganism or bacterium with an effective amount of the antibiotic or antimicrobial agent in combination with an amount of a second agent effective to inhibit methylation in the microorganism or bacterium. In terms of killing or reducing the resistance of an MLS-susceptible bacterium, one would contact the bacterium with an effective amount of an MLS antibiotic in combination with an amount of a second agent effective to inhibit RNA methylation, synthesis and/or maturation in the bacterium. The terms "microorganism" and "bacterium" are used for simplicity and it will be understood that the invention is suitable for use against a population of microorganisms, i.e., "bacteria".

The microorganism, e.g., bacterium, or population thereof, may be contacted either in vitro or in vivo. Contacting in vivo may be achieved by administering to an animal (including a human patient) that has, or is suspected to have a microbial or bacterial infection, a therapeutically effective amount of pharmacologically acceptable antimicrobial agent formulation in combination with a therapeutic amount of a pharmacologically acceptable formulation of a second agent effective to inhibit methylation, e.g., effective to inhibit RNA methylation. The invention may thus be employed to treat both systemic and localized microbial and bacterial infections by introducing the combination of agents into the general circulation or by applying the combination, e.g., topically to a specific site, such as a wound or burn, or to the eye, ear or other site of infection.

An "effective amount of an antimicrobial agent or antibiotic" means an amount, or dose, within the range normally given or prescribed. Such ranges are well established in routine clinical practice and will thus be known to those of skill in the art. Appropriate oral and parenteral doses and treatment regimens are further detailed herein in Table 4 and Table 5. Supplementary information relating specifically to MLS antibiotics is also given in Example I and in Tables 6 and 7, which particularly concern erythromycin, lincomycin, clarithromycin and azithromycin. As this invention provides for enhanced microbial and/or bacterial killing, it will be appreciated that effective amounts of an antimicrobial agent or antibiotic may be used that are lower than the standard doses previously recommended when the antimicrobial or antibiotic is combined with a methylation inhibitor.

The "second agents" for use in the invention are generally methylation inhibitors, and are also referred to herein as "inhibitors" and "modifiers". The second agent inhibitors should be used in amounts effective to inhibit methylation in a microorganism or bacterium, as exemplified by an amount effective to inhibit RNA methylation, synthesis and/or maturation in an MLS-susceptible bacterium. Suitable amounts effective to inhibit methylation will be known, or readily identifiable, to those of skill in the art. Effective inhibitory amounts are the amounts that have previously been shown in the scientific literature to inhibit methylation generally or to inhibit a specific methylation step. In addition to the present disclosure and the references specifically incorporated herein, there is considerable scientific literature concerning methylation inhibitors that may be utilized in light of the inventors' discovery that such compounds may be effectively combined with antibiotics and other antimicrobial agents.

Amounts effective to inhibit methylation may also be measured, rather than identified from the published literature. Most simply, this is achieved by determining the amount effective to increase microbial or bacterial killing when used in combination with an antimicrobial agent, i.e., by determining an amount effective to reduce antimicrobial resistance. The determinations of effective inhibitory amounts and therapeutic doses will be routine to those of skill in the art given the teachings of the present disclosure, including the detailed methodology and the effective amounts of various agents disclosed, e.g., in Table 8 and throughout the detailed examples.

Naturally, in confirming the optimal therapeutic dose, first animal studies and then clinical trials would be conducted, as is routinely practiced in the art. Animal studies are common in the art and are further described herein (Example II) and in publications such as Lorian (1991, pp. 746–786, incorporated herein by reference) and Cleeland & Squires (incorporated herein by reference, from within the Lorian text).

The $ID_{50}/IC_{50}$ ratio required for safe use of the proposed inhibitor-antimicrobial agent combinations will be assessed by determining the $ID_{50}$ (median lethal toxic dosage) and the $IC_{50}$ (median effective therapeutic dosage) in experimental animals. The optimal dose for human subjects is then defined by fine-tuning the range in clinical trials. In the case of $ID_{50}$, the inhibitor is usually administered to mice or rats (orally or intraperitoneal) at several doses (usually 4–5) in the lethal rage. The dose in mg/kg is plotted against % mortality and the dose at 50% represents the $ID_{50}$ (Klaassen, 1990). The $IC_{50}$ is determined in a similar fashion as described by Cleeland & Squires (1991).

In a clinical trial, the therapeutic dose would be determined by maximizing the benefit to the patient, whilst minimizing any side-effects or associated toxicities. Throughout the detailed examples, various therapeutic ranges are listed. Unless otherwise stated, these ranges refer to the amount of an agent to be administered orally.

In optimizing a therapeutic dose within the ranges disclosed herein, one would not use the upper limit of the range as the starting point in a clinical trial due to patient heterogeneity. Starting with a lower or mid-range dose level, and then increasing the dose will limit the possibility of eliciting a toxic or untoward reaction in any given patient or subset of patients. The presence of some side-effects or certain toxic reactions per se would not, of course, limit the utility of the invention, as it is well known that most beneficial drugs also produce a limited amount of undesirable effects in certain patients. Also, a variety of means are available to the skilled practitioner to counteract certain side-effects, such as using vitamin $B_{12}$ in association with $N_2O$ treatment (Ostreicher, 1994).

It is important to note that the invention does not require the identification of novel methylation inhibitors, but rather concerns the new and surprisingly effective use of various compounds, already known to have certain functional properties, in combination with antimicrobial agents or antibiotics. Neither does the invention require the identification of a precise molecular target, or of all targets, that a given methylation inhibitor may act upon.

It is not necessary therefore to determine methylation levels in a microorganism or bacterium to practice the invention, or to identify all the enzymes or other target molecules that are altered by the action of the inhibitor. All that is required is to use an antimicrobial agent in combination with an agent known to be, or suspected to be, capable of inhibiting methylation and to determine whether increased killing results.

Zak & Sande (1981) reported on the correlation between the in vitro and in vivo activity of a 1000 compounds that were randomly screened for antimicrobial activity. The important finding in this study is that negative in vitro data is particularly accurate, with the negative in vitro results showing more than a 99% correlation with negative in vivo activity. This is neaningful in the context of the present invention as one or more in vitro assays will be conducted prior to using any given combination in a clinical setting. Any negative result obtained in such an assay will thus be of value, allowing efforts to be more usefully directed.

Although the invention was developed, in part, from a consideration of various biochemical interactions and pathways, an understanding of the precise mechanism by which any given compound functions to reduce methylation in a microorganism, as measured by enhanced killing, is not relevant to practicing the invention. Therefore, effective methylation inhibitors, include those compounds that inhibit methylation both directly and indirectly. Many different enzymes and biochemical steps may be inhibited, or otherwise altered to the detriment of the microorganism or bacterium, as will be clear from the detailed examples.

This invention is considered to be particularly suitable for use in increasing the effectiveness of MLS antibiotics against, e.g., gram-positive staphylococcus, streptococcus, enterococcus and bacillus, gram-negative cocci and gram-negative aerobes.

Bacteria that may thus be attacked include those listed in Tables 6 and 7, and also, Staphylococcus spp., *S. sanguis, Corynebacterium diphtheria*, Bacteroides spp., *B. ovatus*, Clostridium spp., *C. difficile, B. subtilis*, Lactobacillus spp., Campylobacter spp., Propionibacterium spp., Mycoplasma spp., Fusobacterium, Corynebacterium, Veillonella, *S. fecalis, Nocardia farcinica, Actinobacillus actinomycetemcomitans*, Group A and B streptococci, *Bacillus stearothermophilus*, or *Pseudomonas aerugenosa*.

The second agent inhibitors may thus be effectively combined with one or more macrolide antibiotics, such as erythromycin, azithromycin, clarithromycin, roxithromycin, oleandomycin, spiramycin, josamycin, miocamycin, midecamycin, rosaramycin, troleandomycin, flurithromycin, rokitamycin or dirithromycin; one or more lincosamide antibiotics, such as lincomycin, clindamycin, celesticetin; or one or more streptogramin B antibiotics, such as pristinamycin or virginiamycin. Erythromycin, azithromycin, clarithromycin, lincomycin and clindamycin are currently the most preferred.

Suitable inhibitory second agents include those that inhibit RNA methyltransferase enzymes, as described in Example IV. These agents are exemplified by S-adenosylhomocysteine (SAH) and analogues; homocysteine; adenine derivatives, such as adenine phosphate, adenine sulfate, adenine-$N^1$-oxide, 6-methyladenine, 6-mercaptoadenine, with dimethylallyladenine and isopentenyladenosine being particularly preferred; and SAM analogues and derivatives, such as methyl, ethyl, n-propyl, allyl, n-butyl, n-pentyl, n-octyl and 6-amino-1-hexyl nitrogen analogues of SAM, and S-inosyl-L-methionine, S-adenosyl-(5')-3-methylthio-propylamine and 5'-methylthioadenosine.

Further inhibitors of RNA methyltransferases include sinefungin and analogues and metabolites, such as A9145C, 5'-S-methylthioadenosine and cyclosinefungin; nicotinamide and analogues, such as methylnicotinamide; and polyinosinate. Specific examples of suitable compounds include S-$N^6$-methyladenosylhomocysteine; S-aristeromycinyl-L-homocysteine and analogues thereof, such as 3-deazaaristeromycinyl-D-homocysteine; 5'-deoxy-5'-S-isobutyl-adenosine (SIBA) and ISOSIBA; S-tubercidinylhomocysteine (STH) and analogues; MTA and xylosyladenine.

It will be recognized that many compounds will exert multiple effects on a microorganism or bacterial cell. For example, SAH analogues and tubercidin act at various points in methylation pathways. The division of the useful agents into certain groups is thus not intended to be an exact and non-overlapping scientific division. Rather such information is set forth to assist those in the art with understanding certain scientific data that were considered by the inventors.

Second agents that inhibit S-adenosylhomocysteine (SAH) hydrolase (SAHH) are also useful, as described in Example V, and exemplified by adenosine and analogues. Useful adenosine analogues include the first generation agents 9(S)-(2,3-dihydroxypropyl)adenine [(S)-DHPA], D-eritadine, (R,S)-3-adenine-9-yl-2-hydroxypropanocic acid [(R,S)-AHPA], adenosine (Ado) dialdehyde, 3-deazaadenosine ($c^3$-Ado), aristeromycin (Ari) and neplanocin A (NPA or NpcA).

Second generation analogues are more preferred and include dihydroxycyclopentenyladenine (DHCeA), dihydroxycyclopentenyl-3-deazaadenine ($c^3$-DHCeA), dihydroxycyclopentanyladenine (DHCaA), dihydroxycyclopentanyl-3-deazaadenine ($c^3$-DHCaA), 3-deazaneplanocin A ($c^3$-NpcA), 3-deazaaristeromycin ($c^3$-Ari), carbocyclic-3-deazaadenosine (C-$c^3$Ado), 6'-C-methylneplanocin A, 2'-deoxyadenosine and tubercidin. Other useful analogues in this category include ribavirin, pyraazofurin, 2'-deoxy-2'-chloroadenosine, isopentenyladenosine and methylthioadenosine (MTA).

Other useful SAH hydrolase inhibitors include 9-β-arabinofuranosyladenine (Ara-A, vidarabine) and 2'-Deoxyadenosine, of which Ara-A is already approved by the FDA. Aristeromycin analogues, including aristeromycin itself and N-methylaristeromycin, 8-azaaristeromycin and 3-deazaaristeromycin, and their dialdehyde and diol derivatives are also effective inhibitors, as are (±)-5-Noraristeromycin and its 2,6-diamino-analogue. Further useful aristeromycinyl analogues with reduced toxicity include 2'-deoxy-, 3'-deoxy-, 3'-amino-3'-deoxy-, 3'-amino-3'-deoxyarabinofuranosyl, 6'-hydroxy, 6'-mercapto, 8'-bromo, 8-hydroxyaristeromycin, aristeromycin-3'-cyclic phosphate and aristeromycin-6'-cyclic phosphate, all of which may be used in the present invention.

Certain structural analogues of SAH with modification in the amino acid, base or sugar portion of the molecule may be used to inhibit SAH hydrolase. Useful analogues of this class include 2-fluoro-S-adenosylhomocysteine (2-FSAH), S-Adenosyl-L-homocysteine sulfoxide, S-Adenosyl-L-homocysteine sulfone, S-aristeromycinyl-L-homocysteine, 5'-S-(3-carboxyl-4-nitrophenyl) thioadenosine and 5'-S-(methyl)-5'-S-(butyl) thioadenosine.

S-adenosylmethionine (SAM) synthetase (SAMS) is another target that may be inhibited, e.g., by using second agents such as cycloleucine (1-aminocyclopentane-1-carboxylic acid) and analogues; mono, bi- and tri-cyclic amino acid structural and conformational analogues of L-methionine; and ATP/methionine analogues, such as AMPNPP. Particular examples of cycloleucine and methionine analogues include 1-aminocyclobutanecarboxylic acid, 1-aminocyclohexanecarboxylic acid, L-2-amino-4-hexanoic acid, (Z)-L-2-amino-5-chloro-trans-4-hexanoic acid, L-ethionine, seleno-DL-ethionine, the (1R,2R,4S) isomer of 2-aminonorbornane-2-carboxylic acid, the (1R,2R,4S) isomer of 2-amino-5,6-exo-trimethylenenorbornane-2-carboxylic acid, 3-aminobicyclo[3.2.0]heptane-3-carboxylic acid and, preferably, (+)-2-aminobicyclo[2.1.1]hexane-2-carboxylic acid.

Further suitable inhibitors of (SAM) synthetase include L-2-amino-4-methoxy-cis-but-3-enoic acid (L-cis-AMB), L-2-amino-4-methylthio-cis-but-3-enoic acid (L-cisAMTB) and covalent methionine-ATP adducts such as 5'(R)-(C)-[(L-homocysteine-S-yl) methyl]adenosine 5'-(β,γ)-imidotriphosphate.

Agents that inhibit, by any mechanism, the synthesis of glutathione form another group of SAMS inhibitors. Inhibitors of glutathione synthetase are examples of this class, and include buthionine sulfoximine, 7,8-dihydrofolate, α-aminomethylglutarate, SAPH-3 and diethyl maleate. Methotrexate and trimethoprim, that inhibit DHFR, also act to reduce glutathione synthetase activity.

Other agents that may be employed are methionine synthetase (MS) and homocysteine transmethylase inhibitors, such as nitrous oxide ($N_2O$), as commonly employed in dentistry. Adenosine deaminase (ADA), and even adenosine kinase, inhibitors may also be used. ADA inhibitors include, e.g., coformycin, deoxycoformycin (pentostatin) and isomers, 1,6-dihydro-6-hydroxy-methylpurine nucleoside, erythro-9-(2-hydroxy-3-nonyl)adenine, 6-methylaminopurine riboside and 2'-3'-isopropylideneadenosine. Compounds that inhibit the enzyme after ADA, purine nucleoside phosphorylase, are also contemplated for use as they will lead to a build up of inosine.

Dihydrofolate reductase (DHFR) inhibitors, such as the clinically used drugs methotrexate (MTX), aminopterin and trimethoprim, and 4,6-diamino-2,2-dimethyl-s-triazine and 2,4-diamino-5-(3,4-dichlorophenyl)pyrimidine analogues (e.g., NSC 127755 and 139105) may be used, as may inhibitors of dihydropteroate synthetase, such as sulfanilamide, sulfadiazine, sulfamethoxazole, sulfisoxazole and sulfacetamide that also inhibit DHFR.

$^5$N-Methyltetrahydrofolate ($5$—$CH_3$—$FH_4$) is used as a methyl donor in the last step of methionine synthesis from homocysteine in many bacterial reactions. Inhibition of $5$—$CH_3$—$FH_4$ synthesis will thus cause a reduction in SAM synthesis. The inventors therefore contemplate that agents that inhibit the production of any of the biosynthetic precursors of $5$—$CH_3$—$FH_4$, or those that otherwise exert a negative influence on any of the $5$—$CH_3$—$FH_4$ biosynthetic steps, will also be useful in the present invention. Exemplary inhibitors are those listed above such as MTX, NSC 127755, sulfonamides, and the like.

Compounds that inhibit polyamine synthesis are also useful. These include compounds such as a-methylornithine, 1,3-diaminopropan-2-ol, difluoromethylornithine (DFMO) and difluoromethylarginine (DFMA). Also included are those compounds that inhibit specific enzyme targets, such as ornithine decarboxylase (ODC), arginine decarboxylase (ADC) and SAM Decarboxylase (SAM-DC). Inhibitors of SAM-DC include AMA, MHZPA, MAOEA, AbeAdo (MDL 73811), AdoMac, MGBG, CGP-39'937 and CGP-33'829, as shown in Example X; inhibitors of ODC include eflornithine and other compounds described by McCann & Pegg (1992) and Pegg & McCann (1992); and inhibitors arginine decarboxylase include, by way of example, DL-α-(difluoromethyl) arginine.

Compounds such as 5-azacitidine, cordycepin (3'-deoxyadenosine), toyocamycin and analogues, that inhibit RNA maturation, are also contemplated for use. Antisense oligonucleotides may also be employed to inhibit the induction of bacterial methylase synthetase or as decoys that prevent the methylation of rRNA. Antisense oligonucleotides may be advantageously delivered using liposomes.

In the treatment of animals or human patients, there are various appropriate formulations and treatment regimens that may be used. For example, the antimicrobial compound (s) and second agent(s) may be administered to an animal simultaneously, e.g., in the form of a single composition that includes the microbial/antibiotic and second agent, or by using at least two distinct compositions. The antimicrobial agent could also be administered to the animal prior to the second agent, although it is currently more preferred to give the second agent inhibitor prior to the antimicrobial agent.

The invention also provides novel compositions that contain a combination of antimicrobials and second agents, not previously proposed for combined use, dispersed in a pharmacologically acceptable formulation. The antimicrobial agents and inhibitory second agents may be formulated and administered in any pharmacologically acceptable vehicle, such as parenteral, topical, liposomal, nasal or ophthalmic preparations, with formulations designed for oral administration being currently preferred due to their ease of use.

Multiple combinations may also be used, such as more than one antimicrobial agent used with one second agent or more than one second agent used with a given antimicrobial. Different classes of antimicrobial agents and second agents may be combined, naturally following the general guidelines known in the art regarding drug interactions. Preferred combinations will be those in which inhibitors from different classes are used. Typically, between one and about five distinct antimicrobial agents are contemplated for use along with between one and about ten distinct second agents. Combinations including at least one MLS antibiotic are currently preferred as there appears to be a particular nee d in the art for an improvement in MLS antibiotic therapy.

Currently, one preferred group of inhibitory agents includes DHPA, D-eritadine, (R,S)-AHPA, adenosine dialdehyde, $c^3$-Ado, aristeromycin and neplanocin A; with DHCeA, $c^3$-DHCeA, DHCaA, $c^3$-DHCaA, $c^3$-NpcA, $c^3$-Ari, C-$c^3$Ado, 6'-C-methylneplanocin A, tubercidin and Ara-A being more preferred. Further preferred compounds are polyinosinate, L-cis-AMB, L-cis-AMTB, buthionine sulfoximine, methotrexate, trimethoprim, $N_2O$, NSC 127755, NSC 139105, DFMO, DFMA, coformycin, deoxycoformycin and sulfonamides.

Further embodiments of the invention include therapeutic kits that comprise, in suitable container means, a pharmaceutical formulation of at least one antimicrobial agent and a pharmaceutical formulation of at least one microbial methylation inhibitor. The antibiotics and inhibitory second agents may be contained within a single container means, or a plurality of distinct containers may be employed.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

Figure 1A:
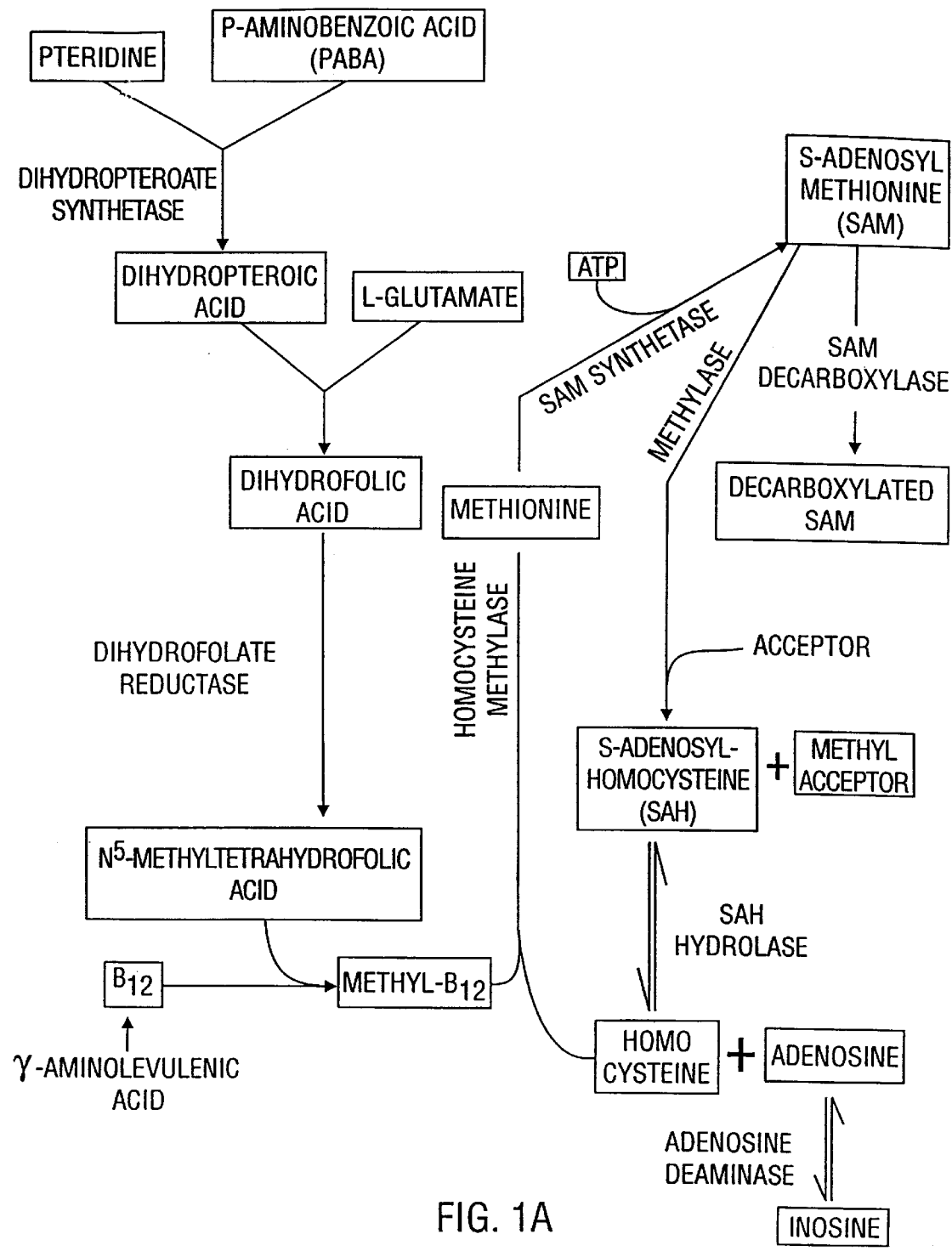
FIG. 1A and FIG. 1B. Intermediates in the SAM/SAH cycle. Effective methylation requires the concerted action of a number of enzymes: methyltransferases, SAH hydrolase, dihydropteroate synthetase, dihydrofolate reductase, SAM synthetase, methionine synthetase, homocysteine transmethylase, ornithine decarboxylase, arginine decarboxylase and adenosine deaminase.

Antimicrobial combinations are well known and are most frequently used to provide broad-spectrum empirical coverage in the treatment of patients who are seriously ill and who may be septicemic. Combinations are also chosen because an identified pathogen is resistant to inhibition and/or killing by conventional doses of a single antibiotic, but in contrast is susceptible to the combination (Eliopoulos & Moellering, 1991).

Lorian (1991) indicated that there are generally four accepted mechanisms of antibacterial synergism, namely, (1) serial or sequential inhibition of a common biochemical pathway (e.g. trimethoprim-sulfamethoxazole); (2) inhibition of protective bacterial enzyme (clavulanic acid plus a B-lactamase-susceptible penicillin); (3) combination of cell wall-active agents (e.g. amdincillin and ampicillin); and (4) use of cell wall-active agents to enhance the uptake of other antimicrobials (e.g. penicillin and streptomycin). The present invention provides a novel synergistic option for antimicrobial treatment.

A. Antibiotic Resistance

Seven basic biochemical mechanisms for naturally-occurring antibiotic resistance have been described (Davies, 1986), namely alteration of the antibiotic; alteration of the target site; block in the transport of the antibiotic; by-pass of the antibiotic sensitive-step; increasing the level of the inhibited enzyme; the cell is spared the antibiotic-sensitive step by endogenous or exogenous product; and the production of a metabolite that antagonizes action of inhibitor. The same general concepts also apply to microorganisms other than bacteria.

Antibiotic and antimicrobial resistance can be spread vertically and horizontally by plasmids and transposons. The inventors propose that methylation reactions play an active role in both plasmids and transposons, and that methylation inhibitors will modulate general antibiotic resistance. Butler & Gotschlich (1991) indicated that high-frequency mobilization of broad-host-range plasmids into *Neisseria gonorrhoea* requires methylation in the donor. Additionally, they concluded that methylation/restriction systems was a major barrier against deficient conjugal transfer between *N. gonorrhoea* and heterologous hosts.

This invention therefore encompasses methods to reduce antimicrobial resistance, caused by any of the seven mechanisms described above, using a combination of the antimicrobial agent and one or more inhibitor(s) that modify or influence methylation and the associated processes. A list of antibiotics that have developed antibiotic resistance by one or more of these mechanisms is listed in Table 1 (taken from Lorian, 1991), all of which are intended to be combined with a methylation inhibitor, as described herein, thereby achieving enhanced microbial killing.

Table 2 (taken from Reese & Betts, 1993; Med. Let., 1992), lists the antibiotics generally preferred for use against a given pathogenic bacterium. It is contemplated that the effectiveness of all the antibiotics listed in Table 2 will be increased upon combination with a methylation inhibitor. Table 3 (also taken from Reese & Betts, 1993), itemizes the common pathogenic bacteria that are implicated in focal infections. The present invention is thus contemplated for use against all such infections.

TABLE 1

MECHANISMS OF RESISTANCE TO ANTIMICROBIAL AGENTS

| Antimicrobial Agent | Mechanisms Causing Resistance | Examples of Organisms |
| --- | --- | --- |
| Aminoglycosides | Modifying enzymes: acetyltransferases, adenylyl-transferases (nucleotidyl-transferases), phosphotransferases | Enterobacteriaceae, P. aeruginosa, S. aureus, E. faecalis |
| | Ribosomal resistance (streptomycin, spectinomycin) | E. faecalis, Enterobacteriaceae, M. tuberculosis, P. aeruginosa |
| | Inadequate drug transport | E. faecalis, P. aeruginosa, anaerobes |
| β-Lactams | Enzymatic inactivation | S. aureus, E. faecalis, Enterobacteriaceae, P. aeruginosa, Neisseria spp., H. influenzae |
| | Low affinity PBPs | S. pneumoniae, N. gonorrhoeae, S. aureus, P. aeruginosa |
| | Lack of penetration through outer membrane | P. aeruginosa, Enterobacteriaceae |
| Chloramphenicol | Acetylation | Enterobacteriaceae, S. aureus, streptococci, Bacteroides uniformis |
| | Lack of penetration | P. aeruginosa |
| Clindamycin, erythromycin, lincomycin | Ribosomal resistance due to methylation of rRNA | Streptococci, E. faecalis, Enterobacteriaceae |
| | Inactivation by esterase | Enterobacteriaceae |
| | Decreased penetration | S. hominis |
| Fluoroquinolones | Decreased uptake | Enterobacteriaceae, P. aeruginosa, staphylococci |
| | Altered target site (DNA gyrase) | Enterobacteriaceae, P. aeruginosa |
| Lincomycin | Inactivation | S. aureus |
| Sulfonamides | Synthesis of an altered or | Enterobacteriaceae, |

TABLE 1-continued

MECHANISMS OF RESISTANCE TO ANTIMICROBIAL AGENTS

| Antimicrobial Agent | Mechanisms Causing Resistance | Examples of Organisms |
| --- | --- | --- |
| | alternative target site (dihydropteroate synthetase) | Neisseria spp., P. aeruginosa |
| | Lack of penetration | Anaerobes |
| | Overproduction of PABA | Neisseria, S. aureus |
| Tetracycline | Drug efflux | Enterobacteriaceae, staphylococci, streptococci |
| | Protection of ribosome from tetracycline | Streptococci, E. faecalis, Neisseria spp., Mycoplasma spp. |
| | Inactivation | Cryptic gene found in B. fragilis, expressed resistance in E. coli |
| Trimethoprim | Synthesis of an altered or alternative target site (dihydrofolate reductase) | Enterobacteriaceae, V. cholerae, staphylococci |
| | Lack of penetration | P. aeruginosa |
| | Ability to use alternative pathway | Enterococci |
| | Overproduction of dihydrofolate reductase | H. influenzae |
| Vancomycin | ? | Pediococci, Leuconostoc spp. (intrinsic) |
| | ?Blocking of target site | Enterococci (acquired) |

TABLE 2

ANTIBIOTICS OF CHOICE FOR COMMON PATHOGENS

| Pathogen | Antibiotic of First Choice[a] | Alternative Agent[a] |
| --- | --- | --- |
| Gram-positive *cocci* | | |
| *Staphylococcus aureus* or *S. epidermidis* | | |
| Non-penicillinase-producing | Penicillin | A first-generation cephalosporin, vancomycin, imipenem, or clindamycin; a fluoroquinolone[b] |
| Penicillinase-producing | Penicillinase-resistant penicillin (e.g., oxacillin or nafcillin) | A first-generation cephalosporin, vancomycin, clindamycin, imipenem, amoxicillin-clavulanic acid, ticarcillin-clavulanic acid, ampicillin-sulbactam; a fluoroquinolone[b] |
| Methicillin-resistant | Vancomycin with or without gentamicin and/or rifampin | TMP-SMZ, minocycline |
| Streptococci | | |
| Group A, C, G | Penicillin | A cephalosporin[a], vancomycin, erythromycin; clarithromycin; azithromycin; clindamycin |
| Group B | Penicillin (or ampicillin) | A cephalosporin[a], vancomycin, or erythromycin |
| Enterococcus | | |
| Endocarditis or other serious infection | Penicillin (or ampicillin) with gentamicin | Vancomycin with gentamicin |
| Uncomplicated urinary tract infection | Ampicillin or amoxicillin | A fluoroquinolone, nitrofurantoin |
| Viridans group | Penicillin G (with or without gentamicin) | A cephalosporin[a], vancomycin |
| *S. bovis* | Penicillin G | A cephalosporin[a], vancomycin |
| *S. pneumoniae* | Penicillin G | A cephalosporin[a], erythromycin, chloramphenicol, vancomycin |
| Gram-negative *cocci* | | |
| *Neisseria gonorrhoeae* | Ceftriaxone | Spectinomycin, a fluoroquinolone, cefoxitin, cefixime, cefotaxime (see Appendix E) |

TABLE 2-continued

ANTIBIOTICS OF CHOICE FOR COMMON PATHOGENS

| Pathogen | Antibiotic of First Choice[a] | Alternative Agent[a] |
|---|---|---|
| *N. meningitidis* | Penicillin G | Third-generation cephalosporin, chloramphenicol |
| Moraxella (Branhamella) catarrhalis | TMP-SMZ | Amoxicillin-clavulanic acid; an erythromycin; clarithromycin azithromycin, cefuroxime, cefixime, third-generation cephalosporin, tetracycline |
| Gram-positive *bacilli* | | |
| *Clostridium perfringens* (and *Clostridium sp.*) | Penicillin G | Chloramphenicol, metronidazole, or clindamycin |
| *Listeria monocytogenes* | Ampicillin with or without gentamicin | TMP-SMZ |
| Gram-negative *bacilli* | | |
| Acinetobacter | Imipenem | Tobramycin, gentamicin, or amikacin, usually with ticarcillin or piperacillin (or similar agent); TMP-SMZ |
| *Aeromonas hydrophila* | TMP-SMZ | Gentamicin, tobramycin; imipenem; a fluoroquinolone |
| Bacteroides | | |
| *Bacteroides sp.* (oropharyngeal) | Penicillin G | Clindamycin, cefoxitin, metronidazole, chloramphenicol, cefotetan, ampicillin-sulbactam |
| *B. fragilis* strains (gastrointestinal strains) | Metronidazole | Clindamycin; ampicillin-sulbactam; imipenem; cefoxitin[c]; cefotetan[c]; ticarcillin-clavulanic acid; piperacillin[c]; chloramphenicol; cefmetazole[c] |
| *Campylobacter fetus, jejuni* | A fluoroquinolone (adults) or an erythromycin | A tetracycline, gentamicin |
| *Enterobacter sp.* | Imipenem | An aminoglycoside and piperacillin or ticarcillin or mezlocillin; a third-generation cephalosporin[d]; TMP-SMZ; aztreonam; a fluoroquinolone |
| *Escherichia coli* | | |
| Uncomplicated urinary tract infection | TMP-SMZ | A cephalosporin or a fluoroquinolone |
| Recurrent or systemic infection | A cephalosporin[c] | Ampicillin with or without an aminoglycoside, TMP-SMZ, oral fluoroquinolones useful in recurrent infections, ampicillin-sulbactam, ticarcillin-clavulanic acid, aztreonam |
| *Haemophilus influenzae* | | |
| (coccobacillary) Life-threatening infections | Cefotaxime or ceftriaxone | Chloramphenicol; cefuroxime for pneumonia) |
| Upper respiratory infections and bronchitis | TMP-SMZ | Ampicillin or amoxicillin; cefuroxime; a sulfonamide with or without an erythromycin; cefuroxime-axetil; third-generation cephalosporin, amoxicillin-clavulanic acid, cefaclor, tetracycline; clarithromycin; azithromycin |
| *Klebsiella pneumoniae* | A cephalosporin[c] | An aminoglycoside, imipenem, TMP-SMZ, ticarcillin-clavulanic acid, ampicillin-sulbactam, aztreonam, a fluoroquinolone; amoxicillin-clavulanic acid |
| *Legionella spp.* | Erythromycin with rifampin | TMP-SMZ; clarithromycin; azithromycin; ciprofloxacin |
| *Pasteurella multocida* | Penicillin G | Tetracycline, cefuroxime, amoxicillin-clavulanic acid, ampicillin-sulbactam |
| *Proteus sp.* | Cefotaxime, ceftizoxime, or ceftriaxone[f] | An aminoglycoside; ticarcillin or piperacillin or mezlocillin; TMP-SMZ; amoxicillin-clavulanic acid; ticarcillin-clavulanic acid, |

TABLE 2-continued

ANTIBIOTICS OF CHOICE FOR COMMON PATHOGENS

| Pathogen | Antibiotic of First Choice[a] | Alternative Agent[a] |
| --- | --- | --- |
| | | ampicillin-sulbactam; a fluoroquinolone; aztreonam; imipenem |
| *Providencia stuartii* | Cefotaxime, ceftizoxime, or ceftriaxone[f] | Imipenem; an aminoglycoside often combined with ticarcillin or piperacillin or similar agent; ticarcillin-clavulanic acid; TMP-SMZ, a fluoroquinolone; aztreonam |
| *Pseudomonas aeruginosa* (nonurinary tract infection) | Gentamicin or tobramycin or amikacin (combined with ticarcillin, piperacillin, etc. for serious infections) | An aminoglycoside and ceftazidime; imipenem, or aztreonam plus an aminoglycoside; ciprofloxacin |
| (urinary tract infections) | Ciprofloxacin | Carbenicillin; ticarcillin, piperacillin, or mezlocillin; ceftazidime; imipenem; aztreonam; an aminoglycoside |
| *Pseudomonas cepacia* | TMP-SMZ | Ceftazidime, chloramphenicol |
| *Salmonella typhi* | Ceftriaxone | Ampicillin, amoxicillin, TMP-SMZ, chloramphenicol; a fluoroquinolone |
| Other species | Cefotaxime or ceftriaxone | Ampicillin or amoxicillin, TMP-SMZ, chloramphenicol; a fluoroquinolone |
| Serratia | Cefotaxime, ceftizoxime, or ceftriaxone[f] | Gentamicin or amikacin; imipenem; TMP-SMZ; ticarcillin, piperacillin, or mezlocillin; aztreonam; a fluoroquinolone |
| Shigella | A fluoroquinolone | TMP-SMZ; ceftriaxone; ampicillin |
| *Vibrio cholerae* (chlorea) | A tetracycline | TMP-SMZ; a fluoroquinolone |
| *Vibrio vulnificus* | A tetracycline | Cefotaxime |
| Xanthomonas (Pseudomonas) maltophilia | TMP-SMZ | Minocycline, ceftazidime, a fluoroquinolone |
| *Yersinia enterocolitica* | TMP-SMZ | A fluoroquinolone; an aminoglycoside; cefotaxime or ceftizoxime |
| *Yersinia pestis* (plague) | Streptomycin | A tetracycline; chloramphenicol; gentamicin |

Key: TMP-SMZ = trimethoprim-sulfamethoxazole.
[a]Choice presumes susceptibility studies indicate that the pathogen is susceptible to the agent.
[b]The experience with fluoroquinolone use in *staphylococcal* infections is relatively limited. The fluoroquinolones should be used only in adults.
[c]Up to 15–20% of strains may be resistant.
[d]*Enterobacter spp.* may develop resistance to the cephalosporins.
[e]Specific choice will depend on susceptibility studies. Third-generation cephalosporins may be exquisitely active against many gram-negative *bacilli* (e.g., *E. coli, Klebsiella sp.*). In some geographic areas, 20–25% of community-acquired *E. coli* infections may be resistant to ampicillin (amoxicillin).
[f]In severely ill patients, this is often combined with an aminoglycoside while awaiting susceptibility data.

TABLE 3

COMMON PATHOGENS IN FOCAL INFECTIONS

| Presumed location of infection | Common pathogens | Gram stain characteristics of exudate-if available |
| --- | --- | --- |
| Urinary tract infections | Community-acquired: *Escherichia coli* | GNB |
| | Recurrent or nosocomial: *E. coli*: Klebsiella, Proteus, *Pseudomonas sp.* Enterococci | GNB |
| | | GPC |
| Intravenous catheter phlebitis and/or sepsis | | |
| Peripheral catheter | *Staphylococcus aureus* or *S. epidermidis* | GPC |
| | Klebsiella, Enterobacter, *Pseudomonas sp.* | GNB |
| Hyperalimentation line | *Candida sp., S. aureus, S. epidermidis*, enterococci | Budding yeast; GPC |
| | Klebsiella, *Enterobacter sp.*, etc. | GNB |
| Arteriovenous shunt | *S. aureus, S. epidermidis* | GPC |

TABLE 3-continued

COMMON PATHOGENS IN FOCAL INFECTIONS

| Presumed location of infection | Common pathogens | Gram stain characteristics of exudate-if available |
|---|---|---|
| Septic bursitis | S. aureus | GPC |
| Biliary tract | E. coli, Klebsiella sp., and enterococci; Bacteroides fragilis (in elderly patients), Clostridia sp. | |
| Intra-abdominal abscess, peritonitis, or large bowel perforation; diverticulitis[a] | E. coli | GNB |
| | B. fragilis | GNB (thin, irregularly stained) |
| | Klebsiella sp. | GNB |
| | (Enterococci) | GPC |
| Burn wounds | Early: S. aureus, streptococci Later: gram-negative bacilli, fungi | |
| Cellulitis, wound and soft tissue infections | S. aureus | GPC |
| | Streptococci | GPC |
| | Clostridium sp. | GPB |
| Meningitis | See Appendix C | |
| Pneumonia | See Appendix D | |
| Pelvic abscess, postabortal or postpartal | Anaerobic streptococci | GPC |
| | B. fragilis | GNB (thin, irregularly stained) |
| | Clostridium sp. | GPB |
| | E. coli | GNB |
| | Enterococci | GPC |
| Septic arthritis | S. aureus | GPC |
| | Haemophilus influenzae (in children younger than 6 yr) | GNC |
| | Group B streptococci (in neonates) | GPC |
| | Gram-negative organisms[b] | GNB |
| Acute osteomyelitis | S. aureus | GPC |
| | H. influenzae (in children younger than 6 yr) | GNC |
| | Group B streptococci (in neonates) | GPC |
| | Gram-negative organisms[b] | GNB |

Key: GNB = gram negative *bacilli;* GPC = gram-positive *cocci;* GPB = gram-positive *bacilli;* GNC = gram-negative *coccobacilli.*
[a]The precise role of *enterococci* in intra-abdominal infections is unclear. In mild to moderate infections, it may not be necessary to provide antibiotic activity against *enterococci.*
[b]In high-risk patients (e.g., immunocompromised, elderly, IV drug abusers, diabetics, debilitated patients).

As a particular example, the β-lactams will be described. To protect against the constantly changing hostile environment, certain bacteria have developed a cell membrane which includes complex carbohydrate-peptide structures, assembled from individual carbohydrate and amino acid monomers in the cytoplasm and then transported out across the growing membrane for assembly. After export and attachment to the growing cell membrane, a free C-terminal end of a peptide is cross-linked to other chains to give the required rigidity to the cell membrane. Many β-lactam antibiotics block this step which occurs on the outside of the membrane, and which leads to weakening of the cell membrane and eventual cell-lysis (Rapley & Walker, 1993).

To compensate, the bacterium produces lactamase enzymes that hydrolyse an amide bond in the β-lactam antibiotics to inactivate them. In order to achieve this resistance, lactamase synthesis is induced in the cytoplasm and this protein has to be exported to the outer face of the membrane to be effective since the site of β-lactamase antibiotics are on the outside of the membrane. In gram positive bacteria, the β-lactamases are targeted first to the periplasmic space by a "peptide" leader sequence (Rapley & Walker, 1993).

As will now be indicated, many of the processes described in this resistance mechanism are controlled by methylation.

In assessing this collection of diverse information, the present inventors developed the idea that antimicrobial resistance could be reduced in practice using methylation inhibitors. Although many scientific articles have analyzed the mechanisms underlying antibiotic resistance, the idea of using methylation inhibitors has not been proposed previously.

The inventors now suggest that for the seven known antibiotic resistant mechanisms to operate, one prerequisite generally is the induction of the synthesis of at least one protein. They therefore predict that methylase inhibitors will have the ability to influence most, if not all, of these seven mechanisms. Evidence available in the literature indicates that methylation inhibitors do influence these mechanisms, although there was no suggestion to use such inhibitors in a clinical environment. It is now proposed that various methylation inhibitors alone could be used as antimicrobial agents and, more particularly, that their use in combination with known antimicrobials will reduce or eliminate resistance.

The present invention was developed in part from a detailed analysis of the scientific literature and an assimilation of known, but previously unconnected, facts. Certain of the publications in this area are described in the following sections.

Butler & Gotschlich (1991) reported that antibiotic resistance in *Neisseria gonorrhoeae* had been associated with the acquisition of R plasmids from heterologous organisms. RSF1010-like plasmids are the first multiresistant plasmid group found in Neisseria spp., having resistance not only to sulfonamides and streptomycin but also to ampicillin. They studied the possibility of dissemination of these plasmids into *N. gonorrhoeae*. It was found that RSF1010 could be mobilized into *N. gonorrhoeae* at a very low frequency, but this frequency increases by greater than 4 orders of magnitude when the plasmid DNA is methylated in vivo by a specific methylase. It was suggested that protection from digestion against the gonococcal restriction enzymes in vitro correlates with a substantial increase in the conjugal frequency.

Stein et al. (1988) demonstrated that transformation of gonococcal plasmid pFT180 isolated from *E. coli* HB101 or *N. gonorrhoeae* WR302 into that gonococcal strain PGH3-2 required in vitro methylation with a specific methylase. In the absence of methylation, a five-orders of magnitude decrease in the transformation frequency was observed.

Caboche & Bachellerie (1977) analyzed ribosomal RNA maturation in eukaryotes and observed that the global efficiency of the process of rRNA maturation is severely affected in qualitative terms. The undermethylation partially inhibits several stages in the maturation pathway and therefore does not block selectively at a definite step of processing. Two main alterations are observed. First, in the nucleus the life times of the various undermethylated intermediates of rRNA maturation are markedly increased and a significant accumulation of these forms is detected by long-term labelling studies. Second, the rate of appearance of 32S rRNA into the cytoplasm is severely affected in much higher proportions than the formation of its immediate precursor, nuclear 28S rRNA, suggesting that the lack of methylation may play an important role in the last step of maturation (possibly release into the cytoplasm).

Although bacteria contain no nuclei, the processing of rRNA is surprisingly similar to that of eukaryotes. Additionally, fungi and parasites are eukaryotes and should behave as described above. It is therefore expected that cycloleucine should have some of the same effects on bacterial rRNA maturation. The present invention is thus contemplated to be useful against bacteria and other microbial infections, e.g., those caused by yeast and parasitic microbes.

Yamaki et al. (1988) and others showed that dam methylation is important in the regulation of initiation of DNA replication in *E. coli*. These authors determined that the thermal melting temperature of the oriC region is lowered by adenine methylation at GATC sites. It is proposed that dam methylation might lead to more efficient transcription at promoters near oriC which may stimulate initiation of DNA replication at oriC. Recent studies also reportedly showed reduced frequency of transformation of oriC plasmids in dam mutants, and poor functioning of oriC plasmids derived from a dam mutant in an in vitro DNA replication system. This leads the inventors to predict that methylation inhibitors will likely slow down the efficiency transcription and replication of plasmids.

Sinefungin and SAH are known to effect DNA and protein methylases from Streptomyces and other bacteria and to inhibit the development of various fungi, viruses and parasites (e.g., Barbes et al., (1990). It has been reported that sinefungin inhibits the methylation of adenine or guanine to a greater extent than cytosine in tRNA (Vedel & Robert-Gero, 1981; Barbes et al., 1990). It has also been observed that DNA methylases from *S. antibioticus*, a non-sinefungin producer, are noticeably inhibited, but not in the producer *S. incarnatus*. Barbes et al. (1990) suggested that DNA methylation, and possibly RNA methylation, appear to be influenced in non-sinefungin producers. They also suggested that sinefungin could be a useful tool in investigating the physiological processes related to bacterial methylation, but did not suggest the clinical use of sinefungin in combination with antibiotics to reduce antibiotic resistance.

Yebra et al. (1991) reported that sinefungin and derivatives inhibited RNA methyltransferase in *S. antibioticus, S. incarnatus* and *S. griseolus*. The structural features of sinefungin that are essential for its inhibitory effect were also identified (Yebra et al., 1991, incorporated herein by reference). The maintenance of such important structural features in analogues intended for use in the present invention is required. When *E. coli* 16S and 23S rRNA were used as a substrate, lower exogenous methylation levels were observed, namely 10% of those obtained with tRNA.

Yebra et al. (1991) speculated further that, due to the instability of mRNA, that it is more conceivable that the modifications effected were on the precursors of mature rRNA and/or tRNA molecules during the process of formation. They also mentioned that sinefungin inhibits sporulation of *S. antibioticus*, but didn't inhibit the synthesis of DNA methyltransferases.

Lorian (1991) described the method of transduction in which bacteria acquire new DNA, including the transfer of resistance genes for β-lactamase and heavy metal-resistance plasmids of staphylococci, originally described in the 1960's and 1970's. These plasmids are packaged by a phage and carried from one cell to another, a process that has been shown to occur in vitro and in vivo.

It is generally accepted according to Lorian, that the most common mechanism of transfer of resistance genes is by conjugation in which cell-to-cell contact is made, and DNA from one cell (the donor) is transferred to another cell (the recipient). Therefore, in the latter case, the plasmid is able to mediate its own transfer by conjugation.

Razin et al. (1975) showed that methylation of bacteriophage DNA takes place during the last stage of DNA replication. The inhibition of this DNA methylation is accompanied by a corresponding decrease in phage production, indicating the vital role of the methylation step in the maturation of the virus. The Lorian and Razin papers suggest to the inventors that methylation inhibitors will likely disrupt plasmid/phage mediated antibiotic resistance.

Zyskind et al. (1992) indicated that three cellular processes occur during conversion of a mother bacterial cell into daughter cells: DNA replication, cell growth, and cell division. In procaryotic cells, the rate of replication is controlled not by the rate of chain elongation, but by the rate of initiation at the origin of replication, oriC. The authors suggested that one or more GATC sites in the origin region must be fully methylated for the origin to function in initiation. They concluded that as part of the mechanism, initiation can occur only after methylation of the DNA of the oriC region.

Protein carboxymethylase is involved in mediating bacterial chemotaxis (Diliberto et al., 1976; Aswad et al., 1974). Flagellated bacteria require S-adenosylmethionine's (SAM's) mediated methylation for chemotaxis. Additionally, a rapid reversible methylation of a protein in the cytoplasmic membrane of *E. coli* has been reported to increase substantially during the chemotactic response. The inventors expect that methylation inhibition would influence these processes to the detriment of the organism and that the combination of methylation inhibitors and antimicrobial agents will likely be synergistic.

Park et al. (1987) showed that N-methylation of apocytochrome c facilitates the import of this protein into the mitochondria by a specific receptor based mechanism, which further illustrates the central role of methylation. This may be relevant when the present invention is used against eukaryotic microbes.

Pandit et al. (1992) indicated that the presence of methylated cytosine residues in the integrated DNA is strongly correlated with the number of plasmid copies. They observed that hph genes heavily methylated contained many plasmid copies in transformants. In contrast, the genes those transformants that contains a single plasmid are not heavily methylated.

B. Transmethylation

Most transmethylation reactions involve the transfer of a donor methyl group from SAM to an acceptor molecule and result also in the formation of S-adenosylhomocysteine (SAH), which is an inhibitor of adenosylmethionine-dependent methyltransferases. Acceptor molecules in these reactions include protein carboxy groups, lysine groups, basic aminoacyl residues in proteins, phospholipids, nucleic acids and various small molecules. These reactions play an essential role in specialized biological phenomena, such as chemotaxis, neurosecretion, membrane receptor interactions, DNA modification restriction, gene expression, DNA transcription, RNA localization, RNA processing and cellular proliferation and differentiation (Lawrence & Robert-Gero, 1993).

Methylation is known to be important in RNA maturation Salim & Madden (1973). In HeLa cells, the 45S precursor ribosomal RNA is about 13,000 nucleotides long and is processed to form the 18S, 28S and 5.8S rRNAs. Extensive spacer regions are eliminated during the ribosomal RNA processing. Before processing, about 110 methylations, termed early methylation, occur rapidly in the nucleolus on the 45S rRNA. These are 2'-O-ribose methylations, and they occur in molar yields for nearly all positions. Cleavage then occurs to produce smaller RNAs in which all of the methyl groups are conserved. The 45S goes to 41S which, in turn, splits into two pathways: first, 41S to 32S to 28S rRNA; and second, 41S to 20S to 18S rRNA. Subsequently, during late maturation, seven base methylations occur.

It is known that inhibition of methylation leads to serious extensive degradation of rRNA in Hela cells (Lhoest & Colson, 1990). Although these authors cited studies where it appears that under methylation does not play an important role in prokaryotic rRNA maturation, other studies showed that inhibition of methylation by sinefungin in S.cerevisiae leads to a decrease in stable 18S rRNA (Li et al., 1985).

Figure 1B:
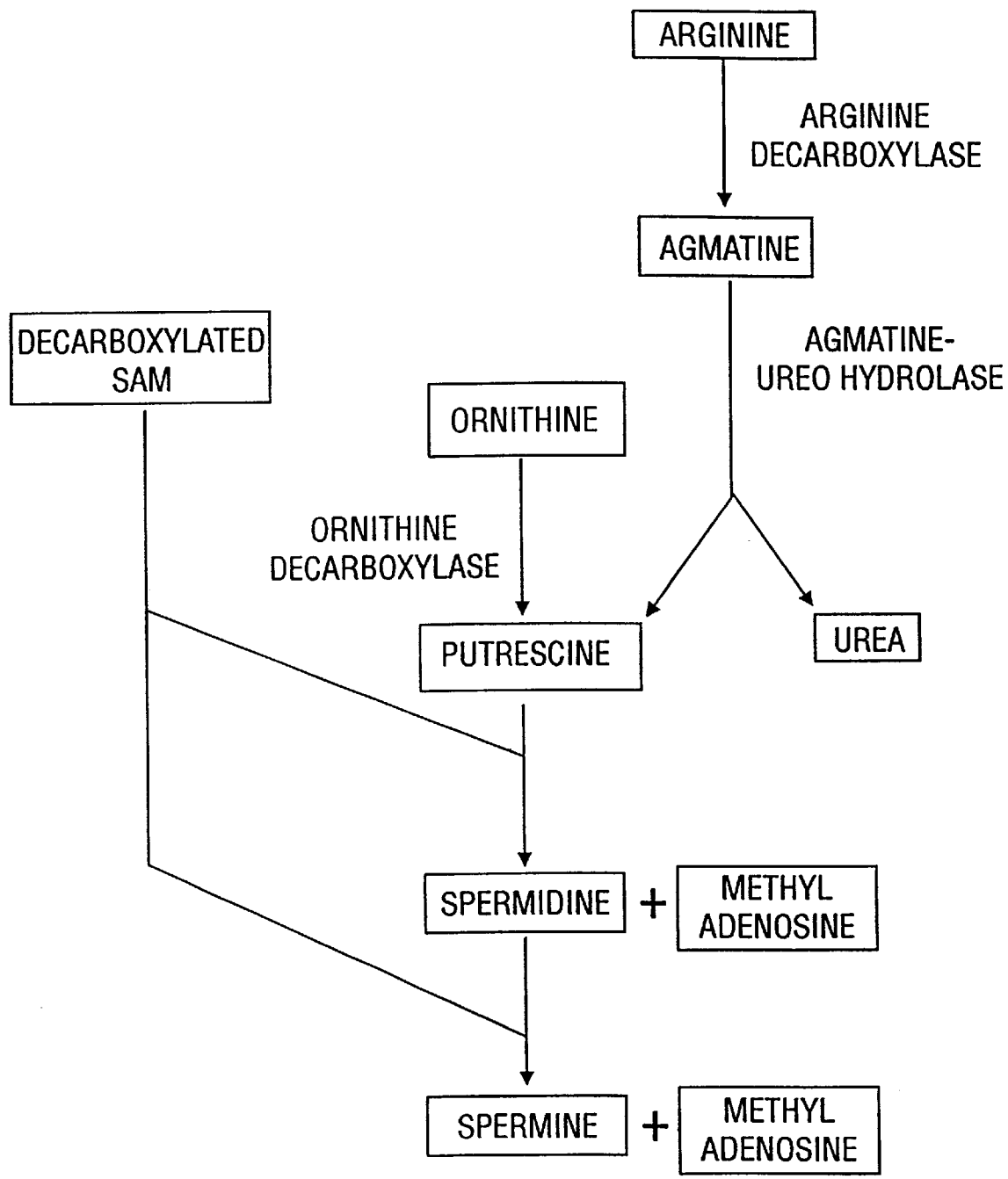

SAM serves as the methyl donor for numerous methyltransferase reactions (De Clercq, 1987). SAM itself is synthesized from ATP and methionine (FIG. 1A and FIG. 1B). SAH, which is a product of, and an inhibitor of, methyltransferase reactions, is generated when transfer of a methyl group from SAM to acceptor substrate occurs. To avoid SAH-mediated of inhibition and to allow the methyltransferases to proceed with their action, SAH has to be removed by the enzyme SAH hydrolase. SAH hydrolase catalyzes the reversible hydrolysis of SAH to homocysteine and adenosine. Homocysteine and adenosine, in turn, are product inhibitors of the SAH hydrolase reaction, which means that they have to be removed if SAH hydrolase is to proceed with its catalatic function. This can be achieved by several pathways which involve conversion of homocysteine to methionine, to cysteine or to oxidation products, and conversion of adenosine to inosine by adenosine deaminase.

It can thus be seen that effective methylation requires the concerted action of at least three types of enzymes: methyltransferases, SAH hydrolase, adenosine deaminase and several enzymes involving homocysteine. Based on this requirement, the inventors envision certain primary types of methylation inhibitors for use in connection with MLS antibiotics: compounds that inhibit methyltransferases; SAH analogues, acyclic and carbocyclic adenosine analogues that inhibit SAH hydrolase; inhibitors of adenosine deaminase and homocysteine metabolism.

Furthermore, methylation will also be influenced if the synthesis of SAM or methionine is altered. Therefore, inhibition of any enzymes required for the synthesis of SAM, such as SAM synthetase, dihydropteroate synthase, dihydrofolic reductase and homocysteinetransmethylase are contemplated to be effective ways by which to lower the effective concentration of SAM, and thus to decrease the level of methylation reactions. Additionally, compounds that inhibit maturation of rRNA subunits and any step in protein translation are also contemplated to be useful, as are compounds that inhibit polyamine synthesis.

A large number of methylation inhibitors have been described in the literature and, although none have been proposed for use in conjunction with reducing MLS antibiotic resistance, many such inhibitors have been studied for their ability to affect mRNA and small molecule methylation. The preparation and use of various compounds and agents that are capable of inhibiting bacterial RNA methylation, synthesis and/or maturation is described further in the detailed examples.

C. MLS Antibiotics

Weisblum (1984) reported that what appeared initially as uncomplicated resistance to erythromycin in gram positive bacteria, actually constituted a resistance syndrome, dependent upon biochemical modification of the 50S ribosome subunit, which in turn, confers resistance to three chemically distinct classes of antibiotics—the macrolides, lincosamides, and streptogramin type B (MLS) antibiotics. Bacteria become resistant to erythromycin by single biochemical alteration of the ribosomes, as a result of which, the affinity between the drug and ribosome is reduced. By this single alteration, namely, $N^6$-methylation or $N^6,N^6$-dimethylation of adenine in 23S ribosomal RNA, a structural component of the 50S ribosome subunit, bacteria become more generally resistant to the MLS antibiotics.

The MLS antibiotics comprise three of at least ten chemical distinct classes that inhibit protein synthesis by their action on the 50S ribosomal subunit. In view of the apparent functional relationship defined by observed co-resistant patterns, these three group of inhibitors were designated collectively as the MLS antibiotics.

MLS antibiotics are chemically distinct but have a similar mode of action. Their spectrum of activity includes gram-positive cocci (in particular, staphylococci, streptococci, and enterococci) and bacilli and gram negative cocci. These drugs, especially clindamycin, are also potent against anaerobic bacteria. Gram-negative bacilli are usually resistant to MLS antibiotics, but certain enteric bacilli and Haemophilus spp. are susceptible to azithromycin. The activities of these antibiotics against Campylobacter, Legionella and Chlamydia spp. are at the origin of the recent renaissance of erythromycin.

Macrolides are composed of a minimum of two amino and/or neutral sugars attached to a lactone ring of variable size. Macrolides that are commercially available or in clinical development can be divided into 14-, 15-. and 16-membered lactone ring macrolides. These classes differ in their pharmacokinetics properties and in their responses to bacterial resistance mechanisms. Lincosamides (lincomycin and the more active semisynthetic derivative clindamycin) are alkyl derivatives of proline and are devoid of a lactone ring. Streptogramin antibiotics are used clinically in certain countries, including Belgium and France. They are composed of two factors, A and B (II and I in pristinamycin and M and S in virginiamycin, respectively), that act synergistically and are produced by the same microorganism.

In 1956, a few years after the clinical introduction of erythromycin, resistance of staphylococci to this drug emerged and subsequently spread to France, the United Kingdom, and the United States. The MLS cross-resistance phenotype due to modification of the drug rRNA target is widely distributed. Resistance has since been detected in Staphylococcus spp., Streptococcus spp., Enterococcus spp., Corynebacterium diphtheria, Bacteroides spp., Clostridium spp., Bacillus spp., Lactobacillus spp., *Mycoplasma pneumonia*, Campylobacter spp. Propionibacterium spp. and members of the family Enterobacteriaceae. (LeClercq & Courvalin, 1991). The structure of erythromycin A, the proto-typical macrolide is shown below:

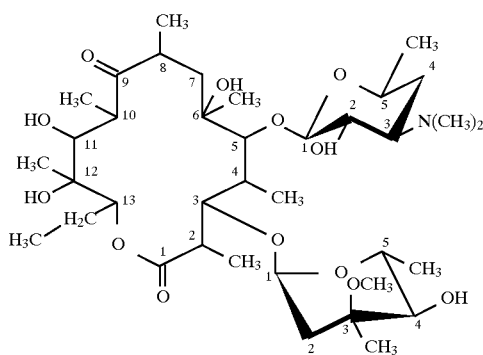

In the erythromycin family, three compounds are typically used clinically: erythromycin, azithromycin and clarithromycin (Reese & Betts, 1993). Erythromycin is one of the safest antibiotics in current clinical use. Bacteria known to be susceptible to erythromycin are listed in Table 6 (taken from Lorian, 1991) and in Table 7 (taken from Reese & Betts, 1993). This further serves to indicate the utility of the invention and the wide-ranging clinical use for the combinations disclosed herein.

Azithromycin a new azolide antibiotic approved for clinical use in 1991. This is a novel 15-member azolide antibiotic. Its structure differs from that of erythromycin in that the lactone ring contains a nitrogen atom. This molecular rearrangement has resulted in a compound with an increased spectrum of activity, yielding high and sustained tissue antibiotic levels that are much greater than the serum antibiotic levels, and prolonged tissue half-life. This allows for fewer doses during a course of therapy.

Clarithromycin is chemically different from erythromycin by having an O-methyl substitution at position 6 of the macrolide ring. Its spectrum of activity is similar to that of erythromycin, except for enhanced *H. influenzae* activity, but it has better stability properties, including a twice-daily dose regimen.

The mechanism of action of the erythromycin-like antibiotics involves binding to rRNA and prevention of bacterial protein synthesis. The ermC gene confers resistance to erythromycin in gram-positive bacteria by specifying a 23S rRNA methylase that $N^6$-methylates or $N^6,N^6$-dimethylates an adenine residue at position 2,058 on the 23S rRNA, thus decreasing ribosomal affinity for erythromycin at that site (Skinner et al., 1983; Weisblum et al., 1971). The ermC expression is induced by erythromycin, and erythromycin binding to unmethylated ribosomes is required for induction. The induction mechanism, termed translational attenuation, has been intensively studied (Denoya et al., 1986).

The ermC mRNA exists in an inactive confirmation in which the ribosome binding site (Shine Dalgarno sequence [CD2]) for methylase synthesis is sequestered by base pairing in a double-stranded region. Stalling of a ribosome under the influence of erythromycin binding during translation of a 19 amino acid leader peptide causes the inactive mRNA structure to open, allowing initiation of methylase synthesis. Translation induction appears to be further regulated by a methylation-mediated feedback loop. Upon induction, the intracellular level of methylase increases, as does the number of methylated ribosomes, with a co-commitment decrease of the ribosomal affinity for erythromycin and prevention of further induction. The overall regulation of ermC expression has been summarized by Denoya et al. (1986).

Zalacain & Cundliffe (1990) described methylation of 23S ribosomal RNA due to carB, an antibiotic-resistance determinant from the carbomycin producer Streptomyces thermotolerans. They showed the carB product monomethylates the amino group of the adenosine residue located at position 2058 in 23S rRNA. In contrast, ribosomes from *S. lividans* expressing ermE, in which the 23S rRNA is dimethylated at this same position, are highly resistant to macrolides and insensitive to lincosamides. Thakker-Varia et al. (1985) reported that the methylation reaction is affected by a class of methylase, whose genes are typically plasmid- or transposon-associated, and whose synthesis is inducible by erythromycin.

There are apparently no practical proposals in the literature as to how bacterial resistance to MLS antibiotics may be overcome. Although generally applicable to all antimicrobial agents, the present inventors particularly propose the use of one or more methylation inhibitors, in conjunction with MLS antibiotics. These will reduce the bacterium's ability to methylate rRNA and allow the antibiotics to bind to their natural rRNA targets, thus inhibiting protein synthesis. Although elegantly simple in hindsight, this represents a novel and important development in anti-microbial strategies.

The following examples are included to demonstrate preferred embodiments of the invention. It should be appreciated by those of skill in the art that the techniques disclosed in the examples that follow represent techniques proposed by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE I

Antibiotic Treatment

Antibiotics such as erythromycin, clindamycin, azithromycin, clarithromycin, vancomycin and the like, may be used clinically at a range of doses. Depending on the circumstances, antimicrobial agents may be employed in oral or parenteral treatment regimens. Appropriate doses are well known to those of skill in the art and are described in various publications, such as (Reese & Betts, 1993; incorporated herein by reference). Table 4 and Table 5 (taken from Reese & Betts, 1993) are included herein to provide ready reference to the currently recommended doses of a variety of antimicrobial agents.

Following are definitions of terms that are used in Table 4 and Table 5: qid (4 times daily), tid (3 times daily), bid (twice daily), qd (once daily), q4h (every 4 hours around the clock), q6h (every 6 hours around the clock) and q8h (every 8 hours around the clock).

TABLE 4

COMMON ANTIBIOTICS AND USUAL ORAL DOSES

| ANTIBIOTIC | DOSAGE |
|---|---|
| Penicillin V | 250 mg qid |
| Rugby (generic) | |
| V-cillin K | |
| Dicloxacillin | 250 mg qid |
| Glenlawn (generic) | |
| Dynapen | |
| Cloxacillin (Tegopen) | 250 mg qid |
| Amoxicillin | 250 mg tid |
| Rugby (generic) | |
| Polymox | |
| Ampicillin | 250 mg qid |
| Moore (generic) | |
| Polycillin | |
| Augmentin | tid |
| 250-mg tablets | |
| chewables (250 mg) | |
| 125-mg (suspension) | |
| chewables (125 mg) | |
| Carbenicillin (Geocillin) | 382 mg qid (1 tb) |
| | 2 tab qid |
| Cephalexin | 250 mg qid |
| Rugby (generic) | |
| Keflex | |
| Rugby (generic) | 500 mg qid |
| Keflex | |
| Cefadroxil | 1 gm bid |
| Rugby (generic) | |
| Duricef | |
| Cephradine | 250 mg qid |
| Rugby (generic | |
| Velosef | |
| Rugby (generic) | 500 mg qid |
| Velosef | |
| Cefaclor | 250 mg tid |
| Ceclor | |
| Cefuroxime axetil | |
| Ceftin | 125 mg bid |
| | 250 mg bid |
| | 500 mg bid |
| Cefixime | 400 mg q24h |
| Suprax | |
| Cefprozil | 250 mg q12h |
| Cefzil | |
| Loracarbef (Lorabid) | 200 mg bid |
| Cefpodoxime proxetil | 200 mg bid |
| (Vantin) | |
| Clindamycin | 300 mg q8h |
| Cleocin | |
| TMP/SMZ | 1 double-strength bid |
| Bactrim | |
| Septra | |
| (generic) | |
| Trimethoprim | 100 mg bid |
| Rugby (generic) | |
| Proloprim | |
| Erythromycin (base) | 250 mg gid |
| Abbott | |
| E-mycin (delayed release) | |
| Erythromycin stearate | 250 mg qid |
| Rugby (generic) | |
| Azithromycin | 1 g once only 500 mg, |
| Zithromax | day 1, plus 250 mg, day 2–5 |
| Clarithromycin | 250 mg bid |
| Biaxin | 500 mg bid |

TABLE 4-continued

COMMON ANTIBIOTICS AND USUAL ORAL DOSES

| ANTIBIOTIC | DOSAGE |
|---|---|
| Tetracycline hydrochloride | 250 mg qid |
| Mylan | |
| Sumycin 250 | |
| Doxycycline | 100 mg qd (with 200-mg |
| Lederle (generic) | initial load) |
| Vibramycin | |
| Vancomycin | Capsules |
| Vancocin HCl (oral soln/powder) | 125 mg q6h PO |
| Metronidazole | 250 mg qid |
| Rugby (generic) | |
| Flagyl | |
| Norfloxacin | 400 mg bid |
| Noroxin | |
| Ciprofloxacin | 250 mg bid |
| Cipro | 500 mg bid |
| | 750 mg bid |
| Ofloxacin | 200 mg bid |
| Floxin | 300 mg bid |
| | 400 mg bid |
| Lomefloxacin Maxaquin | 400 mg once qd |

TABLE 5

COMMON ANTIBIOTICS AND USUAL PARENTERAL DOSES

| ANTIBIOTIC | DOSAGE |
|---|---|
| Penicillin G | 2,400,000 units |
| Pfizerpen G (Pfizer) | 12 million units |
| Oxacillin | 12 g |
| Prostaphlin (Bristol) | |
| Nafcillin | 12 g |
| Nafcil (Bristol) | |
| Ampicillin | 6 g |
| Omnipen (Wyeth) | |
| Ticarcillin | 18 g |
| Ticar (Beecham) | |
| Piperacillin | 18 g |
| Pipracil (Lederle) | 16 g |
| Mezlocillin | 18 g |
| Mezlin (Miles) | 16 g |
| Ticarcillin-clavulanate | 18 g/0.6 g |
| Timentin (Beecham) | 12 g/0.4 g |
| Ampicillin-sulbactam | 6 g |
| Unasyn (Roerig) | 12 g |
| Cephalothin | 9 g (1.5 g q4h) |
| Keflin (Lilly) | |
| Cefazolin | 4 g (1 g q6h) |
| Ancef (SKF) | 3 g (1 g q8h) |
| Cefuroxime | 6 g 2.25 g (750 mg q8h) |
| Zinacef (Glaxo) | 4.5 g (1.5 g q8h) |
| Cefamandole | 9 g (1.5 g q4h) |
| Mandol (Lilly) | |
| Cefoxitin | 8 g (2 g q6h) |
| Mefoxin (MSD) | 6 g (2 g q8h) |
| Cefonicid | 1 g q12h |
| Monicid (SKF) | |
| Cefotetan | 2 g q12h |
| Cefotan (Stuart) | |
| Cefmetazole | 2 g q8h |
| Zefazone (Upjohn) | |
| Ceftriaxone | 2 g (2.0 g q24h) |
| Rocephin (Roche) | 1 g (1.0 g q24h) |
| Ceftazidime | 6 g (2 g q8h) |
| Fortax (Glaxo) | |
| Taxicef (SKF) | |
| Tozidime (Lilly) | |
| Cefotaxime | 2 g q6h |
| Claforan (Hoechst) | 2 g q8h |
| Cefoperazone | 8 g (2 g q6h) |
| Cefobid (Pfizer) | 6 g (2 g q8h) |

TABLE 5-continued

COMMON ANTIBIOTICS AND USUAL PARENTERAL DOSES

| ANTIBIOTIC | DOSAGE |
|---|---|
| Ceftizoxime | (2 g q8h) |
| Ceftizox (SKF) | |
| Aztreonam | 2 g q8h |
| Azactam (Squibb) | 1 g q8h |
| Imipenem | 2000 mg (500 mg 16h) |
| Primaxin (MSD) | |
| Gentamicin | 360 mg (1.5 mg/kg q8h |
| Garamycin | for an 80-kg patient) |
| (Schering) | |
| (generic) (Elkins-Sinn) | |
| Tobramycin | 360 mg (1.5 mg/kg q8h |
| Nebcin (Dista) | for an 80-kg patient) |
| Amikacin | 1200 mg (7.5 mg/kg q12h |
| Amikin (Bristol) | for an 80-kg patient) |
| Clindamycin | 2400 mg (600 mg q6h) |
| Cleocin (Upjohn) | 2700 mg (900 mg q8h) |
| | 1800 mg (600 mg q8h) |
| Chloramphenicol | 4 g (1 g q6h) |
| Chloromycetin (P/D) | |
| TMP/SMZ | 1400 mg TMP (5 mg TMP/kg |
| Septra (Burroughs Wellcom) | q6h for a 70-kg patient) |
| | 700 mg TMP (5 mg TMP/kg |
| | q12h for a 70-kg |
| | patient) |
| Erythromycin | 2000 mg (500 mg q6h) |
| Erythromycin | |
| (Elkins-Sinn) | |
| Doxycycline | 200 mg (100 mg q12h) |
| Vibramycin (Pfizer) | |
| Vancomycin | 2000 mg (500 mg q6h) |
| Vancocin (Lilly) | |
| Metronidazole | 2000 mg (500 mg q6h) |
| (generic) (Elkins-Sinn) | |
| Ciprofloxacin | 200 mg q12h |
| Cipro | 400 mg q12h |
| Pentamidine | 280 mg (4 mg/kg q24h for |
| Pentam (LyphoMed) | a 70-kg patient) |

The effectiveness of erythromycin and lincomycin against a wide variety of organisms is shown in Table 6 (taken from Lorian, 5 1991). Table 7 (taken from Reese & Betts, 1993), is provided as a comparison of certain common MLS antibiotics. The data presented in the tables of the present specification is another tool to enable the straightforward comparison of raw data with accepted clinical practice and to allow the determination of appropriate doses of combined agents for clinical use.

TABLE 6

SUSCEPTIBILITY TO ANTIBIOTICS

| Species | (n) | Range | MIC$_{50}$ | MIC$_{90}$ |
|---|---|---|---|---|
| ERYTHROMYCIN | | | | |
| *Bacillus spp.* | 20 | 0.03–2 | 0.25 | 2 |
| *Bacteroides fragilis* | 97 | ≦0.25–16 | 1 | 8 |
| *Bordetella bronchiseptica* | 11 | 4–32 | 8 | 32 |
| *Bordetella parapertussis* | 46 | ≦0.125–4 | 0.25 | 0.25 |
| *Bordetella pertussis* | 32 | 1–0.5 | 0.25 | 0.25 |
| *Bordetella pertussis* | 75 | ≦0.125–0.5 | ≦0.125 | ≦0.125 |
| *Borrelia burgdorferi* | 10 | 0.03–0.125 | 0.03 | 0.06 |
| Branhamella (Moraxella) *catarrhalis* | 20 | ≦0.125–0.5 | 0.25 | 0.25 |
| Branhamella (Moraxella) *catarrhalis* | 20 | 0.125–0.5 | 0.25 | 1 |
| Branhamella (Moraxella) *catarrhalis* (non β-lactamase producer) | 40 | ≦0.06–0.5 | 0.25 | 0.5 |
| Branhamella (Moraxella) *catarrhalis* (non β-lactamase producer) | 13 | 0.03–0.125 | 0.06 | 0.06 |
| Branhamella (Moraxella) *catarrhalis* (non β-lactamase producer) | 14 | ≦0.06–1 | 0.125 | 1 |
| Branhamella (Moraxella) *catarrhalis* (non β-lactamase producer) | 16 | 0.015–1 | 0.06 | 0.25 |
| Branhamella (Moraxella) *catarrhalis* (β-lactamase producer) | 47 | ≦0.06–1 | 0.25 | 0.5 |
| Branhamella (Moraxella) *catarrhalis* (β-lactamase producer) | 58 | 0.03–0.25 | 0.125 | 0.125 |
| Branhamella (Moraxella) *catarrhalis* (β-lactamase producer) | 160 | ≦0.06–8 | 0.25 | 0.5 |
| Branhamella (Moraxella) *catarrhalis* (β-lactamase producer) | 35 | 0.03–0.125 | 0.06 | 0.06 |
| *Campylobacter jejuni* | 25 | 0.5–8 | 1 | 4 |
| *Campylobacter jejuni* | 16 | 0.125–4 | 0.25 | 2 |
| *Campylobacter pylori* | 56 | 0.25–16 | 0.5 | 1 |
| *Campylobacter pylori* | 13 | 0.125–0.25 | 0.125 | 0.25 |
| Corynebacterium JK | 102 | 0.5–≧128 | ≧128 | ≧128 |
| Corynebacterium JK | 19 | 0.125–≧64 | 2 | ≧64 |
| *Enterococcus faecalis* | 26 | 1–≧64 | 1 | 4 |
| *Enterococcus faecalis* | 50 | 0.06–≧64 | 4 | ≧64 |
| *Enterococcus faecalis* | 86 | 0.125–≧64 | 1 | ≧64 |
| *Enterococcus faecalis* | 97 | 0.125–128 | 2 | 128 |
| *Enterococcus faecium* | 14 | ≦0.06–≧64 | 1 | ≧64 |
| *Enterococcus spp.* | 35 | ≦0.06–≧32 | 2 | ≧32 |
| *Haemophilus ducreyi* | 122 | ?–0.125 | 0.004 | 0.06 |
| *Haemophilus influenzae* | 145 | 0.5–8 | 2 | 2 |
| *Haemophilus influenzae* | 97 | 0.25–≧16 | 1 | 4 |
| *Haemophilus influenzae* (non β-lactamase producer) | 22 | 0.125–8 | 2 | 4 |
| *Haemophilus influenzae* (non β-lactamase producer) | 137 | ≦0.06–≧8 | 4 | 8 |
| *Haemophilus influenzae* (β-lactamase producer) | 46 | ≦0.06–≦8 | 4 | 8 |
| *Haemophilus influenzae* (β-lactamase producer) | 17 | 0.25–4 | 2 | 4 |
| *Haemophilus influenzae* (penicillin susceptible) | 22 | 0.25–16 | 8 | 16 |
| *Haemophilus influenzae* (penicillin resistant) | 20 | 8–16 | 8 | 16 |
| *Haemophilus parainfluenzae* | 13 | 0.5–8 | 2 | 4 |
| *Legionella spp.* | 23 | 0.03–0.25 | 0.125 | 0.25 |
| *Legionella pneumophila* | 31 | ≦0.0075–0.25 | 0.06 | 0.125 |
| *Legionella pneumophila* | 48 | 0.03–2 | 0.25 | 0.5 |
| *Legionella pneumophila* | 25 | 0.125–1 | 0.25 | 1 |
| *Listeria monocytogenes* | 13 | 0.5–1 | 0.5 | 0.5 |
| *Listeria monocytogenes* | 16 | 0.125–2 | 0.25 | 1 |
| *Listeria monocytogenes* | 65 | ≦0.06–≧32 | 0.125 | 32 |
| *Mycoplasma hominis* | 26 | ≦128 | ≧128 | ≧128 |
| *Mycoplasma hominis* | 20 | ≦256 | ≧256 | ≧256 |
| *Mycoplasma pneumoniae* | 10 | ≦0.06–8 | ≦0.06 | ≦0.06 |
| *Mycoplasma pneumoniae* | 14 | ≦0.004–0.03 | ≦0.004 | ≦0.004 |
| *Neisseria gonorrhoeae* | 19 | 0.0075–8 | 0.25 | 1 |
| *Neisseria gonorrhoeae* (non β-lactamase producer) | 73 | 0.015–4 | 0.25 | 2 |
| *Neisseria gonorrhoeae* (non β-lactamase producer) | 78 | 0.03–2 | 0.25 | 1 |
| *Neisseria gonorrhoeae* (β-lactamase producer) | 12 | 0.03–4 | 0.5 | 2 |
| *Neisseria gonorrhoeae* (β-lactamase producer) | 17 | 1–4 | 2 | 4 |
| *Neisseria meningitidis* | 19 | 0.5–8 | 1 | 8 |
| *Nocardia asteroides* | 78 | ≦0.25–≧8 | ≧8 | ≧8 |

TABLE 6-continued

SUSCEPTIBILITY TO ANTIBIOTICS

| Species | (n) | Range | MIC$_{50}$ | MIC$_{90}$ |
|---|---|---|---|---|
| Staphylococcus aureus | 44 | 0.125–1 | 0.125 | 0.5 |
| Staphylococcus aureus | 100 | 0.25–128 | 0.5 | 4 |
| Staphylococcus aureus (penicillin susceptible) | 20 | 0.125–0.5 | 0.5 | 0.5 |
| Staphylococcus aureus (penicillin susceptible) | 35 | ≦0.06–≧32 | 0.25 | 0.5 |
| Staphylococcus aureus (penicillin resistant) | 35 | 0.25–≧32 | 0.25 | ≧32 |
| Staphylococcus aureus (methicillin susceptible) | 28 | 0.125–1 | 0.25 | 0.5 |
| Staphylococcus aureus (methicillin susceptible) | 97 | ≦0.125–≧64 | 0.25 | ≧64 |
| Staphylococcus aureus (methicillin susceptible) | 20 | 0.125–1 | 0.5 | 0.5 |
| Staphylococcus aureus (methicillin resistant) | 17 | 0.5–≧128 | 128 | 128 |
| Staphylococcus aureus (methicillin resistant) | 15 | ≧64 | ≧64 | ≧64 |
| Staphylococcus aureus (methicillin resistant) | 20 | ≧64 | ≧64 | ≧64 |
| Staphylococcus aureus (methicillin resistant) | 30 | ≦0.06–≧32 | ≧32 | ≧32 |
| Staphylococcus coagulase φ | 10 | 0.125–4 | 0.25 | 2 |
| Staphylococcus coagulase φ | 100 | 0.125–≧64 | 0.25 | ≧64 |
| Staphylococcus coagulase φ (non β-lactamase producer) | 12 | 0.03–8 | 0.125 | 0.25 |
| Staphylococcus coagulase φ (β-lactamase producer) | 38 | 0.06–16 | 0.125 | 4 |
| Staphylococcus epidermidis | 50 | 0.125–≧64 | ≧64 | ≧64 |
| Staphylococcus haemolyticus | 20 | 0.125–≧64 | ≧64 | ≧64 |
| Staphylococcus hominis | 20 | 0.125–≧64 | ≧64 | ≧64 |
| Streptococcus agalactiae | 20 | 0.03–0.25 | 0.03 | 0.125 |
| Streptococcus agalactiae | 34 | 0.015–0.06 | 0.03 | 0.03 |
| Streptococcus pneumoniae | 58 | 0.03–0.25 | 0.06 | 0.125 |
| Streptococcus pneumoniae | 91 | 0.125–4 | 0.125 | 0.125 |
| Streptococcus pneumoniae | 50 | 0.015–0.06 | 0.03 | 0.03 |
| Streptococcus pneumoniae | 16 | ≦0.03–0.125 | 0.06 | 0.125 |
| Streptococcus pneumoniae | 26 | 0.015–0.25 | 0.03 | 0.06 |
| Streptococcus pneumoniae | 50 | 0.03–0.125 | 0.06 | 0.06 |
| Streptococcus pyogenes | 19 | 0.03–0.25 | 0.06 | 0.125 |
| Streptococcus pyogenes | 20 | ≦0.03–0.25 | 0.06 | 0.125 |
| Streptococcus pyogenes | 33 | 0.015–0.03 | 0.03 | 0.03 |
| Streptococcus pyogenes | 20 | ≦0.06–≧32 | 0.125 | ≧32 |
| Streptococcus spp. | 22 | 0.015–0.25 | 0.03 | 0.06 |
| Streptococcus spp. | 107 | 0.004–2 | 0.03 | 1 |
| Ureaplasma urealyticum | 28 | 0.015–≧256 | 2 | ≧256 |
| Ureaplasma urealyticum | 19 | 8–≧128 | 16 | 32 |
| LINCOMYCIN | | | | |
| Mycoplasma hominis | 28 | 0.5–16 | 2 | 4 |
| Mycoplasma pneumoniae | 11 | 2–32 | 8 | 32 |
| Staphylococcus aureus | 100 | 0.5–512 | 1 | 1 |
| Ureaplasma urealyticum | 19 | 64–≧128 | ≧128 | ≧128 |

TABLE 7

IN VITRO ACTIVITY AND COMPARISON OF SELECTED MACROLIDE ANTIBIOTICS

| Organism | Azithromycin MIC$_{90}$ | Clarithromycin MIC$_{90}$ | Erythromycin MIC$_{90}$ |
|---|---|---|---|
| Gram-positive aerobes | | | |
| Staphylococcus aureus | | | |
| Methicillin susceptible | 1.0[a] | 0.12–0.24[a] | 0.25–0.50 |
| Methicillin resistant | >128.0 | >128.0 | >128.0 |
| Streptococcus pyogenes (group A) | | | |
| Erythromycin susceptible | 0.12[a] | 0.015[a] | 0.03[a] |
| Streptococcus pneumoniae | 0.12[a] | 0.015[a] | 0.03–1.0[a] |
| Streptococcus agalactactiae (group B) | 0.5[a] | 0.03–0.25[a] | 0.03–0.25[a] |
| Streptococcus bovis | 0.25 | | |
| Enterococci (group D) | | | |
| E. faecalis | | | |
| (Erythromycin susceptible) | 8.0 | | |
| (Erythromycin resistant) | >64.0 | | |
| E. facium | | | |
| Viridans streptococci | 16.0 | 0.03 | 0.06 |
| Coagulase-negative staphylococci | | | |
| Methicillin resistant | >128.0 | | |
| Methicillin susceptible | | | |
| Listeria monocytogenes | 4.0 | 0.12–2.0 | 0.5–2.0 |
| Gram-negative aerobes | | | |
| Haemophilus influenzae | 1.0 | 2.0–16.0 | 4.0–8.0 |
| Moraxella catarrhalis | 0.5 | 0.25–1.0 | 0.25–2.0 |
| Neisseria gonorrhoeae | 0.15 | 0.25–2.0 | 0.25–2.0 |
| N. meningitidis | 0.12 | — | 0.4–1.6 |

TABLE 7-continued

IN VITRO ACTIVITY AND COMPARISON OF SELECTED MACROLIDE ANTIBIOTICS

| Organism | Azithromycin $MIC_{90}$ | Clarithromycin $MIC_{90}$ | Erythromycin $MIC_{90}$ |
|---|---|---|---|
| *Pasteurella multocida* | 0.5 | — | — |
| *Bordetella pertussis* | 0.12 | — | 0.3–1.6 |
| *Legionella pneumophila* | 0.25–2.0 | 0.25 | 1.0–2.0 |
| *Campylobacter species* | 0.25 | 1.0–8.0 | 0.2–>50.0 |
| Anaerobes | | | |
| Gram-positive *cocci (peptococcus, peptostreptococcus)* | 2.0 | 4.0–>32.0 | 2.0–>32.0 |
| *Bacteroides fragilis* | 8.0 | 2.0–8.0 | 4.0–32.0 |
| *Clostridium perfringens* | 1.0 | 0.5–2.0 | 1.0 |
| Miscellaneous | | | |
| *Chlamydia pneumoniae* (formerly TWAR) | 0.12–0.25–1.0 | 0.007 | 0.065–1.0 |
| *Chlamydia trachomatis* | 0.12–0.25 | 0.06–0.125 | 0.12–0.25 |
| *Mycoplasma pneumoniae* | 0.001 | 0.008–0.03 | 0.004 |

[a]Erythromycin-resistant organisms will be resistant to erythromycin alone.

Using the strategy of the present invention, it also possible to use other antimicrobial agents in combination with the MLS antibiotics and inhibitors described herein. The use of antibiotic combinations is well established, for example, see Eliopoulous & Moellering (1991; incorporated herein by reference). Combinations are used primarily for two reasons: to provide broad-spectrum coverage in patients that are seriously ill and who may be come septicemic and, less frequently, because an identified organism is resistant to traditional doses of single antibiotics, but which the antibiotic combination may give the desired antimicrobial effect. Here it should be noted that the reversal of MLS antibiotic resistance is not discussed in (Eliopoulous & Moellering, 1991), highlighting the need for a new development in this area.

Mechanistic considerations are not important to practicing the invention, with the appropriate antibiotic doses and times for administration being generally known to those practicing in this area (e.g., defined doses at two, three of four times per day). However, the inventors did consider the underlying mechanisms in choosing certain currently preferred modes of administration in regard to MLS antibiotics and methylation inhibitors.

The inventors reasoned that bacterial cells generally contain $10^3$–$10^4$ ribosomes, that the induction of methylases reach a steady state of about $10^3$–$10^4$ molecules in about 2–3 hours, and that induction stabilizes the erm mRNAs half life from 2–3 minutes to 45 minutes (Denoya et al., 1986). Additionally it has been shown that the first resistant cells appear in about 20 minutes. From the known rate of peptidyl transferase catalysis (Devlin, 1986) and the rate of rRNA methylation, it is clear that inductive methylase synthesis occurs rapidly, and it is estimated that most of the ribosomes are methylated within one generation.

Following the induction of methylase synthesis, resistance to erythromycin rapidly occurs. Theoretically, principles suggest that to reduce or reverse erythromycin resistance, the best treatment regimen will be when (a) the induction of the synthesis of the methylase is prevented and/or (b) when methylation of the rRNA is prevented. Both of these can be achieved in a number of ways, using appropriate inhibitors, e.g., where the concentration of the methylating agent SAM is decreased. A preferred treatment will involve the pre-administration of an inhibitor for a given time period sufficient to decrease both protein synthesis and the concentration of SAM, then followed by the administration of the antimicrobial alone or in combination with more of the same or further inhibitor(s).

EXAMPLE II

Evaluation of Antibiotic Susceptibility

1. Disk Susceptibility Test

To more precisely define appropriate doses of inhibitors, or second agents, for use with MLS antibiotics, the inventors contemplate using a disk susceptibility test. Disk susceptibility testing is widely used in clinical laboratories (Acar & Goldstein, 1991; Shungu, 1991). The principle of these methods involves the use of a constant concentration of an antibiotic within a reservoir in the agar that is used to culture the organisms of interest. The susceptibility of the organism to the antibiotic is indicated by a clear zone of inhibition around the reservoir. The diameter of the zone of inhibition is proportional to the susceptibility of the organisms in question. The diameter of the clear zone of bacteria in the presence of antibiotics is known at the minimum inhibitory concentration (MIC), therefore bacterial strains resistant to an antibiotic can be identified quite easily from the diameter of the clear zone; resistant bacteria having a small clear zone diameter. The diffusion technique developed by Bauer et al. (1966) is the technique also recommended by the FDA and has been the technique most widely used in the clinical laboratory. This method is endorsed by the WHO and the National Committee for Clinical Laboratory Standards (NCCLS, see NCCLS Document, 1993).

The effect of more than one antibiotic, or other agent, on a bacterium is also easily examined with agar disk susceptibility testing. In one such example for use with the present invention, one would use two disks, one each impregnated with an MLS antibiotic, and the other with an inhibitor of RNA methylation. An increased clear zone will be observed where the antibiotic and second agent interact to exert their combined effect.

2. Checkerboard Method

The checkerboard (or chessboard) method may also be used to assess antimicrobial combinations. The term "checkerboard" refers to the pattern (of tubes or microtiter wells) formed by multiple dilutions of the two antimicrobials being tested in concentrations equal to, above, and below their minimal inhibitory concentrations (MICs). Also included is a row (or column) of tubes (or microtiter wells) without any antimicrobial for each drug. Thus, (compound A), being diluted along the x-axis, and (compound B), being diluted on the y-axis, results in squares on a checkerboard containing a unique combination of the two compounds being tested.

This technique may be performed with liquid or semisolid (agar) media, with microtiter trays rather than racks or test tubes, using other than 2-fold dilutions, using more than two drugs, and with organisms other than bacteria. In the agar dilution method, the principle of the technique is the same, but it is adapted for use in an agar dilution system, which is advantageous when a large number of strains are to be tested against a limited number of antibiotic combinations. Microtiter trays are often preferred because they are less cumbersome and require smaller quantities of antimicrobials and broth.

After conducting a checkerboard analysis, an isobologram is constructed as follows: For each concentration along the x-axis (plotted as the x-coordinate), the lowest concentration of the compound diluted along the y-axis that inhibits growth in the column of tubes is taken as the y-coordinate of this plot. An isobologram is constructed by connecting the series of coordinate points generated for each drug combination.

In interpreting the results, the critical question is usually whether an apparently synergistic combination is significantly below the additive line of the isobologram. Because the margin of error in these studies is ±1 dilution, a combination should be at least 2 dilutions below the additive line of the isobologram to be significantly synergistic, or at least 2 dilutions above the additive line to be significantly antagonistic.

3. Killing curves

Killing curves (time-kill curves, time-kill plots) may also be used. In contrast to the checkerboard, which typically provides only inhibitory data, the killing curve technique measures the microbicidal activity of the combination being tested. For this reason, it is advantageous for clinical situations in which bactericidal therapy is desirable. The other major advantage of killing curves over the checkerboard is that they provide a dynamic picture of antimicrobial action and interaction over time (based on serial colony counts), as opposed to the checkerboard, which is usually examined only once (after 16 to 24 hours or incubation).

When the colony counts in a killing curve study have been determined, the result are plotted and interpreted by the effect of the combination in comparison with the most active single drug alone. Results from bacteriostatic tests are interpreted as follows: Drug combinations are considered synergistic if inhibition occurs with concentrations at or below the curve described by the original MIC of each single drug and ¼ the MIC for both drugs. When an organism is sensitive to the combination at concentrations $\geq 2\times$ the original MIC of each single agent, the antibacterials are designated "antagonistic." The points that fall between synergy and antagonism are defined as additive or "indifferent."

4. Serum Bactericidal Testing

The serum bactericidal titer may be determined and used as an estimate of the activity of antimicrobial combinations in patients receiving them. The advantage of this approach is that it measures the activity of antimicrobial concentrations that are achievable in vivo.

5. Kinetic Spectrophotometric Methods

Spectrophotometric methods provide both a more kinetic view of antimicrobial interaction and a more quantitative analysis of the dose-response relationship. In these methods, one can plot growth curves for multiple cultures simultaneously and examine the effects of different antimicrobials and antimicrobial combinations on the growth-rate constants of those cultures. The expected 50% inhibitory concentration ($ED_{50}$) of one compound can be compared to that in combination with a steadily increasing series of concentrations of a second compound.

6. Paper Strip Diffusion

In the paper strip diffusion method, using cellophane or membrane filter transfer, filter paper strips are soaked in antimicrobial solution and placed at right angles to one another on an agar plate. After incubation, the filter paper strips are removed, leaving behind the compounds that have diffused into the agar medium. Following removal of the filter paper strips, a transferable material (cellophane or a filter membrane) that will permit diffusion of the two compounds now contained on the agar plate is placed on the agar surface and inoculated with a suspension of the organism to be tested. After incubation, the transferable material is removed from the agar plate containing the compounds and transferred to another agar plate without antimicrobials. Following an additional incubation, the growth pattern is examined.

Additive or indifferent combinations show no enhancement of their zones of inhibition at the former junction of the filter papers. Synergistic combinations show enhanced inhibition and may even demonstrate activity at this point, even when the organism is resistant to both compounds separately.

The methods of sections 2–6 above are even more fully described in Lorian (1991, pages 432–449).

7. Animal Tests for Activity and Toxicity

In vitro tests are useful as the starting point in the development of new drugs and combinations for use in treatment. However, no such drug or combination of agents should then be administered to a human patient solely on the basis of in vitro activity. This invention provides inhibitory compounds for use in combination with antimicrobials, which compounds have been selected on the basis of reported functional characteristics. As no such inhibitory compound is selected randomly, it is expected that the correlation between in vitro and in vivo data will be high.

However, the correlation between the strength of the in vitro and in vivo activities of a compound may not be linear. Therefore, certain compounds with high in vitro activity may not prove to be the most advantageous for in vivo use. This is not a drawback to the present invention, but simply reflects a checkpoint that is known to exist in all antimicrobial testing. Lorian (1991) pointed out that in vitro and in vivo tests differ in their general characteristics and specific variables. Consequently, discrepancies are likely to occur. However, they may be understood and interpreted correctly if the limitations of the test systems are understood.

As an example, Lorian (1991) discussed a case where discrepancies between in vitro and in vivo results could be resolved by using a concentration of drug in vivo that resulted in plasma levels of the antibiotic similar to those used in the in vitro evaluation. Thus, while in vitro evaluations such as those used by the inventors serve as an excellent indicator of in vivo antimicrobial potential, it is well understood in the art that optimizing an in vivo dose often takes more than a direct application of the in vitro data. Extrapolation of data to account for variable parameters such as blood volume, tissue accessibility and plasma half life is routinely practiced in the art.

Part of the practice of developing the in vitro data for in vivo clinical use involves studies in animal models. Lorian (1991) indicated that animal studies with antibiotics are important for suggesting appropriate indications, determining potential toxicity problems and providing insight into the pharmacokinetic properties of new agents in relation to those of known agents.

In evaluating any new antimicrobial or combination thereof, it is well known that the doses necessary to control the disease do not produce toxic reactions worse than those of the disease. Thus, the relationship between toxicity and efficacy must be ascertained. This relationship is known as the therapeutic index. The larger this index, the less likely it is that the drug or combination will cause toxic effects when used clinically. An index of 10 is often regarded as a safe minimum for an antibacterial, and this guideline can be used in the present invention in combination with the data given herein. In experimental studies, the index is usually calculated as the ratio of the dose that kills 50% of the animals ($LD_{50}$) to the dose that protects 50% of animals ($PD_{50}$).

In analyzing the amount of drug to be administered during animal tests, the maximum tolerated dose of a substance should be determined (using the most suitable route of administration). Before use in the treatment of infected animals, the maximum tolerated dose is determined by administering single injections of the substance to groups of animals by the oral, subcutaneous, or intraperitoneal routes. The animals are then observed for survival for periods of 24 hours to 7 days. Such acute toxicity studies establish for each route the 100% toxic dose ($LD_{100}$), the 50% lethal does ($LD_{50}$), and the maximum tolerated dose ($LD_0$) at which all animals survive. Experience has allowed the formulation of the rule that approximately ⅕ of the maximum tolerated dose of a substance will be tolerated when treatments are given once daily for 5 days or longer. For 1 to 3 days of treatment, ½ the maximum dose can usually be given.

In addition to obtaining initial information on toxicity, some information on absorbability may also be obtained. For example, if a substance is tolerated at 1000 mg/kg when given orally, but toxic when given at a dose of 50 mg/kg intraperitoneally or intravenously, the lack of toxicity by the oral route probably reflects poor oral absorption.

Interspecies variation in response to drugs is known to occur and this possibility must be considered when predicting the effect of the drug in man. If several species of animals are used for the toxicity studies, and the same toxic effects occur in all the species, then it is likely that these effects will also occur in man. Conversely, if no toxic effects are observed in any species of animal, except with unrealistic doses, then none are likely to occur with therapeutic doses used in man. The animals most commonly used in toxicity studies are the mouse, rat, rabbit, dog, and monkey. By utilizing animal models known in the art, as exemplified by those described herein, the combinations of the present invention can readily be developed for use in the clinical environment.

The inhibitors and antibiotic/inhibitor combinations identified by the inventors should therefore be evaluated in vivo in small animals in a fashion similar to that described by Lorian for new antibiotics (Lorian, 1991, pp. 746–786, incorporated herein by reference). It is important to note that since this invention generally concerns new and surprising combinations of known compounds, the testing needed will likely be less vigorous than that needed with a completely new drug. The toxicity data known for any individual drugs may be used as starting guidelines, and combined doses below such levels used in studies to confirm the advantages of the proposed combinations.

As described by Lorian (1991), animal models most frequently used in the evaluation of antibacterials may be categorized as basic screening, ex vivo, monoparametric, and discriminative. The ex vivo and monoparametric models are used to measure specific variables (e.g., dosage schedule, serum binding, or penetration into extravascular spaces). The discriminative systems are employed to differentiate the new agents from related or unrelated active agents. For preliminary evaluation of new agents and combinations, as in this invention, the basic screening system is usually employed.

Screening models involve simple one-step infections, simple techniques and schedules of treatment, short-duration experiments, reproducible courses of infection, simple evaluation (all-or-nothing models), economy of test drugs, and low costs. These requirements are best met by the mouse protection test, which is the most widely used in vivo screening model in antibacterial research. The mouse protection test is suitable for determining efficacy and toxicity of new antibacterials and it can indicate whether a drug or new combination is likely to be active orally or parenterally. The manner of conducting such tests will be well known to those of skill in the art in light of the present disclosure and the guidelines set forth below.

In a typical mouse protection test, the primary host used is the Swiss albino mouse. This is because there is a good correlation between clinical response to an antimicrobial and activity in the mouse; large numbers are easily obtained at relatively small cost per unit; and because an outbred strain of mice provides a heterogeneous population, which allows for immunological and other host factor variations.

In developing an experimental mouse model for in vivo testing, it is desirable to use human pathogens whenever possible. It is also desirable to infect with strains of microorganisms that are sufficiently virulent so that conditioning procedures to lower the host's resistance are unnecessary. When reproducible infections cannot be achieved by inoculation of the organisms alone, adjuvant stressing measures can be used to lower the host's resistance. In the case of injections with *Staphylococcus aureus*, a commonly employed measure is to suspend the organisms in 3 to 10% hog gastric mucin and to administer 0.5 ml amounts by the intraperitoneal route.

In preparing a new agent for testing, the stability, degree of solubility and/or the means by which a uniform suspension may be prepared should be considered. If the antibacterial is insoluble and is to be administered by the oral route, it will generally be prepared in a solution containing 1% carboxymethylcellulose. If an insoluble agent or combination is to be administered by the subcutaneous or intraperitoneal route, a suspension in water is prepared by sonication or homogenization. If these methods fail to produce a uniform suspension, the material is dissolved in DMSO or ethanol. The resulting solution is then diluted to a final concentration of less than 10% DMSO or ethanol, since higher concentrations of these solvents are lethal to mice. For treatment, antibacterials should be freshly prepared each day.

In order to obtain reproducible infections, it is necessary to determine the degree of virulence of each strain to be studied. The lowest dilution of the organisms at which all the animals die is defined as the minimum lethal dose (MLD). Alternatively, in place of MLD one can use multiples of the challenge dose of organisms that kills 50% of the animals ($LD_{50}$). After the animals are infected and treated, they are observed over a fixed period and the number of survivors is recorded. The 50% protective dose ($PD_{50}$) is calculated in mg/kg. The 50% protective dose is the same as the 50% curative dose ($CD_{50}$) or 50% effective dose ($ED_{50}$). By altering the treatment route or schedule, differences in activity can be demonstrated. In addition, the relative efficacy of oral and subcutaneous administration of a substance can be compared.

The mouse protection test has been studied in great detail, and evaluation of antibacterials using this method has produced a number of clinically effective agents (Grunberg & Cleeland, 1977). Various studies have shown that using the mouse protection test the $PD_{50}$ values generally fall into the same ranges as the clinical doses measured in mg/kg. However, this is not an indication that the doses in the mouse models should be exactly the doses employed in the clinical management of infections. Certainly humans are not treated on the basis of achieving only 50% survival. In spite of this, there is a reasonable overall correlation between the results obtained in the mouse model and clinical effectiveness.

Many agents that are not active against systemic infections are active against local infections when applied at the site of injection. Different techniques for producing local infections have been described, with the basic principle being the induction of a localized infection that is treated by application of the desired agent to the infected site. Antibiotics and combinations known to be inactive when given orally or subcutaneously have been shown to be active when infiltrated into the site of local infection, as exemplified by the activity of mycin against gram-positive organisms and two gram negative strains (Grunberg et al., 1967).

In the mouse protection tests described above, the infections are primarily of short duration, unnatural and overwhelming or self-limiting. A number of specific infections in a variety of animal hosts have been utilized to mimic human infections more precisely and will be known to those of skill in the art. Examples that appear to be reasonably faithful to the human infection are pyelonephritis in the rat and meningitis, endocarditis and osteomyelitis in the rabbit. In a number of other experimental infections, the targeting of infection to specific organs, while not as close in mimicking the human situation (e.g., meningitis and pneumonia in mice), provide useful models for predicting the selectivity of new agents and combinations.

The following is a description of certain exemplary discriminative animal models that may be of use in connection with the present invention. For most of the discriminative animal model systems it appears that the agents shown to be very effective experimentally are generally useful clinically (Ernst & Sande, 1981).

A simple model for the formation of intraperitoneal abscesses in mice is available that offers opportunities for studying various aspects of staphylococcal host-parasite interactions occurring in localized lesions. As an example of the formation of abscesses by anaerobes, a model of subcutaneous abscesses in mice caused by Bacteroides fragilis has also been described.

The thigh lesion model provides a nonlethal experimental infection to evaluate the effectiveness of an antimicrobial combination and allows the measurement of drug-pathogen interaction and drug pharmacokinetics in the infected host. If the animals are made neutropenic, then the thigh model becomes an excellent system for measuring the drug-microorganism interaction with most of the host defense system eliminated (Vogelman et al., 1988).

Regarding respiratory tract infections, such as pneumonia, various models are available. For example, in the mouse model of pneumonia, disease is induced in mice by intranasal instillation of 3 drops of an undiluted overnight culture of Streptococcus pneumoniae 6301 in trypticase soy broth containing 5% goat serum (Beskid et al., 1981). A useful model for the production of pneumococcal pneumonia in rats has been described by Ansfield et al. (1977). For the detection of antitubercular drugs, a number of mice systems have been described. An infection in guinea pigs useful for testing new antitubercular agents is also available. In this model. *M. tuberculosis* H37Rv, whether inoculated by the subcutaneous or intramuscular routes, produces a progressive, predictable disease.

Models for experimental acute urinary tract infections are commonly used to evaluate antibacterials. In mice, these infections produce either hematogenous or ascending infections, depending on whether the inoculum is administered intravenously or intravesically, with or without the addition of a foreign body. In the mouse pyelonephritis model, the infected animals, in most instances, either die or heal spontaneously. Consequently, treatment has to be started shortly after infection in order to alter the course of disease. For chronic pyelonephritis, agents are sought that will control the disease after the pathological damage has occurred. An infection in rats which stimulates chronic *E. coli* nephritis has been described in Ryan (1976).

A number of systems for studying the effect of antibacterials in experimentally induced meningitis have been reported. A simple lethal mouse model to produce pneumococcal meningitis is available (Tsai et al., 1975). For induction of meningitis, Swiss albino mice were subjected to strains of *S. pneumoniae* virulent for mice by the intraperitoneal route. A model for the induction of *H. influenzae* b meningitis in infant rats, which appears to be both simple and reproducible, has also been described. An excellent rabbit model used to study the activity of antibacterials in the therapy of experimental meningitis has been described using New Zealand white rabbits (Dacey & Sande, 1974; Scheld et al., 1978).

The method described by Garrison & Freedman (1970) for inducing experimental endocarditis in rabbits has been well studied and shown to be a reliable model for evaluation of the effectiveness of antibacterials. The rabbit model described by Norden (Norden, 1970) is a simple and reproducible system for the study of osteomyelitis. A rat model for simulating intraabdominal sepsis, either with known organisms or with mixed fecal flora cultures, has been developed by Onderdonk et al. (1974).

A simple model for keratitis and experimental deratitis in guinea pigs is available (Davis et al., 1977), as is a simple method to obtain reproducible intraocular infections in rabbits (Maylath & Leopold, 1955).

Models are even available for sexually transmitted diseases. Corbeil et al. (1979) have described a mouse model for disseminated gonococcal infections, using a gonococcal strain (N24) isolated from a human genital tract. The most successful model for studying gonococcal urethritis is produced by the inoculation of chimpanzees with human urethral exudate (Arka & Balows, 1986). Johnson et al. (1982) have described a method for experimentally inducing syphilis in rabbits.

Models of fungal infections are also available, e.g., for infection with fungi other than dermatophytes, intravenous injection of clinical specimens or culture isolates is used for the conversion of dimorphic fungi to the tissue phase. Overwhelming numbers of organisms are usually used, since such infections develop slowly and frequently are not fatal. An example of a non-fatal subcutaneous fungal infection model is that achieved by accomplishing a local infection with *C. albicans* in cortisone-preconditioned animals. Such models may be employed in the detection of topical antifungal agents and combinations.

Preferably, in the above models, animals infected with resistant microorganisms would be treated in at least two ways before progressing to clinical trials. In the first procedure, the infected animals will be treated with the inhibitor(s) for a predetermined time before the antibiotic(s) treatment is started. In a second procedure, the infected animals are treated with the antibiotic(s)/inhibitor(s) combination at the same time. In yet another procedure, the first regimen could be modified where the infected animals would be treated pre-treated with the inhibitor(s) alone, then followed by treatment with the combination of the antibiotic(s)/inhibitor(s).

EXAMPLE III

Methylation Inhibitors Increase Antibiotic Susceptibility

To show that compounds capable of directly or indirectly inhibiting methylation were able to increase the susceptibility of bacteria to MLS antibiotics, the inventors first used methods similar to the disk susceptibility test described in Example II.

In both of the following procedures, the protocol involved obtaining S. aureus lawn cultures in agar Petri-dishes. Freeze-dried S. aureus cultures from the ATCC [Strain 27660 (inducible resistant strain); strain 6538 (susceptible strain)] were reconstituted in 5 ml sterile broth media. Either Trypticase Soy Broth (TSB, Casein peptone 17 g, soya peptone 3 g, dipotassium phosphate 2.5 g, NaCl 5 g and dextrose 2,5 g, Lot X1582, Adams Scientific Inc., West Warwick, R.I.) or Brain Heart Infusion Broth (BHIB, Casein peptone 15 g, meat peptone/BHI solids 12 g, dipotassium phosphate, Dextrose 2.0 g, yeast extract 5.0 g and NaCl 5.5 g, Lot DM1082, Scott Laboratories Inc., West Warwick, R.I.) were used, at concentrations of 30 and 42 g/l respectively.

The inoculated broths were incubated for 24h at 37° C., when they were streaked out on appropriate agar plates to assess purity of culture. Either of 40 g/l BBL Trypticase Soy Agar (TSA, Pancreatic digest of casein 15 g, papaeic digest of soybean meal 5 g, NaCl, 5.0 g and agar 15 g, Lot K6DCXY, Becton and Dickenson, Cockeysville, Md.) or Brain Heart Infusion Agar (15 g/l Agar, Scot Scientific Inc. West Warwick, R.I., Lot C-0281 and 42g/l BHIB) were used.

In the first procedure, two BHIA agar plates (Falcon Petri-dish 50 mM, Becton Dickenson, Lincoln Park, N.Y.) were prepared, with an inhibitor mixed into one of the plates at the appropriate concentration. Both plates were inoculated with, e.g., a Staphylococci species resistant to erythromycin, using a sterile, aseptic wooden cotton swap containing about 0.2 ml of a $10^6$ organism/ml solution. Two disks, each impregnated with erythromycin (15 mg/disc; Remel, Lenexa, Kans.), are placed on each agar plate. The plates were incubated for 17–24 hours then the clear zones were analyzed.

Although BHIA contains about 3% protein in contrast to the 2% protein in TSA, it is suspected that TSA contains higher concentrations of methionine and/or growth factors that increase the robustness of S. aureus to erythromycin.

Figure 2:
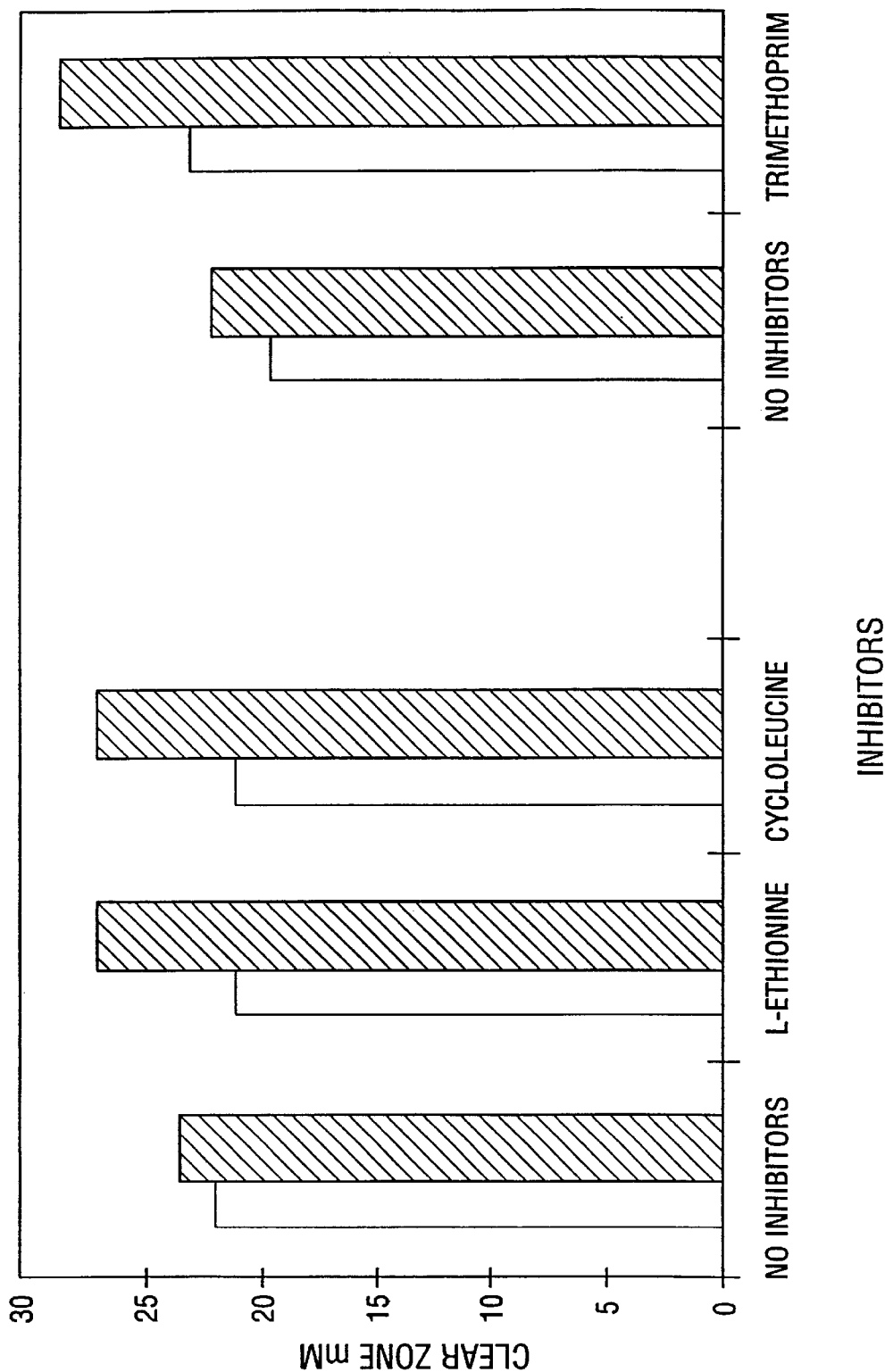
FIG 2. Erythromycin susceptibility for *Streptococcus aureus* 6538 (erythromycin susceptible) where ethionine, cycloleucine and trimethoprim are pre-mixed with brain heart infusion (BHIA, unshadowed columns) or trypticase soya agar (TSA, unshadowed columns).
Figure 3:
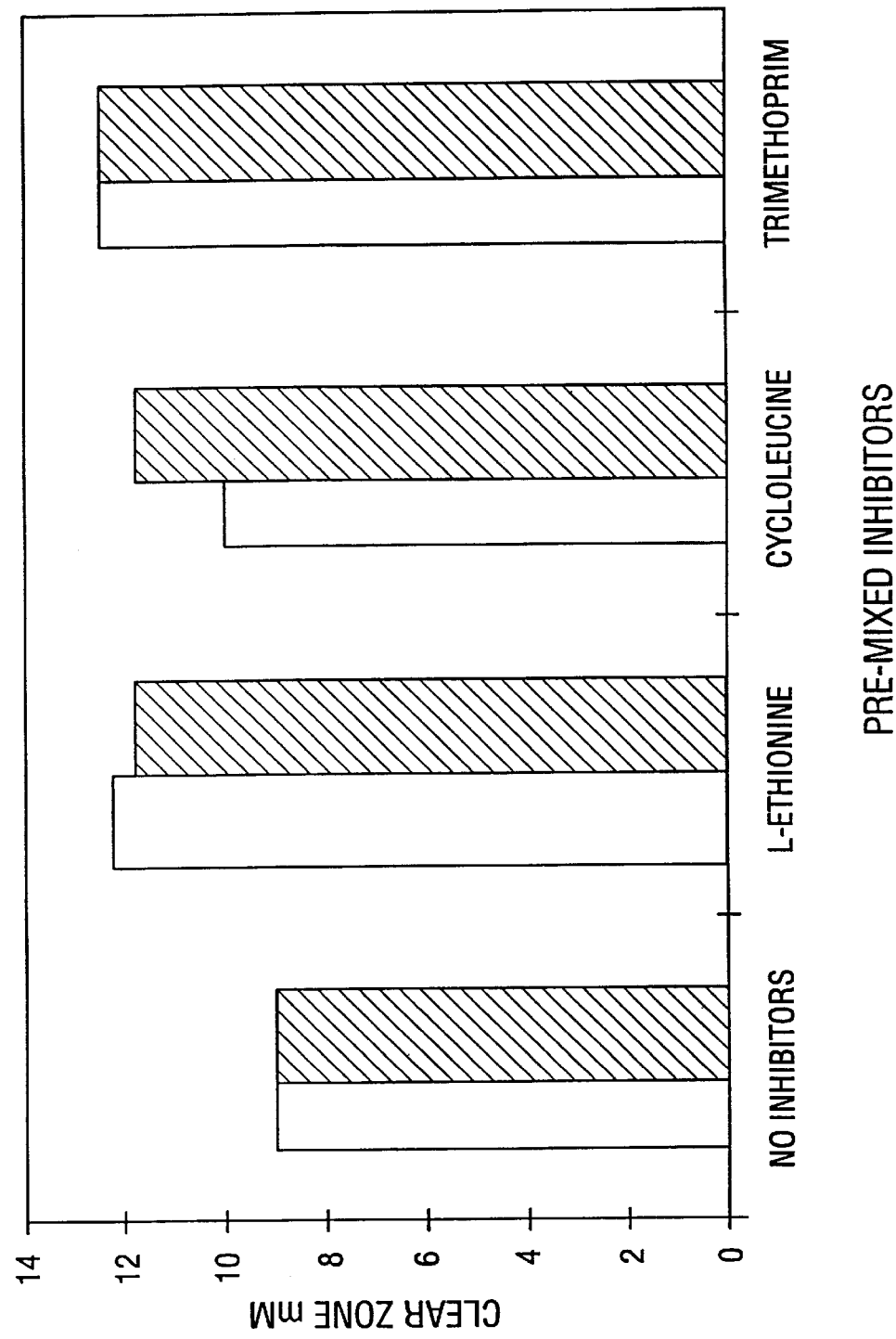
FIG. 3. Erythromycin susceptibility for *S. aureus* 27660 (erythromycin resistant), where ethionine, cycloleucine and trimethoprim are pre-mixed with BHIA or TSA.

FIG. 2 shows the results from one such study in which erythromycin susceptibility for Streptococcus aureus 6538 (erythromycin susceptible) was examined in the presence of erythromycin in combination with ethionine, cycloleucine and trimethoprim. FIG. 3 shows similar results but using the erythromycin resistant strain S. aureus 27660. Ethionine, cycloleucine and trimethoprim all result in an increase in the size of the clear zone.

In a second evaluation procedure, 100 mM Petri-dish agar plates (American Precision Plastic, North Geln, Co.) were prepared, as described in the first procedure, but this time with no inhibitor pre-mixed into the agar. Five discs containing 310 μg ethionine/disc containing disc were placed on the S. aureus (resistant) incubated BHIA agar plate at zero time. At times 0, 1, 2, 3, and 5 hours, each disc was then removed and replaced with an erythromycin disc at the identical position that the inhibitor disc had previously occupied. Erythromycin controls were included at each point.

Figure 4:
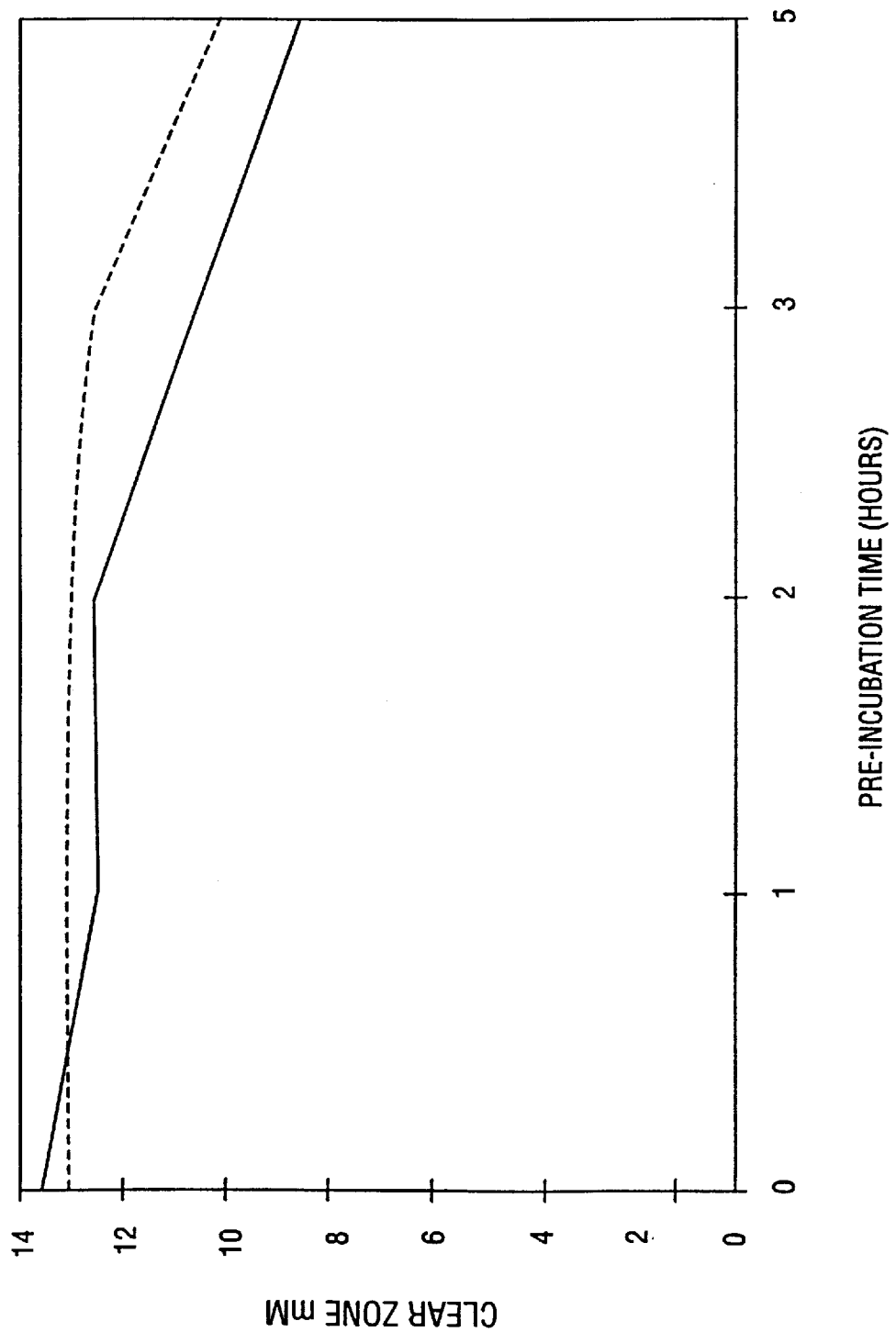
FIG. 4. Erythromycin disc-susceptibility for *S. aureus* 27660 (erythromycin resistant), pre-incubated with inhibitor-containing discs.

Increases in clear zones were observed after 18 hours incubation with inhibitor (ethionine)/erythromycin combination relative to erythromycin alone (FIG. 4). From these results it appears that pre-incubation with inhibitor for increased time periods increases the sensitivity of the resistant organisms to erythromycin. The inventors contemplate that using a broth susceptibility test will give a better evaluation of the effect of pre-incubation, which should show larger effects with inhibitors.

Using the first procedure described above, various other inhibitors were also tested. At concentrations of between 18 mM (for methotrexate) and 410 mM (for nicotinamide), all of the agents except SAH tested proved to increase the size of the clear zone (Table 8). The results are expressed in terms of relative effectiveness.

TABLE 8

ERYTHROMYCIN SUSCEPTIBILITY FOR S. AUREUS 27660

| Inhibitor | Concentration mM | Clear Zone mM | % Relative effectiveness[3] |
|---|---|---|---|
| Control | 0 | 10[2] | 100 |
| Methylthioadenosine | 42[1] | 12.5 | 183 |
| Nicotinamide | 410 | 12.5 | 183 |
| Na⁺Sulfadiazine | 56 | 12.5 | 183 |
| 3-Deazaneplanocin A | 31 | 12 | 167 |
| 2-Deoxyadenosine | 183 | 14 | 233 |
| DFMO | 46 | 14.5 | 250 |
| Ara-A | 39[1] | 12.8 | 193 |
| D,L-Buthionine-(S,R)-Sulfoximine | 90 | 12 | 167 |
| SIBA | 33[1] | 12.8 | 193 |
| Tubercidin | 34[1] | 12.8 | 193 |
| Methotrexate | 18 | 14 | 233 |
| S-Adenosylhomocysteine | 35[1] | 10 | 100 |
| 2-Chlorodeoxyadenosine | 35[1] | 12 | 167 |

[1]Contained 16% Dimethylformamide (DMF)
[2]Controls with and without DMF identical
[3]$[D_{mod} - D_{disc}]/[D_{Cont} - D_{Disc}] \times 100$ As shown in Table 8, with the great majority of the inhibitors, the bacterial lawn was observed to be substantially inhibited in comparison to the controls with no inhibitor. It is more than likely that SAH is not taken up by S. aureus. Walker & Duerre (1975) showed with studies in dogs that $^3$H-labeled SAH is not taken up and excreted unchanged in urine. There exists a high likelihood that a similar effect occurred in the present study with SAH.

Importantly, the inhibitors shown in Table 8 are generally representative of the different groups of inhibitors identified by the inventors, i.e., compounds capable of inhibiting RNA methyltransferases; SAH hydrolase; SAM synthetase (via inhibiting glutathione synthetase); dihydrofolate reductase (DHFR); and also, agents that inhibit polyamine synthesis.

It should be noted here that the inventors currently contemplate that the use of other analytical methods will allow the above enhancement data to be refined. This is because the disc testing protocol, while clearly very useful, is not considered by the inventors to be the optimal protocol for a quantitative type of study. As such, a broth culture procedure, where the organism is grown in the presence of both erythromycin and the inhibitor in liquid medium, is proposed. The growth of bacteria is then assessed photometrically (Example II). This procedure is contemplated to allow a better evaluation of the potency of the inhibitors.

As a reference point, it is important to note that erythromycin, as an example of an MLS antibiotic, is used clinically at an oral dose of 2000 mg/day (Reese & Betts, 1993). In vitro, in an agar disc susceptibility test, a $MIC_{90}$ (minimum inhibitory concentration for 90% inhibition) of about 4 µg/ml for *S. aureus* is typically determined, while the MIC in broth culture for the same organism is typically between 0.12 and 0.5 µg/ml (Weideman & Atkinson, 1991).

EXAMPLE IV

Inhibitors of Transmethylases
1. SAH and SAH Analogues

SAH hydrolase (SAHH) occurs in many procaryotic organisms (Shimizu et al., 1984). It is believed that SAHH plays an important role in many cells in removing SAH, a product of transmethylation reactions involving SAM (Thong et al., 1985). SAH is an inhibitor of most SAM-dependent transmethylase reactions, consequently inhibition of SAHH gives rise to higher concentrations of SAH which reduces the activity of the transmethylases.

Yebra et al. (1991) showed that SAH (100 µM) and sinefungin (50 µM) inhibit RNA methyltransferase from Streptomyces antibioticus by 97 and 96% respectively. From these results, the inventors estimated that SAH dosage ranges similar to that of sinefungin could be used clinically. Due to the membrane transport characteristics of SAH it is anticipated that the most advantageous method of SAH delivery will be as a liposome or nano particle (Couvreur et al., 1991; Example XIII). Since the net effect of SAHH inhibition is to raise the SAH concentration which causes the inhibition of transmethylation reactions, it is expected that SAH will be used alone or in combination with other methylation inhibitors. Doses useful in therapy with antibiotics, will be from about 1 mg/kg/day to about 100 mg/kg body weight/day, and preferably, from about 5 to about 50 mg/kg body weight/day.

Coward et al. (1974) reported that 2-fluoro-S-adenosylhomocysteine (2-FSAH) is an effective inhibitor of SAHH. Other structural analogues of SAH with modification in the amino acid, base or sugar portion of the molecule have been evaluated (Pugh & Bochardt, 1982) in vitro for their abilities to inhibit the SAM-dependent transmethylations catalyzed by vaccinia virion mRNA(guanine-7) methyltransferase and mRNA(nucleoside-2'-) methyltransferase. S-Tubercidinylhomocysteine (STH) was found to be a particularly potent inhibitor of (nucleoside-2')methyltransferase.

From the candidate inhibitors of vaccinia virion mRNA (guanine-7)methyltransferase evaluated at 100 µM, Pugh & Bochardt (1982) showed that S-adenosyl-L-homocysteine sulfoxide (47% inhibition), S-adenosyl-L-homocysteine sulfone (40%), S-($N^6$-methyladenosyl)-L-homocysteine (85%), S-(3-deazaadenosyl)-L-homocysteine (84%), and S-aristeromycinyl-L-homocysteine (66%), sinefungin (100%) and A9145c (100%) were the most potent analogs.

Gillet et al. (1979) also described a number of SAH analogues mainly modified in the amino acid portion of the molecule, that are all effective competitive inhibitors of protein methyltransferase II from human erythrocytes. From these analogues, the inventors propose that 5'-S-(3-carboxyl-4-nitrophenyl)thioadenosine, S-adenosyl-L-homocysteine sulfoxide and 5'-S-(methyl)-5'-S-(butyl) thioadenosine would be particularly useful in connection with this invention.

The following doses are proposed for use in killing bacteria, and other microorganisms, in combination with antimicrobial agents: between about 1 to about 200, and preferably, between about 10 to about 100 mg/kg body weight/day for 2-FSAH and S-aristeromycinyl-L-homocysteine (STH); between about 1 to about 200, and preferably, between about 10 to about 100 mg/kg body weight/day for S-Adenosyl-L-homocysteine sulfoxide and S-Adenosyl-L-homocysteine sulfone; and between about 1 to about 200, and preferably, between about 5 to about 75 mg/kg body weight/day for S-($N^6$-methyladenosyl)-L-homocysteine and S-(3-deazaadenosyl)-L-homocysteine.

2. Homocysteine

Homocysteine is mainly methylated by two different enzymes in the last step of the biosynthetic pathway in bacteria to form methionine, which is essential for the synthesis of SAM. The two enzymes are homocysteine methylase [EC 2.1.1.14; using $N^5$-methyl tetrahydropteroylglutamate (N>2) as methyl donor] and homocysteine methylase [EC 2.1.1.13; using vitamin B12 as methyl donor]. *E. coli*, as an example, contains both enzymes, whereas most organisms possess only one enzyme (Cohen & Saint-Girons, 1987). The inhibition of any of the biosynthetic reactions involved in the synthesis of homocysteine, is predicted by the inventors to inhibit transmethylation reactions since it increases the SAH/SAM ratio.

3. S-$N^6$-methyladenosylhomocysteine

S-$N^6$-methyladenosylhomocysteine is nearly as potent an RNA methyltransferase inhibitor as SAH (Hoffman, 1978). Administration of $N^6$-methyladenosine has been proposed as a general method for blocking in vivo RNA methylation in studies to determine the role of methylation in RNA processing and translational function. S-$N^6$-methyladenosylhomocysteine may be synthesized in vitro from $N^6$-methyladenosine and homocysteine in a reaction catalyzed by S-adenosylhomocysteine hydrolase.

S-$N^6$-methyladenosylhomocysteine is commercially available from Sigma Chemical Company and may be used, in combination with an antimicrobial agent at doses of between about 1 to about 100 mg and preferably, between about 5 to about 50 mg/kg body weight/day.

4. Analogues of S-Aristeromycinyl-L-Homocysteine

A series of base- and amino acid modified analogues of S-aristeromycinyl-L-homocysteine, a carbocyclic nucleoside, were synthesized and evaluated as inhibitors of SAM-dependent methyltransferases (Houston et al., 1985a). Houston et al. (1985a) observed that from the evaluated compounds S-aristeromycinyl-D-homocysteine and 3-deazaaristeromycinyl-D-homocysteine were particularly effective methylation inhibitors with $K_i$ of 10.4 and 20.5 µM, respectively, for phenylethanolamine N-methyltransferase.

These carbocyclic analogues are believed to be improved inhibitors in vivo as they will be more stable to metabolism than their ribosyl analogues (Houston et al., 1985a). Doses of between about 1 to about 100, and preferably, between about 5 to about 50 mg/kg body weight/day are proposed for these analogues in combination with antimicrobial agents such as MLS antibiotics.

5. Polyinosinate

Liau et al. (1973) have shown that polyinosinate inhibits transfer and ribosomal RNA (tRNA and rRNA) methylases. The mechanism of inhibition has been attributed to specific interactions between the single-stranded polyinosinate and the methylating enzymes. Methylases of individual bases were differentially affected by poly(I): inhibition of adenine methylases occurred to the greatest extent and guanine methylases to the least. Local administration of 12 μg/mouse of poly(I) every 12 hours for 15 consecutive doses has been reported to inhibit multiplication of *Mycobacterium leprae* in the footpad of mice (Levy & Merrigan, 1977).

Polyinosinate with molecular mass ranging from 5000–200,000 is preferred for use in the present invention. From the data of Liau et al. (1973) and Levy & Merrigan (1977), the inventors contemplate that concentrations of poly(I) useful in therapy with agents such as MLS antibiotics, will be from about 0.1 mg/kg/day to about 30 mg/kg/day, and preferably, from about 0.1 to about 10 mg/kg/day. Poly(I) has been proposed for use in cancer chemotherapy and is thus considered suitable for human administration. Polyinosinate is commercially available from P-L Biochemicals (Milwaukee, Wis.).

Poly(I) was also found to be particularly effective in combination with adenine and adenosine (Liau et al., 1973). Extending the above schemes, it is thus also contemplated that adenine or adenosine could be combined with poly(I), with the adenine or adenosine being in a dose of from about 1 to about 700 mg/kg/day, and preferably, of from about 1 to about 500 mg/kg body weight/day.

6. S-Tubercidinylhomocysteine (STH)

S-Tubercidinylhomocysteine (STH) has a stable ribose-purine bond and retains the inhibitory potency of SAH on tRNA methylases. The efficacy of STH parallels that of SAH. The synthesis of STH in particular is described in Coward et al. (1974) and its structure is depicted below:

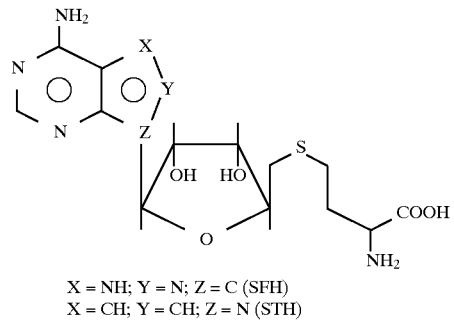

X = NH; Y = N; Z = C (SFH)
X = CH; Y = CH; Z = N (STH)

STH has been used to study the methylation of mRNA in vivo. Inhibition of cytoplasmic methylation of poly(A)-containing mRNA poly(A)-RNA methylation has been observed using a level of inhibitor that still permitted cell growth (Kaehler et al., 1977). The use of STH as a methylation inhibitor offers several advantages since it is able to permeate cell membranes, and is not susceptible to the nucleosidase enzymes responsible for SAH metabolism in mammalian cells.

Chang & Coward (1976) also synthesized SAH analogues in which the 5'-thioether linkage is replaced by an oxygen or nitrogen isostere. These compounds were designed to be resistant to enzyme-catalyzed hydrolytic cleavage of the 5'-substituent. Although these compounds showed lower inhibition of catechol O-methyltransferases, they are contemplated for use as inhibitors of rRNA methylases.

STH is proposed for use in killing microorganisms in combination with antimicrobials at doses of between about 1 to about 100, and preferably, between about 5 to about 50 mg/kg body weight/day; with the analogues described above being useful in the range of about 1 to about 100, and preferably, about 70 to about 75 mg/kg body weight/day.

7. SAM Analogues

The synthetic approach to stable nitrogen alkyl SAM analogues, in which the sulfur atom is replace by a nitrogen atom, has been described (Minnick & Kenyon, 1988). The procedures described have been used to prepare the methyl, ethyl, n-propyl, allyl, n-butyl, n-pentyl, n-octyl and 6-amino-1-hexyl nitrogen analogues of SAM. Testing one such nitrogen SAM analogue (in which R=Me in the structure below) with *E. coli* transfer RNA (uracyl-5)-methyl transferase has revealed that this compound functions as an inhibitor, but not as a methyl group donor (Minnick & Kenyon, 1988). The methyl analogue has been shown to have a $K_i$ of 9 μM for the *E. coli* methionine synthase.

It is expected that these derivatives will compete with all enzyme catalyzed reactions involving SAM. Such compounds, including the nitrogen analogues described below, are generally proposed for use in killing microorganisms in combination with antimicrobial agents, e.g., MLS antibiotics, at doses of between about 1 to about 100, and preferably, between about 5 to about 50 mg/kg body weight/day.

Analogues of SAM in which the sulfur atom is replaced by a nitrogen atom have the advantage that they will not be susceptible to decomposition reactions peculiar to SAM. The structures of such analogues are shown:

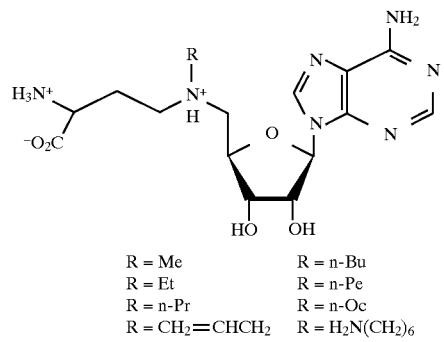

R = Me            R = n-Bu
R = Et            R = n-Pe
R = n-Pr          R = n-Oc
R = CH$_2$=CHCH$_2$    R = H$_2$N(CH$_2$)$_6$

8. Sulphonium SAM Derivatives

Zappia et al. (1969) described the preparation, purification, analysis of a variety of sulphonium derivatives of methionine. The methyl donor capacity of the inosine derivatives, and of decarboxylated S-adenosylmethionine, ranged between inactivity and effect equal to that of the biological methyl-donor SAM. In addition to SAH, these studies showed that S-inosyl-L-methionine, S-adenosyl-(5') -3-methylthio-propylamine, and 5'-(methylthio)adenosine were effective inhibitors.

The structures of active SAM sulphonium analogues are shown below. Such compounds, including the nitrogen analogues described below, are generally proposed for use in killing microorganisms in combination with, e.g., MLS antibiotics, at doses of between about 1 to about 150, and preferably, between about 5 to about 75 mg/kg body weight/day.

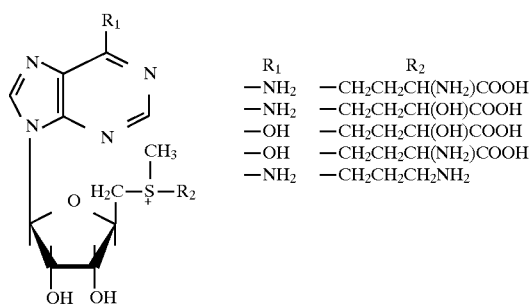

| R₁   | R₂                    |
|------|------------------------|
| —NH₂ | —CH₂CH₂CH(NH₂)COOH |
| —NH₂ | —CH₂CH₂CH(OH)COOH  |
| —OH  | —CH₂CH₂CH(OH)COOH  |
| —OH  | —CH₂CH₂CH(NH₂)COOH |
| —NH₂ | —CH₂CH₂CH₂NH₂      |

9. 5'-deoxy-5'-S-isobutyl-adenosine (SIBA)

5'-deoxy-5'-S-isobutyl-adenosine (SIBA) is known to be a competitive inhibitor of SAM and to strongly inhibit methylation in whole cells (Bona et al., 1976). SIBA inhibits the methylation of eukaryotic mRNA, especially that of the 5' cap, and it also affects various mRNA methylation to different extents (Jaquemont & Huppert, 1977).

SIBA also influences cell transformation by Rous sarcoma virus. Robert-Gero (1975) reported that adenosine homocysteine was less active as an inhibitor than its analogues and SIBA appeared to be the most potent among the latter at concentrations that were not toxic to normal cells.

SIBA has a structure as shown below, and position 2 is commercially available from Sigma Chemical Company.

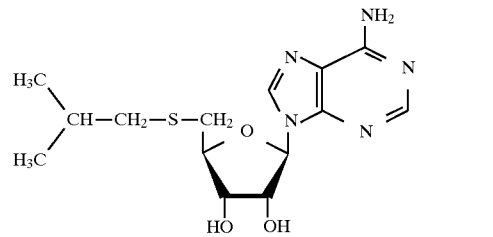

From established data, such as that from Jacquemont & Huppert (1977) showing that RNA methylation is inhibited ~65% by 1 mM SIBA, the inventors contemplate that therapeutically useful antibacterial concentrations of SIBA, when present with an antimicrobial agent, such as an MLS antibiotic, will be from about 1 to about 100 mg/kg body weight/day, and preferably, from about 10 to about 40 mg/kg body weight/day.

SIBA (0.033M) was evaluated by the inventors and shown to enhance the relative activity of erythromycin against *S. aureus* 27660 by 193% (Table 8).

10. Sinefungin and A9145c

Sinefungin is an antifungal antibiotic isolated from cultures of *Streptomyces griseolus* (Vedel & Robert-Gero, 1981). Sinefungin very strongly inhibits the methylation of G in position 2 and 7, and that of A in position 1 and 6.

Sinefungin and a related metabolite, A9145C, were also found to be potent inhibitors of Newcastle disease virion mRNA- and vaccinia virion mRNA(guanine-7-)methyltransferase and vaccinia virion mRNA(nucleoside-2'-)-methyltransferase. Sinefungin and A9145C were tested as inhibitors of these methylases and both were found to be extremely active. At drug concentration of 10 μM, where significant inhibition of virion plaque formation was observed, no cellular toxicity was detected. Although, at higher concentrations of sinefungin and A9145C, significant cellular toxicity was observed (Pugh et al., 1978), it has now been shown by Lemeteil et al. (1993) that sinefungin could be used in a rat model against *Cryptosporidium parvum* at a dosage of 10 mg/kg/day. Additionally, Avila et al. (1990) reported the optimum dosage using a mice model for cutaneous Leishmaniasis was 4 mg/kg/day, 50 times lower than the $LD_{50}$.

Yebra et al. (1991) also showed that sinefungin and derivatives strongly inhibit RNA methyltransferases from *Streptomyces* (*S. antibioticus, S. incarnatus, S. griseolus*. Additionally it was shown that sinefungin and its analogues inhibit both RNA and DNA methyltransferases from these organism. *S. antibioticus* methyltransferase is inhibited at the 100 μM level by A9145C (95%), cyclosinefungin (50%), SIBA 55%, ISOSIBA (52%) and 5'-S-methylthiomethyladenosine (65%). These results are in agreement with Li et al. (1985), who showed that sinefungin inhibits methylation of rRNA in *S.cerevisiae* and leads to a decrease in stable 18S rRNA. It is therefore expected that sinefungin and its analogues will function well with antibiotics and antimicrobials as claimed in the invention.

Sinefungin is commercially available from Sigma Chemical Company. The structure of sinefungin, in relation to that of SAH, is shown below.

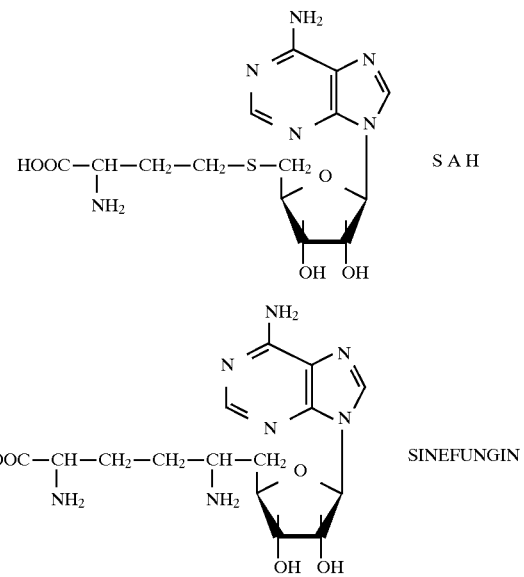

The synthesis of sinefungin has been reported by Barton et al., (1991) which allows modifications of the base portion of sinefungin to be prepared. Uracil analogues of sinefungin have also been prepared from uridine and L-aspartic acid (Barton et al., 1992), but are generally believed to have decreased inhibitory activity.

Based on the reports of Lemeteil et al. (1993) and Avila et al. (1990), it is contemplated that sinefungin concentrations of between about 0.1 and about 150 mg/kg body weight/day, and preferably, between about 1 to about 50 mg/kg body weight/day, may be used in combination with, e.g., MLS antibiotics, to kill bacteria.

11. Adenine Derivatives

Moore (1970) described the differential inhibition of tRNA methylases by adenine derivatives such as adenine, dimethylallyladenine, isopentenyladenosine, adenine phosphate, adenine sulfate, adenine-$N^1$-oxide, 6-methoxyadenine, 6-dimethyladenine, 6-methyladenine and 6-mercaptoadenine. It was found that all such compounds gave inhibition that would be acceptable for the purposes of the present invention, with the possible exceptions of 6-methoxyadenine and 6-dimethyladenine, and that dimethylallyladenine and isopentenyladenosine were particularly effective.

Therefore, adenine, adenine phosphate, adenine sulfate, adenine-$N^1$-oxide, 6-methyladenine and 6-mercaptoadenine may be used in combination with agents such as MLS antibiotics at doses of between about 10 to about 200, and preferably, between about 25 to about 100 mg/kg body weight/day; with dimethylallyladenine and isopentenyladenosine having proposed doses of between about 1 to about 100, and preferably, between about 10 to about 75 mg/kg body weight/day.

12. Nicotinamide

Swiatek et al. (1973) have shown that the inhibition of porcine liver tRNA methyltransferase activity by nicotinamide is due to an active methyltransferase enzyme that, in the presence of SAM and nicotinamide, produces 1-methylnicotinamide and SAH, the latter of which inhibits methyl transferase enzymes.

Nicotinamide (0.41M) was evaluated by the inventors with the first procedure and shown to enhance the relative activity of erythromycin against *S. aureus* 27660 by 183% (Table 8). The sc. $LD_{50}$ of nicotinamide is 1.68g/kg in rats (Windholz et al., 1983). It is therefore proposed that dosage of 1 mg/kg to 1.5 g/kg/day in combination with, e.g., MLS antibiotics, will kill bacteria and other microbes, the preferred dosage being 100–1000 mg/kg/day.

13. Methinin

Methinin is a natural occurring methylation inhibitor that is isolatable from rat and that inhibits a number of methyltransferases. Methinin is a low molecular weight compound (1400) that has an active amine group and appears to be of a peptide nature (Lyon et al., 1987). It inhibits DNA methylation, and has potential for use with antimicrobial agents in the present invention.

14. 5'-Deoxy-5'-(methylthio)adenosine (MTA)

MTA is an inhibitor of several SAM-dependent methylations (Law et al., 1992) and, in addition, is also an inhibitor of spermine and spermidine synthesis (Yamanaka et al., 1987). Wolford et al. (1984) injected MTA in mice ip. for 28 days. Single injections of as high as 75 mg/kg were administered. The inventors suggest that MTA at dosages of 1 to 200 mg/kg, and preferably, of 10 to 75mg/kg/day, in combination with, e.g., MLS antibiotics, will be effective in killing microorganisms. MTA is commercially available from Sigma Chemical Company.

15. Xylosyladenine (9-B-D-xylofuranosyladenine)

Garrett & Kredich (1981) showed that xylosyladenine (9-B-D-xylofuranosyladenine) caused marked inhibition of RNA methylation and showed that methyluridine, 2'-O-methylcytidine, 5-methyluridine and 5-methylcytidine formation in RNA was reduced. DNA methylation was not inhibited. From data such as this, it is proposed that xylosyladenine and other xylofuranosyl analogues of SAM or SAH, can be used with antimicrobial agents for killing microorganisms in doses of between about 0.1 to about 150 mg/kg body weight/day, and preferably, of between about 10 to about 40 mg/kg body weight/day.

EXAMPLE V

Inhibitors of SAH Hydrolase (SAHH)

1. Certain Adenosine Analogues

S-adenosyl-L-homocysteine (SAH) hydrolase (SAHH) has been proposed as a target for antiviral agents (Wolfe & Borchardt, 1991). A good correlation exists between antiviral activity and SAHH inhibition. De Clercq & Cools (1989) observed a linear relationship between $IC_{50}$ (concentration that inhibits replication by 50%) for a series of adenosine analogues and their $logK_i$ values for inhibition of murine L929 cell SAHH.

The following compounds have been described as first generation broad-spectrum antiviral agents: 9(S)-(2,3-dihydroxypropyl)adenine [(S)-DHPA], D-eritadine, (R,S)-3-adenine-9-yl-2-hydroxypropanoic acid [(R,S)-AHPA], adenosine (Ado) dialdehyde, 3-deazaadenosine ($c^3$-Ado), aristeromycin (Ari) and neplanocin A (NPA or NpcA) (De Clercq & Cools, 1985; 1989), the structures of which are shown below.

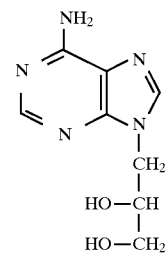

(S)-DHPA

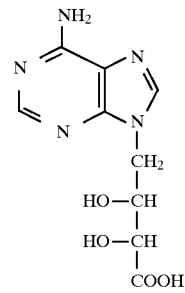

D-Eritadenine

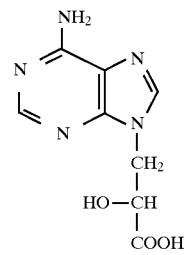

(RS)-AHPA

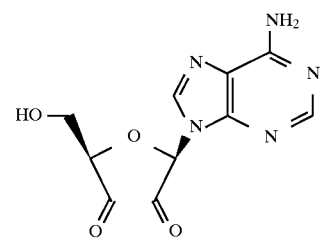

Ado dialdehyde

-continued

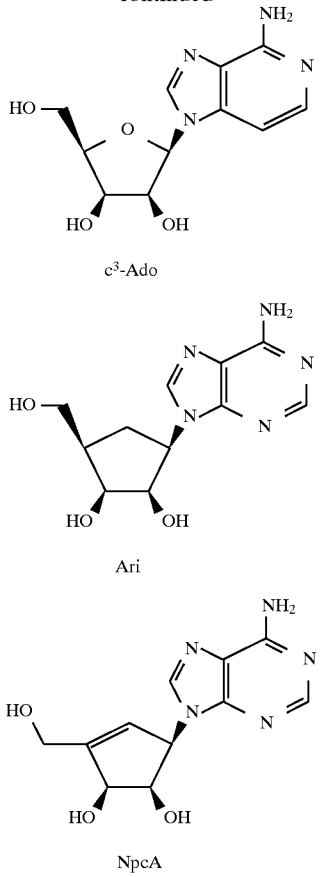

c³-Ado

Ari

NpcA

De Clercq & Cools (1989) also indicated that although these compounds are potent SAHH inhibitors, the cytotoxicity of these compounds may preclude clinical use as antiviral agents. However, since the $ID_{50}/IC_{50}$ required in the antibacterial case is contemplated to be less stringent than that required for an antiviral agent, the inventors contemplate that such first generation compounds may be effectively used in the present invention at concentrations that are not cytotoxic. Additionally, these compounds could be used with inhibitors of adenosine kinase and adenosine deaminase (Wolfe & Bochardt, 1991) to reduce toxicity.

The $ID_{50}/IC_{50}$ ratio required for safe clinical use of the proposed inhibitor combinations with antimicrobial agents, such as MLS antibiotics, is assessed by determining the $ID_{50}$ and $IC_{50}$ experimentally using mice or rats. The $ID_{50}$ and $IC_{50}$ values are determined as described, e.g., by Cleeland & Squires (1991) and Klaassen (1990).

As shown by Wolfe and bochardt (1991), SAH/SAM ratio ranges associated with therapeutic effectiveness ($IC_{50}$) and cytotoxicity ($ID_{50}$) can be determined, e.g., using HPLC. The concentrations of candidate inhibitors used clinically in combination with antibiotics will be determined using the $IC_{50}$, $ID_{50}$ and SAH/SAM ratios as determined above. Such concentrations are currently contemplated to lie in the general ranges stated below.

The activity spectrum of (D)-eritadine is similar to that of (S)-DPHA (Schanche et al., 1984). D-eritadine, L-eritadenine and L-threo-eritadenine inactivate SAH in hepatocytes. Proposed doses for use in microbial killing, when combined with, e.g., MLS antibiotics, of between about 1 to about 100 mg/kg body weight/day), and preferably of between about 10 to about 75 mg/kg body weight/day, are proposed for the eritadenine derivatives.

De Clercq & Cools (1985) reported the inhibition of SAH hydrolase by the following compounds at the stated concentrations: (S)-DPHA (Ki=1.4 μM); (RS)-AHPA (Ki=0.073 μM), carbocyclic 3-deazaadenosine (Ki=0.013 μM) and NPA (Ki=0.002 μM). Kitaoka et al. (1986) also showed inhibition and Backlund et al. (1986) showed that N- and O-methylation of mRNA was inhibited between 31–83% by 100 μM 3-deazaadenosine.

Since De Clercq & Cools (1985) demonstrated a correlation between the SAH inhibition potency and their antiviral potencies, it is expected that similar effects will be seen on the inhibition of rRNA methylation by these compounds. Also, as (S)DHPA, (R,S)-AHPA isobutylester, carbocyclic-3-deazaadenosine (C-c³Ado) and NPA reduce vesicular stomatitis virus-induced cytopathogenicity by 50% in primary rabbit kidney cells, with minimum inhibitor concentration of 20, 2, 0.2, 0.018 μg/ml, respectively, it is further proposed that such compounds will operate as methylation inhibitors at similar ratios.

Kitaoka et al. (1986) studied several nucleoside analogues known to have broad spectrum antiviral activity, e.g., ribavirin, vidarabine (Ara A), pyraazofurin, tubercidin, carbodine, [(S)-DHPA], (C-c³Ado), [(RS)-AHPA] isobutyl ester and neplanocin A. These compared for their potency and selectivity as inhibitors of human retrovirus replication in vitro. These adenosine analogues were proposed to also owe their antiviral activity to the inhibition of SAH hydrolase. The studies of Kitaoka et al. (1986), reported effective inhibitory concentrations of (S)-DPHA, C-C³Ado, (RS)-AHPA isobutyl ester and NPA are about 60, 1.4, 1.2 and 0.2 μg/ml, respectively. In vitro cytotoxicity indicated an activity index of >3, 70. 80 and >20 respectively for (S)-DPHA), C-C³Ado, (RS)-AHPA isobutyl ester and NPA, suggesting a potential for in vivo use.

The inventors have translated the above information into proposed doses for use in killing microorganisms, when combined with, e.g., MLS antibiotics, of between about 0.1 to about 100 mg/kg body weight/day, and preferably, of between about 0.1 to about 30 mg/kg/day for (S)-DPHA, C-C³Ado, (RS)-AHPA, Ari and NPA.

Wolfe and Borchardt (1991) also described second generation SAHH hydrolase inhibitors that have retained antiviral activity and considerably lower cytotoxicity than their parent first generation inhibitors. These compounds include: dihydroxycyclopentenyladenine (DHCeA) and dihydroxycyclopentenyl-3-deazaadenine (c³-DHCeA); dihydroxycyclopentanyladenine (DHCaA) and dihydroxycyclopentanyl-3-deazaadenine (c³-DHCaA); 3-deazaneplanocin A(c³-NpcA) and 3-deazaaristeromycin (c³-Ari), as shown below.

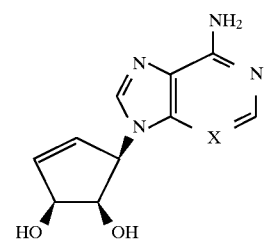

DHCeA: X = N
c³-DHCeA: X = CH

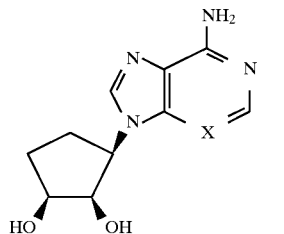

DHCaA: X = N
c³-DHCaA: X = CH

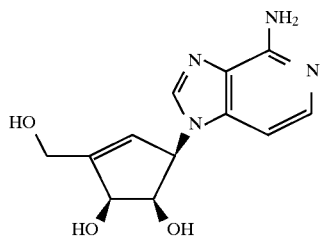

c³-NpcA

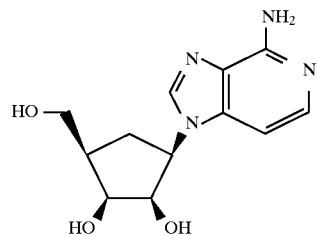

Ari

The increased therapeutic effectiveness of the second generation inhibitors (ratio of $ID_{50}/IC_{50}$) is apparently due to the elimination of adenosine kinase and adenosine deaminase activity of these generation compounds. It is contemplated that the second generation inhibitors will function successfully in clinical combinations with antimicrobial agents, as exemplified by MLS antibiotics. The safe clinical dose for the second generation inhibitors, when used in combination with, e.g., MLS antibiotics, will be higher than for the first generation inhibitors.

Using published information, such as that in De Clerq et al. (1989), the following doses are contemplated for using the second generation compounds in combination with antibiotics to achieve microbial killing: between about 0.1 and about 100; preferably, between about 0.1 and about 50; and most preferably, between about 0.1 and about 10 mg/kg body weight/day for DHCeA, c³-DHCeA, DHCaA, c³-DHCaA, A(c³-NpcA) and c³-Ari.

2'-deoxy-2'-chloroadenosine (CLA) was shown to be an inhibitor of hamster and human liver SAHH (Kim et al., 1985). Buckle et al. (1981) evaluated CLA at dosages of 300 μMol/kg (90 mg/kg) in mice. Based on these observations, it is proposed that CLA in combination with, e.g., MLS antibiotics, will provide enhanced killing at dosages between 1 and 150 mg/kg/day, and preferably, at between 10–90 mg/kg/day.

Methylthioadenosine (MTA, 0.042M) and 2-Chlorodeoxyadenosine (0.035M) were evaluated by the inventors with the first procedure and shown to enhance the relative activity of erythromycin against S. aureus 27660 by 183% and 163% respectively (Table 8). MTA is thus also proposed for clinical use with, e.g., MLS antibiotics, at dosages of between 1 and 150 mg/kg/day.

6-(γγ-Dimethylallylamino)purine riboside 1–200. 10–100 6-(γγ-Dimethylallylamino)purine riboside is commercially available from Sigma Chemical Company.

6-(Isopentenyl)adenosine 1–200. 10–100 6-(Isopentenyl) adenosine is commercially available from Sigma Chemical Company.

6-Dimethylaminopurine riboside 1–200. 10–100 6-Dimethylaminopurine riboside is commercially available from Sigma Chemical Company.

2. Neplanocin A (NPA)

Neplanocin A (NPA) is a cyclopentenyl analogue of adenosine that is a potent inhibitor of SAH hydrolase. NPA has been shown to inhibit vaccinia virus multiplication in mouse L929 cells. Concentrations of NPA as low as 0.5 and 1 μM in the culture medium have been reported to produce 84 and 95% inhibition of plaque formation, respectively, while exhibiting little toxicity to the host cells (Borchardt et al., 1984). This finding suggests that the antiviral action of this compound is related to an inhibition of SAM-dependent methylation reactions that are essential to the production of new viral particles (e.g. viral messenger RNA).

Yaginuma and colleagues reported that NPA possesses significant antitumor activity in vivo (Yaginuma et al., 1979; 1981; Tsujino et al., 1979). This indicates that NPA is safe for in vivo use.

Glazer & Knode (1984) also studied the activity of NPA against human colon carcinoma in vitro. They determined NPA to be an inhibitor of RNA methylation, but not of RNA synthesis (transcription). These properties confer to NPA unique pharmacological characteristics not possessed by other adenosine analogues studied at that time. Consequently, NPA should be a valuable tool for further chemotherapeutic studies.

NPA is available from the Toyo Jozo Co., Ltd., Japan and it may be synthesized according to the methods of Lim & Marquez (1983). From the studies showing that NPA inhibited malarial growth with $ED_{50}$ of 3 μM (Whaun et. al., 1986), and because NPA does not cause cellular toxicity ((Yaginuma et al., 1979; 1981; Tsujino et al., 1979), it is contemplated that useful concentrations of NPA for use in killing microorganisms (in combination with antimicrobial agents) will be from about 1 to about 50 mg/kg body weight/day, and preferably, from about 1 to about 20 mg/kg body weight/day.

The inventors make this proposal despite certain prior teachings concerning NPA. For example, Fischer et al. (1987) studied the effect of Neplanocin A on sixteen bacteria cultured on agar plates, and only two were determined to be sensitive. None of the sixteen showed any growth sensitivity in broth culture to concentrations as high as 4 mM (Fischer et al., 1987). The authors concluded that SAH as a target for antimicrobial agent development seemed not likely to be a productive approach (Fischer et al., 1987).

In marked contrast to the teachings represented by Fischer et al. (1987), the present inventors have unexpectedly found that several SAH inhibitors very similar to Neplanocin A were effective in enhancing the action of MLS antibiotics. In particular, Ara-A, 3-Deazaneplanocin A, methylthioadenosine and 2'-deoxyadenosine, used in combination with erythromycin, enhanced the killing of resistant S. aureus 27660 bacteria (Table 3).

3. 3-deazaneplanocin A (c³-NPA)

Tseng et al. (1989) described the synthesis of the neplanocin A analogue 3-deazaneplanocin A (also obtainable from Dr. V. E. Marguez; National Institutes of Health, Bethesda, Md.). This derivative is neither phosphorylated nor converted to the S-nucleosidylhomocysteine analogue and is therefore significantly less cytotoxic than neplanocin A. 3-deazaneplanocin A is thus contemplated to be one of the preferred compounds for use in combination with one or more MLS antibiotics or other antimicrobial agents.

Glazer et al. (1986) showed that NPA (10 μM), c³-NPA (10 μM) and c³-Ari (100 μM) inhibit the methylation of 28S rRNA, 18S rRNA and tRNA. Additionally it was shown that NPA, c³-NPA and c³-Ari showed cytotoxicity of HT-29 cells above 1, 100 and 250 μM, respectively. It is therefore expected that c³-NPA and c³-Ari could be used at dosages 10–100 times higher than that of NPA, i.e., used (in combination with antibiotics) at doses of from about 0.1 to about 1,000 mg/kg body weight/day, and preferably, from about 0.1 to about 200 mg/kg body weight/day.

As a practical matter, c³-NPA (0.031M; from Dr. V. E. Marguez) was evaluated by the inventors using the first disc susceptibility test, when it was shown to enhance the activity of erythromycin against *S. aureus* by 167% (Table 8).

4. Other Neplanocin A Analogues

Shuto et al. (1992) synthesized a number of 6'-modified Neplanocin A derivatives, which were evaluated for their SAHH and antiviral activities. Each of the compounds described were particularly active against a number of viruses. Additionally, they showed increased selectivity with 6'-C-methylneplanocin A surpassing neplanocin A both in antiviral potency and selectivity.

6'-C-methylneplanocin A, virtually resistant to adenosine deaminase and a good inhibitor of murine L929 SAHH, is expected to function extremely well in combination with MLS antibiotics. It is contemplated that this agent may be used in combination with, e.g., MLS antibiotics, at doses of from about 1 to about 200 mg/kg body weight/day, and preferably, from about 1 to about 100 mg/kg body weight/day.

5. Ara-A and Arabinoside Compounds

2'-Deoxyadenosine and 9-B-arabinofuranosyladenine (Ara-A) are suicide inactivators of SAH hydrolase (Hershfield, 1979; Helland & Ueland, 1982). Ara-A appears to be twice as active as 2'-deoxyadenosine. Ara-A is approved by the FDA for use as an ophthalmic ointment for herpes simplex virus infections and also as a systemic treatment for herpes simplex encephalitis at a dosage of 15 mg/kg/day for 10 days (Berkow et al., 1992). This suggested to the inventors that Ara-A could be used therapeutically.

Ara A (0.039M) and 2'-deoxyadenosine (0.183M) were evaluated by the inventors using the first disc susceptibility test:, and shown to enhance the relative erythromycin activity against the resistant *S. aureus* 27660 by 193 and 233% respectively (Table 8). The proposed dosages for Ara-A and 2'-deoxyadenosine clinical use range between about 1–300 mg/kg/day, and preferably, between about 1–100 mg/kg/day. $LD_{50}$ of Ara-A in mice is 4,677 mg/kg (i.p) and 7,950 mg/kg orally (Windholz et al., 1983).

Although Sacks et al. (1982) have suggested that the inactivation of SAH hydrolase could mediate toxic manifestations of ara-A therapy in certain group of patients, used at the appropriate therapeutic levels, Ara-A is contemplated to be an effective agent for combination with antibiotics. Both Ara-A and 2-Deoxyadenosine are commercially available from Sigma Chemical Company (St. Louis, Mo., USA) and Parke-Davis & Co. (Detroit).

6. Aristeromycin (9-β-{2,3-dihydroxy-4-(hydroxymethyl-cyclopentyl}adenine) and Analogues Houston et al. (1985b) synthesized a series of purine (adenine, N⁶-methyladenine, 8-azaadenine, 3-deazaadenine) carbocyclic nucleosides, nucleoside-2',3'-dialdehydes and nucleoside-2',3'-diols as potential inhibitors of SAHH and vaccinia virus replication. They observed a good correlation between a compound's inhibitory effect on SAHH and its antiviral effects, suggesting that viral inhibition is caused by the inhibition of a critical methylation step. Similar antimicrobial activity is expected from these compounds.

The most effective inhibitors of bovine liver SAHH from the synthesized series were evaluated at 0.2 mM Aristeromycin (99% inhibition), N⁶-methylaristeromycin (22%), 8-azaaristeromycin (46%;) and 3-deazaaristeromycin (97%). The inhibition of the corresponding dialdehyde derivatives at 0.2 mM ranged from 32 to 100%, while the corresponding diol derivatives showed between 82 to 98% inhibition only at the 2 mM level. The % inhibition of vaccinia plaque formation by the compounds above at the 10 μM level followed to a large extent the ability to inhibit SAHH. Similarly, (Keller & Borchardt, 1987) showed that the dialdehyde derivative produces an increase in intracellular levels of SAH and subsequent inhibition of SAM-dependent methylations.

(±)-5-Noraristeromycin and its 2,6-diamino-analogue were synthesized (Patil & Schneller, 1992; structures shown below) and shown to be inhibitors of SAHH. In antiviral evaluations it was observed that (±)-5-Noraristeromycin was 10 to 20 times less cytotoxic in cell culture. It is therefore expected that both these compounds will function well in combination with MLS antibiotics.

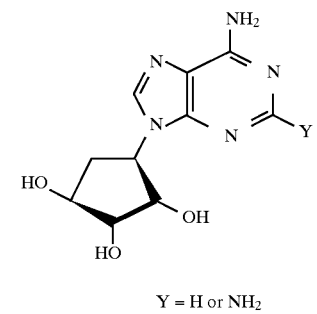

Y = H or NH₂

For aristeromycin and derivatives, the following doses are proposed for use in killing microorganisms in combination with antibiotics: between about 1 to about 200, and preferably, between about 10 to about 100 mg/kg body weight/day for aristeromycin, 3-deazaaristeromycin, (±)-5-Noraristeromycin and its 2,6-diamino-analogue; between about 1 to about 100, and preferably, between about 5 to about 50 mg/kg body weight/day for N⁶-methylaristeromycin; and between about 5 to about 200, and preferably, between about 10 to about 100 mg/kg body weight/day for 8-azaaristeromycin.

One of the cellular reactions affected by aristeromycin is transmethylation. Because of the sensitivity of the transmethylases to the S-aristeromycinyl analog of SAH, it is likely that the eukaryotic mRNAs or viral mRNA methyltransferases will be inhibited. Due to its cytotoxicity to mammalian cells, many derivatives have been synthesized to overcome toxicity. These include 2'-deoxy-, 3'-deoxy-, 3'-amino-3'-deoxy-, 3'-amino-3'-deoxyarabinofuranosyl, 6'-hydroxy, 6'-mercapto, 8'-bromo, 8-hydroxyaristeromycin, aristeromycin-3'-cyclic phosphate and aristeromycin-6'-cyclic phosphate. The appropriate doses for any given aristeromycin derivative will lie in the ranges described above, closest to the structural analogue which the derivative most closely resembles. Optimization of the dose will be routine given these guidelines.

The structure of aristeromycin is shown below, it is commercially available from Sigma Chemical Company.

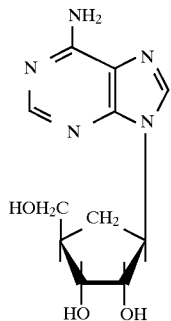

7. Tubercidin (7-deazaadenosine)

Enzymes that methylate tRNA are known to have qualitative and quantitative differences among different species. Inhibitors of these enzymes with three different specificities have been identified, namely some restricted bacterial enzymes, some to mammalian enzymes, and others with dual potencies (Wainfan & Borek, 1967). Adenine, adenosine, isopentenyladenosine and tubercidin are inhibitory to tRNA methylases isolated from E. coli and thus inhibit methylation.

As tubercidin inhibits SAHH, the SAH/SAM ratio increases and inhibits methylation. This is one instance of a compound that exerts an effect at various points in the cell. Tubercidin and isopentenyladenosine are commercially available from Sigma Chemical Company. Tubercidin has the following structure:

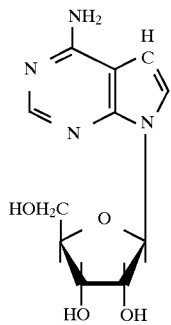

Tubercidin also inhibits rRNA processing in addition to methylation of tRNA and protein and nucleic acid synthesis. The substitution of tubercidin for adenosine in SAH yields a potent inhibitor of tRNA methylase, Catechol-O-methyltransferase, indole ethylamine N-methyltransferase, methylation of tRNA in phytohemagglutinin-stimulated lymphocytes and polyamine biosynthesis.

Tubercidin (0.034M) was evaluated by the inventors with the first procedure and shown to enhance the relative activity of erythromycin against S. aureus by 193% (Table 8). The $LD_{50}$ of tubercidin iv. in mice is 45 mg/kg (Windholz et al., 1983). Using this data, the inventors propose the following tubercidin dosage range for use with, e.g., MLS antibiotics, in killing bacteria: between about 0.1 to about 40, and preferably, between about 1 to about 20 mg/kg body weight/day.

EXAMPLE VI

Inhibitors of SAM Synthetase (SAMS)

1. Cycloleucine

Cycloleucine (1-aminocyclopentane-1-carboxylic acid) is an inhibitor of SAM synthetase (SAMS, or methionine-adenosyltransferase). Finkel & Groner (1983) reported that cycloleucine, at 0.5 mg/ml, causes more than a 30% decrease in internal $m^6A$ of late SV40 mRNA, with only a minor effect on the dimethyladenosine of the 5' cap structure. After treatment with 2 and 5 mg/ml cycloleucine, internal $m^6A$s were reduced by 10- and 100-fold, respectively.

Kroes et al. (1984) have shown that nitrous oxide and cycloleucine have synergistic growth inhibiting effects in experimental rat leukemia (BNML). These results indicated that a reduction of SAM synthesis by cycloleucine can increase the disturbance of folate metabolism that is caused by nitrous oxide, with a potentiation of the effects on leukemic growth.

Cycloleucine at a concentration of 0.1M, pre-mixed with Brain Heart Infusion Agar, showed improved killing (240% increase over control) of S. aureus resistant to erythromycin (FIG. 3). From the above inhibitory range of 0.5 to 5 mg/ml and the $LD_{50}$ of 309 mg/kg in mice (Windholz et al., 1983), it is contemplated that therapeutic cycloleucine doses of between about 1 and about 250 mg/kg body weight/day, and preferably, of between about 10 and about 50 mg/kg body weight/day, will be of use in combination with antibiotics to treat infections. Cycloleucine is commercially available from Sigma Chemical Company.

2. Methionine Analogues

Sufrin et al. (1979) reported that mono-, bi- and tri-cyclic amino acid structural and conformational analogues of L-methionine functioned as inhibitors of the enzymatic synthesis of S-adenosyl-L-methionine. These synthetic amino acids are structurally and conformationally related to cycloleucine (described above). Compounds that function as effective inhibitors include cyclopentaneglycine, the (1R, 2R,4S) isomer of 2-aminonorbornane-2-carboxylic acid, the (1R,2R,4S) isomer of 2-amino-5,6-exo-trimethylenenorbornane-2-carboxylic acid, 3-aminobicyclo[3.2.0]heptane-3-carboxylic acid and, most effective, (+)-2-aminobicyclo[2.1.1]hexane-2-carboxylic acid.

The concentration for 50% inhibition of these compounds are similar to that of cycloleucine. It is therefore expected that similar concentration as those contemplated for cycloleucine will be therapeutically active in combination with, e.g., MLS antibiotics.

Lombardini & Sufrin (1983) described the chemotherapeutic potential of methionine analogue inhibitors of tumor-derived methionine adenosyltransferases. In addition to cycloleucine, 1-aminocyclobutanecarboxylic acid, 1-aminocyclohexanecarboxylic acid, L-2-amino-4-hexanoic acid, (Z)-L-2-amino-5-chloro-trans-4-hexanoic acid, L-ethionine, and seleno-DL-ethionine were found to be effective inhibitors, with (+)-2-aminobicyclo[2.1.1]hexane-2-carboxylic acid again being found to be the most effective. Since the $I_{50}$ of these compound are similar to that of cycloleucine, similar therapeutic performance is expected.

Kramer et al. (1987) described the relative effects of SAM depletion on nucleic acid methylation and polyamine biosynthesis. It was shown that the treatment of cultured L1210 cells with 1 mM L-2-amino-4-methoxy-cis-but-3-enoic acid (L-cis-AMB), a methionine analogue inhibitor of SAM synthetase, produced a rapid and near-total depletion of SAM by 4 hours. Kramer et al. (1988) also reported that L-cis-AMB, the most potent methionine-analogue inhibitor of SAM synthetase at that time, is capable of rapidly depleting SAM pools in intact cells without affecting precursor incorporation into macromolecules.

Growth inhibition in L1210 cell culture cells by methionine analogue inhibitors of SAM biosynthesis in the absence of polyamine depletion has been reported by Porter et al. (1984). In addition to cycloleucine ($IC_{50}$=5 mM) and (+)-2-aminobicyclo[2.1.1]hexane-2-carboxylic acid ($IC_{50}$=5 mM), this group identified selenomethionine ($IC_{50}$32 0.13 mM) and L-cis-AMB ($IC_{50}$=0.4 mM) as effective inhibitors, with L-cis-AMB being more potent. The $IC_{50}$ of L-cis-AMB is about 10 fold lower than that of cycloleucine: it is therefore expected that it will operate therapeutically at lower concentration in combination with, e.g., MLS antibiotics.

Sufrin et al. (1993) later described the activity of L-2-amino-4-methylthio-cis-but-3-enoic acid (L-cisAMTB) as an inhibitor of SAM-synthetase. L-cis-AMTB was slightly less inhibitory than L-cis-AMB, but is nonetheless effective. The structures of L-cis-AMB and L-cis-AMTB are shown below:

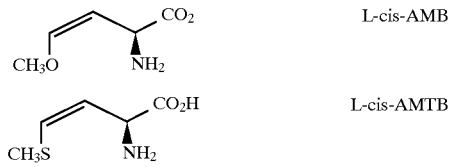

For the methionine analogues, it is contemplated that concentrations generally around 1–150 mg/kg body weight/day may be used in combination with antimicrobial agents to kill bacteria and other microbes. More specifically, for (+)-2-aminobicyclo[2.1.1]hexane-2-carboxylic acid, a preferred therapeutic dose of between about 10 and about 50 mg/kg body weight/day is proposed; and for L-cis-AMB, a therapeutic dose of between about 1 and about 100 mg/kg body weight/day, and preferably, of between about 5 and about 50 mg/kg body weight/day is contemplated.

3. ATP Analogues

Ma et al. (1990) described a family of ATP analogues that are either mono- or di-substituted with imido and methylene bridges in the polyphosphate chain: adenosine 5'-(αβ:β,γ-diimidotriphosphate) (AMPNPNP), adenosine 5'-(α,β:αβ',-diimidotriphosphate) (AMP(NP)$_2$), and adenosine 5'-(α,β:β,γ-dimethylenetriphosphate) (AMPCPCP). These were investigated as substrates and inhibitors of SAM synthetase. AMPNPP was found to be both a substrate for SAM synthetase and a potent inhibitor, with an inhibition constant 60 fold less than the $K_m$ of ATP. AMPNPP was about 1000-fold more effective as an inhibitor than AMPCPP.

The synthesis of AMPCPP and the other analogues is described in Ma et al. (1990), the structure of which is depicted below. Since the $K_i$ value for AMPCPP is similar to that of cycloleucine, equivalent therapeutic potency is expected.

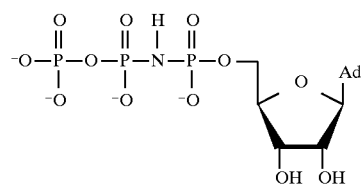

4. Further Inhibitors

Numerous inhibitors of SAM synthetase have been synthesized in the laboratory of Kappler. Their synthesis and biological activity have been reported in a number of papers (Kappler et al., 1986a; 1986b; 1987; 1988; Lim et al., 1986; Vrudhula et al., 1987; 1989).

Vrudhula et al. (1989) reported the synthesis of nonselective inhibitors of various isozymes of rat SAM synthetase. Four types of covalent methionine-ATP adducts were described to be potent inhibitors of the M-1 and M-2 isozymes. The most effective inhibitor is the 5'R epimer of a $CH_3$—C5'adduct of L-methionine and β,γ-imido-ATP. This compound, 5'(R)-(C)-[(L-homocysteine-S-yl)methyl] adenosine 5'-(β,γ-imidotriphosphate), is also described by Kappler et al. (1987).

5. Inhibitors of Glutathione Synthetase

Corrales et al. (1991) showed that there is a close correlation between the hepatic levels of glutathione and SAM synthetase activity. These authors suggested that under normal conditions, oxidation of cysteine groups of SAM synthetase may be protected by the intra-cellular levels of glutathione. The SAM-synthetase activity of animals treated with buthionine sulfoximine was shown to be only about 40% of that of untreated animals.

DL-buthionine-(S,R)-sulfoximine or L-buthionine(S,R)-sulfoximine used in most studies contains 4 or 2 isomers, respectively (Campbell et al., 1991). These authors showed that the different isomers were effective in reducing GSH levels in mice liver, kidney and pancreas at the concentrations of 0.2 and 0.4 mmol/kg respectively with L-buthionine-(S)-sulfoximine and L-buthionine-(S,R)-sulfoximine. L-buthionine-(R)-sulfoximine did not show any significant depletion of GSH at 0.2 mg/kg in liver or pancreas, but modest depletion in the kidney.

Lasierra et al. (1989) determined that buthionine sulfoximine [4.5 mmol/kg (1 g/kg) and diethyl maleate (3.2 mmol/kg) (0.55 g/kg)] ip. depleted liver and aortic glutathione in rabbits. Muzutani et al. (1994) suggested the use of buthionine sulfoximine could have application in tumor therapy.

As inhibitors of glutathione synthetase decrease the activity of SAM-synthetase, the present inventors thus propose the use of any glutathione synthetase inhibitors in combination with antibiotics. One such example is the buthionine sulfoximine mentioned above. Buthionine sulfoximine has the structure: $CH_3(CH_2)_2S$ (O)(=NH)$CH_2CH_2CH(NH_2)$ COOH, and is commercially available from Sigma Chemical Company.

Based on the in vivo data presented by Corrales et al. (1991), and on the fact that the GSH levels can be depleted in a dosage dependent fashion (Drew et al., 1984), the inventors contemplate that suitable therapeutic doses of buthionine sulfoximine will be between about 1 and about 1000 mg/kg body weight/day, and preferably, of between about 1 and about 100 mg/kg body weight/day. The inventors have shown that when L-buthionine(S,R)-sulfoximine (0.09M) was evaluated in a disc susceptibility assay it enhanced the relative activity of erythromycin against S. aureus by 167% (Table 8).

Many other examples of glutathione synthetase inhibitors have been described, any one or more of which may be used in connection with the present invention. Kato et al. (1987) showed sequence homology of over 40 amino acids between glutathione synthetase of *E. coli* and dihydrofolate reductase from *E. coli* and mammalian sources. It was shown that *E. coli* glutathione synthetase was potently inhibited by 7,8-dihydrofolate, methotrexate and trimethoprim. α-aminomethylglutarate was described by Sekura et al. (1976) as an inhibitor of glutathione synthetase. SAPH-3 disulfide was shown to be a potent inhibitor of glutathione synthetase (Schor et al., 1991). Suitable doses of 7,8-dihydrofolate, trimethoprim, α-aminomethylglutarate and SAPH-3, for use in combination with antibiotics, will generally be between about 0.1 and about 200 mg/kg body weight/day, and preferably, between about 1.0 and about 75 mg/kg body weight/day.

EXAMPLE VII

Inhibitors of Methionine Synthetase and Homocysteine Transmethylase

1. Nitrous Oxide ($N_2O$)

Yagiela (1991) reported that nitrous oxide reacts with the reduced form of vitamin $B_{12}$, consequently inhibiting methionine synthetase, an enzyme that directly supports methylation reaction and nucleic acid synthesis. $N_2O$ is commercially available from Aldrich Chemical Company, amongst other sources.

50% $N_2O$ is usually used clinically. However, evidence exists that prolonged exposure to clinical concentrations of $N_2O$ inhibits cellular proliferation and can lead to megaloblastic anemia, leukopenia, and thrombocytopenia (Yagiela, 1991). Continuous administration beyond 24 hours, or repeated administration more frequently than once every 3 to 4 days, should therefore be avoided to prevent leukopenia and megaloblastic changes. Biochemical recovery from exposure begins once inhalation is stopped, and can be improved by folinic acid and analogues, methionine and vitamin $B_{12}$. For example, Ostreicher (1994) recently reported that vitamin $B_{12}$ supplements reverse some of the effects of chronic $N_2O$ exposure.

It has been shown the certain bacteria, e.g., *Salmonella typhimurium* (Baden & Monk, 1981), *Streptococcus faecalis*, *E. coli*, and *S. aureus* are inhibited by $N_2O$ at elevated pressures. It is therefore expected that $N_2O$, at currently used clinical levels and durations (as above), in combination with, e.g., an MLS antibiotic, will show increase antimicrobial killing. Alternatively $N_2O$ may be used at elevated pressure in combination with antibiotics.

EXAMPLE VIII

Inhibitors of Adenosine Deaminase (ADA)

1. Coformycin and Isomers

Adenosine deaminase inhibitors are also known to inhibit methylation indirectly by increasing the concentration of SAH. Coformycin and its 2'-deoxy isomer are naturally occurring potent inhibitors of ADA. Two further, chemically synthesized inhibitors of ADA are 1, 6-dihydro-6-hydroxy-methylpurine nucleoside and erythro-9-(2-hydroxy-3-nonyl) adenine (Suhadolnik, 1979). These four ADA inhibitors are shown below:

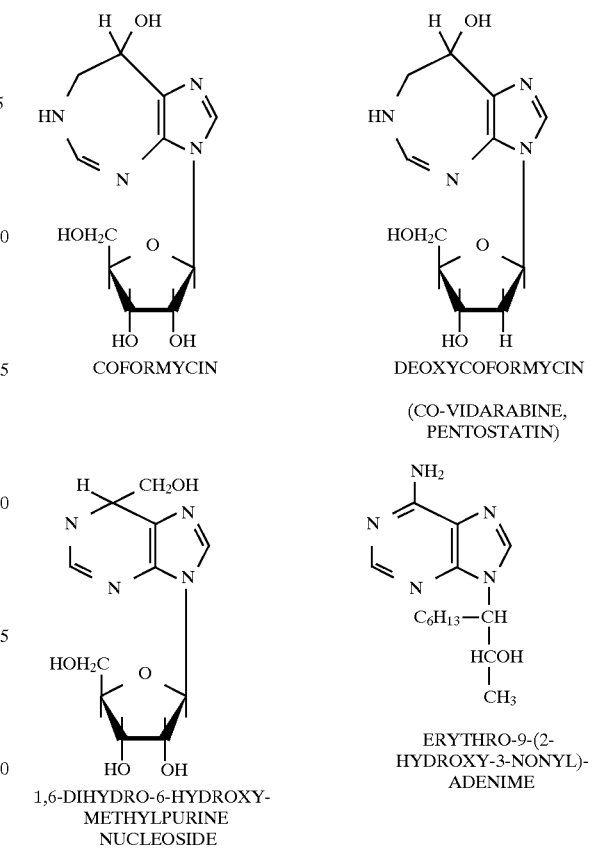

ADA inhibitors show anti-tumor and immunosuppression activities (Suhadolnik, 1979). Lindley & Pisoni (1993) showed that conformycin (2.5 mM), deoxyconformycin (0.02 mM), 2'-deoxyadenosine (2.5 mM), 6-methylaminopurine riboside (2.5 mM), 2'-3'-isopropylidene-adenosine (2.5 mM) and erythro-9-(2-hydroxy-3-nonyl)adenine (0.2 mM) inhibited lysosomal ADA by >97%. O'Dweyer et al. (1988) showed that 2'-deoxyconformycin (pentostatin), has striking antitumor activity. Pharmacological studies by these investigators led to the definition of a safe and effective low weekly dose, at which protracted ADA inhibition occurs in neoplastic cells. This dose is 0.13 mg/kg. They also reported that patients tolerated 1 mg/kg/day for 5 days with minimal distress. Brogden et al. (1993) determined the intravenous therapeutic dosage of pentostatin for lymphoblastic leukemia to be between 0.1 to 1 mg/kg/day.

Pentostatin has received FDA labeling approval for the treatment (3–6 month) of hairy cell leukemia in combination with alpha interferon (Kane et al., 1992). Based on these results, it is expected that dosages similar to the approved clinical dosages of pentostatin, namely 0.1 to 1 mg/kg/day, in combination with the antibiotics, will effectively kill bacteria.

EXAMPLE IX

Inhibitors of Dihydrofolate Reductase (DHFR)

1. Methotrexate (MTX)

Nesher et al. (1991) showed that, in vitro, low concentrations of methotrexate (MTX) interfere with specific methylation reactions in peripheral blood monocytes.

Svardal et al. (1988) suggested that MTX affects SAH metabolism in both cultured cells and patients and this may be explained by a lack of the 5-methyltetrahydrofolate required for salvage of SAH to methionine.

MTX is used clinically at dosages of either 2.5 to 5.0 mg/day or 25 to 50 mg/single dose/week (Berkow et al., 1992). It is proposed that MTX at such clinically relevant dosages in combination with antibiotics will kill bacteria. It was shown by the inventors that when MTX (0.018 mM) was evaluated with the first procedure it was shown to enhance the relative activity of erythromycin against *S. aureus* 27660 by 233% (Table 8).

It is also contemplated that aminopterin could be used similarly to MTX.

2. Trimethoprim

Roth (1986) indicated that trimethoprim, which retains only the 2,4-diaminopyrimidine moiety of MTX, retains high inhibitory activity only for bacterial DHFR. This inhibition therefore prevents tetrahydrofolate-dependent transmethylation reactions in bacteria (Schmidt et al., 1977), which is an important finding. From results such as these the inventors propose that trimethoprim and analogues could be used in combination with, e.g., MLS antibiotics, to kill bacteria. The typical clinical trimethoprim dosage is about 100 mg/12 hr (Berkow et al., 1992), and similar doses are proposed for use with the present invention. The inventors have shown in FIG. 3 that trimethoprim (0.26 mM) premixed with agar inhibits *S. aureus* 27660 (resistant strain) 275% relative to control.

3. 4,6-Diamino-2,2-dimethyl-s-triazines

Numerous 4,6-Diamino-2,2-dimethyl-s-triazines analogues have been synthesized especially in the laboratory of Baker (Baker & Vermeulen, 1969, 1970a, 1970b) and shown to be excellent inhibitors of DHFR. One such analogue was evaluated by Corbett et al. (1982) as being highly active against four transplantable colon adenocarcinomas in mice.

Based on these results it is expected that 3-chloro-4-{4-(2-chloro-4-[4,6-diamino-2,2-dimethyl-s-triazin-1(2H)-yl)] butyl}benzenesulfonyl chloride (NSC 127755, shown below) and 3-chloro-4-{4-(2-chloro-4-[4,6-diamino-2,2-dimethyl-s-triazin-1 (2H)-yl)phenoxy]methyl}-N,N-dimethylbenzamide (NSC 139105, shown below) in combination with antimicrobial agents such as MLS antibiotics will kill microorganisms. Since the s.c. toxicity in mice was determined as ≧156 mg/kg (LD$_{100}$), it is expected that NSC 127755 and analogues will be used at concentrations of about 1 to 100 mg/kg body weight and preferably at about 1 to 50 mg/kg.

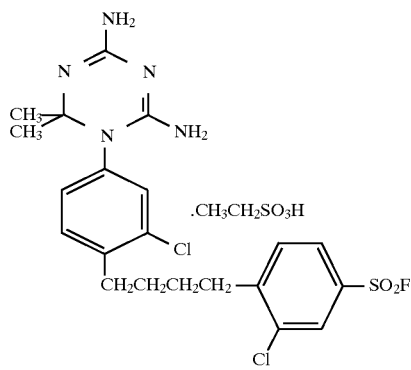

NSC 127755
TRIAZINE ANTIFOLATE

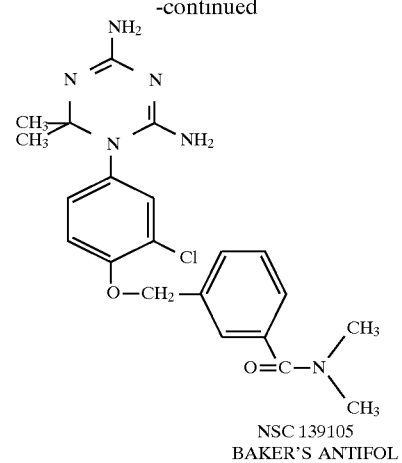

NSC 139105
BAKER'S ANTIFOL 4. 2,4-Diamino-5-(3,4-dichlorophenyl)pyrimidines

Baker & Vermeulen (1969; 1970b) also described inhibitors of this group. It is expected that inhibitors of this group in combination with MLS antibiotics will kill microorganisms at dosages similar to that of the 4,6-diamino-2,2-dimethyl-s-triazines described above.

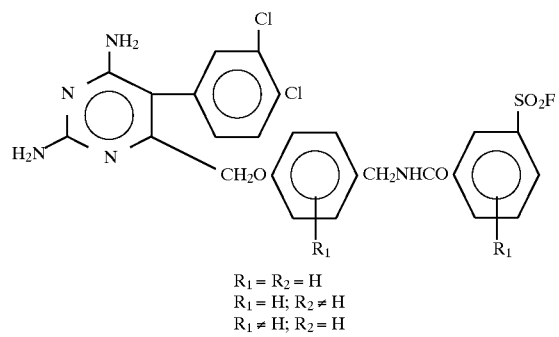

R$_1$ = R$_2$ = H
R$_1$ = H; R$_2$ ≠ H
R$_1$ ≠ H; R$_2$ = H

5. Further Inhibitors

Numerous inhibitors of DHFR are known in the literature (Roth, 1986; Bowden et al., 1993; Fleming & Schilsky, 1992). Blaney et al. (1984) reviewed over 1700 inhibitors of DHFR known at that time. To compare the inhibitors synthesized in numerous laboratories, these authors have reported the results in terms of either log 1/C or log K$_{iapp}$. The potency of inhibitors were calculated from reported I$_{50}$ or K$_i$ values and expressed as either log 1/C or log K$_{iapp}$. No distinction was made between these two parameters in this publication. The semi-quantitative nature of these parameters are suitable to indicate the approximate potency of the reported inhibitors. It is expected by the inventors that compounds with either a log 1/C or log K$_{iapp}$>3, and preferably >5, will work in combination with antibiotics to kill bacteria and microorganisms.

Such inhibitors are contemplated for use in combination with antibiotics at doses of between about 0.1 and about 200 mg/kg body weight/day, and preferably, between about 1 and about 100 mg/kg body weight/day.

6. Inhibitors of Dihydropteroate Synthetase: Sulfonamides

Bacteria cannot utilize preformed folic acid. Sulfonamides function as competitive inhibitors of p-aminobenzoic acid (PABA) incorporation into dihydropteroic acid, the immediate precursor of folic acid. Sensitive organisms are those that must synthesize their own folic acid. Mammalian cells are not effected since they required preformed folic acid. In addition, sulfonamides combine with the pteridine moiety to deplete the system of pteridine if PABA is not present (Madell & Sande, 1990). The structures of sulfanilamide, sulfadiazine, sulfamethoxazole, sulfisoxazole and sulfacetamide are shown below:

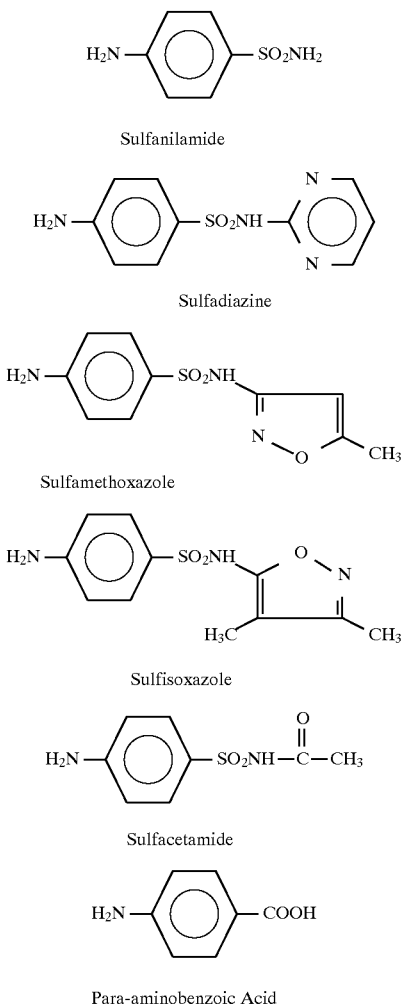

Clinical doses typically range from 2 to 8 g/day for sulfisoxazole as a typical example. Trimethoprim, a DHFR inhibitor is generally used in a combination with sulfamethoxazole, a dihydropteroate synthetase inhibitor. This combination is important clinically for a number of microorganisms and is used at dosages of about 800/160 mg/day (SMX/TMP; Berkow et al., 1992).

Sulfadiazine (0.056M) was evaluated by the inventors using the first described disc susceptibility procedure and was shown to enhance the relative activity of erythromycin against S. aureus 27660 by 183% (Table 8).

EXAMPLE X

Inhibitors of Polyamine Synthesis

Igarashi et. al. (1979) showed a decrease in polypeptide synthesis when an E. coli polyamine-requiring mutant was grown in the absence of polyamines. This suggested to the inventors that when inhibitors of polyamine synthesis are combined with antimicrobials, increased antimicrobial activity should be observed, due to the reduction in methylase synthesis. A number of agents capable of inhibiting polyamine synthesis are described below.

1. α-methylornithine

Mach et al. (1982) reported that polyamines are essential in prokaryotes and eukaryotes for optimal growth and development. Polyamines had previously been reported to bind in a specific way to both tRNAs and ribosomes. Mach et al. (1982) presented data to show that SAM-dependent transmethylation reactions can be regulated by alterations of polyamine concentrations in vivo. Methyltransferases from *Dictyostelium discoideum* were almost inactive without the addition of added polyamines. Additionally, for example, it was found that the growth of *D. discoideum* was arrested in four hours with 5 mM α-methylornithine.

α-methylornithine is available from Sigma Chemical Company, and is proposed for use in combination with antibiotics at doses of between about 1 and about 1000 mg/kg body weight/day, and preferably, between about 10 and about 200 mg/kg body weight/day.

2. 1,3-diaminopropan-2-ol

In the studies by Mach et al. (1982), the growth of *D. discoideum* was also arrested in four hours using 5 mM 1,3-diaminopropan-2-ol. This compound is commercially available from Fluka (Buchs, Switzerland), and is also proposed for use at doses of between about 1 and about 1000 mg/kg body weight/day, and preferably, between about 10 and about 200 mg/kg body weight/day.

3. Difluoromethylornithine and Difluoromethylarginine

Tyms et al. (1988) reviewed the use of polyamine inhibitors in antimicrobial chemotherapy. Concerning difluoromethylornithine (DFMO), an irreversible inhibitor of ornithine decarboxylase (ODC), they indicated that some bacteria may not show growth inhibition since an alternative biosynthetic pathway for putrescine exists in these organisms.

To block putrescine biosynthesis in some procaryotic cells using DMFO, inhibition of an additional pathway is necessary. This can be achieved by the prevention of arginine formation through inhibition of arginine decarboxylase activity, e.g., using difluoromethylarginine (DFMA), another catalytically activated, irreversible inhibitor.

It has been shown in clinical trials that DFMO is effective against Trypanosomiasis at different dosage levels and modes of treatment by different groups. As an example, DFMO was administered in one study at 400 mg/kg qid, for 4 to 6 weeks. In another study, DFMO was administered 20 g i.v. for 11 days, 30 g daily for 2 days and 15 g orally every day for 7 weeks. Tyms (1988) concluded that DFMO is safe and well tolerated and the side effects are reversible. Additionally, DL-α-monofluoromethyldehydroornithine methylester, a DFMO analogue, is take up more readily than DFMO ($K_i$=39 $\mu$M) and readily cleaved to the free amino acid within the cell and has a $K_i$ of 3 $\mu$M.

The present inventors therefore propose that DFMO, DFMA or a combination of DFMO and DFMA, will be effective as inhibitory agents, or as an inhibitory package, for use with an antimicrobial agent, such as an MLS antibiotic. It is proposed that DFMO or analogues alone or in combination with DFMA could be used successfully with antimicrobials to kill microorganisms at doses of about 1 to 10,000 mg/kg per day, and preferably 50 to 1000 mg/kg/day. DFMO (0.046M) was evaluated by the inventors using the first disc susceptibility procedure and shown to enhance the relative activity of erythromycin against *S. aureus* by 250% (Table 8).

4. Inhibitors of S-Adenosylmethionine Decarboxylase (SAM-DC)

The potential importance of inhibitors of the first enzyme in the synthesis of polyamines have been demonstrated by the success of DFMO, an inhibitor of ornithine decarboxylase, in the treatment of Trypanosomiasis. In order to convert putrescine into polyamines spermine and spermidine, the aminopropyl group is supplied by the catalytic activity of SAM-DC. Therefore, the action of SAM decarboxylase is essential for the synthesis of polyamines. It is therefore expected that inhibitors of SAM decarboxylase will operate in a similar fashion to ornithine decarboxylase inhibitors.

Pegg & McCann (1992) suggested that SAM-DC inhibitors may be of therapeutic value, either alone or in combination with ornithine decarboxylation inhibitors. These authors described powerful irreversible inhibitors of SAM-DC that are available, including 5'-([(Z)-4-amino-2-butenyl] methylamino)-5'-deoxyadenosine, an enzyme activated inhibitor, and 5'-deoxy-5'-[(3-hydrazinopropyl) methylamino]adenosine, which binds to the active site and forms a covalent bond with the pyruvate prosthetic group. The teachings of Pegg & McCann (1992) regarding SAM-DC inhibitors in the treatment of tumors and, particularly, in the treatment of protozoan parasites, is relevant to the choice of SAM-DC inhibitors and appropriate doses for use in the combined antimicrobial therapy of the present invention.

A number of useful inhibitors of SAM-DC have been developed based on substrate or product analogues or compounds that form a covalent bond with the pyruvate co-factor. Some of the important inhibitors are AMA (S-(5'-deoxy-5'-adenosyl)methylthioethylhydroxylamine), MHZPA (5'-deoxy-5'-[(3-hydrazinopropyl)methylamino] adenosine), MAOEA (5'-deoxy-5'-[(2-aminooxyethyl)-methylamino]adenosine, AbeAdo (5'-{[(Z)-4-amino-2-butenyl]methylamino}-5'-deoxyadenosine [MDL 73811]), AdoMac (S-(5'-deoxy-5'-adenosyl)-1-amino-4-methylthio-2-cyclopentene, MGBG (methylglyoxal bis(guanyl) hydrazone), CGP-39'937 and CGP-33'829.

Pegg & McCann (1992), reported that AbeAdo is at least 100-fold more potent than DFMO, which is now an approved drug for West African sleeping sickness. It is proposed that AbeAdo and analogues alone, or in combination with DFMA and or DFMO, could be used successfully with antibiotics to kill bacteria. The proposed dosages of AbeAdo and analogues is from about 1 to about 1,000 mg/kg per day, and preferably, from about 1 to about 200 mg/kg/day.

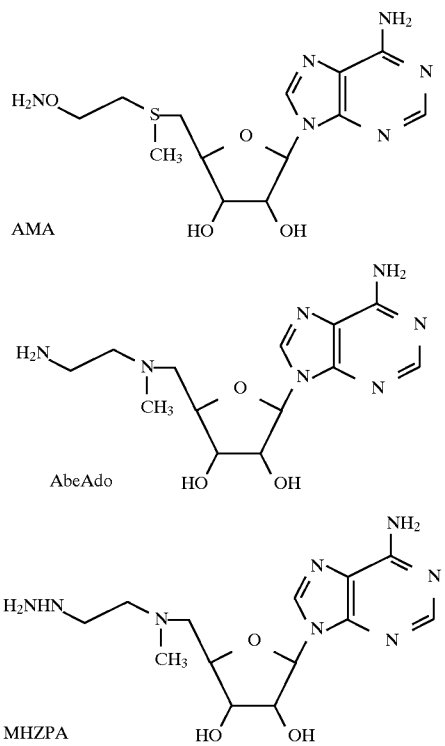

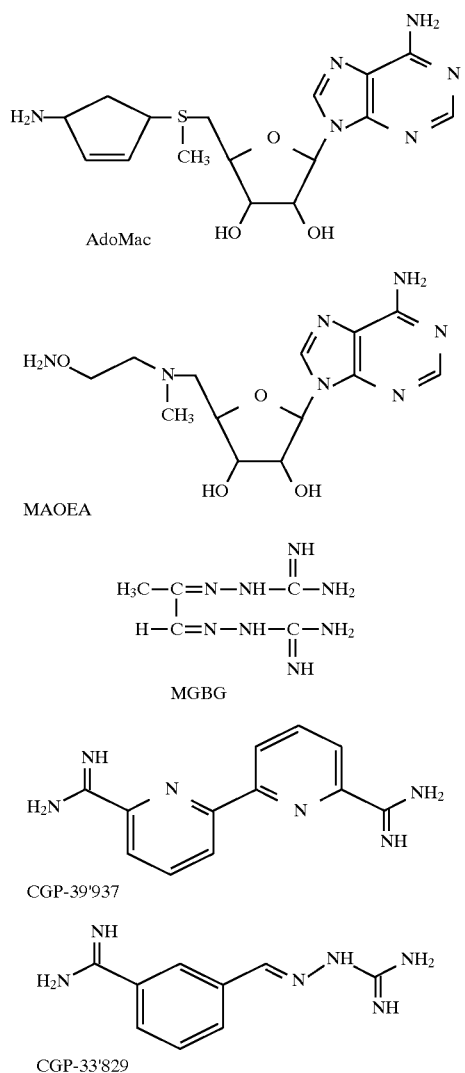

5. Inhibitors of Ornithine Decarboxylase (ODC)

McCann & Pegg (1992) reported that ornithine decarboxylase (ODC) is a suitable enzyme target for use in certain therapeutic regimens. These authors describe the therapeutic effects resulting from ODC inhibition and particularly describe the inhibitor, eflornithine. Recent in vivo therapeutic approaches to ODC inhibition are also described, as may be applied cancer treatment, cancer chemoprevention, autoimmune diseases, ischemia, hyperplasia, hearing loss, African trypanosomiasis, AIDS, and other infectious diseases/organisms. In light of the teachings of McCann & Pegg (1992), and the present disclosure, the use of ODC inhibitors can be readily adapted for combination therapy with antimicrobials in the treatment of microbial infections and diseases.

6. Inhibitors of Arginine Decarboxylase (ADC)

As stated above, Tyms et al. (1988) reported on the inhibition of polyamine synthesis by preventing arginine formation. This is achieved through the inhibition of arginine decarboxylase (ADC). DFMA is a irreversible inhibitor of ADC, which is contemplated for use in the present invention at similar doses to those quoted above for DFMO. Kallio et. al. (1981) described DL-α-(difluoromethyl) arginine as a potent and irreversible inhibitor of bacterial ADC. DL-α-(difluoromethyl)arginine (RMI 71669) will thus be effective alone and also in combination with ODC inhibitors. In the latter case, all putrescine biosynthesis may be inhibited in prokaryotic cells.

EXAMPLE XI

Inhibitors of RNA Maturation 1. 5-Azacitidine

5-Azacitidine inhibits the maturation of rRNA (Suhudolnik, 1979). The formation of 28S and 18S, but not of 38S RNA, is severely inhibited. 5-Azacitidine is commercially available from Sigma Chemical Company. The structure of 5-Azacitidine is shown below. Budavari et al. (1989) reported the oral toxicity of 5-azacitidine as 572.3 mg/kg in mice. This compound is therefore proposed for use with antibiotics at doses of between about 1 and about 300 mg/kg body weight/day, and preferably, between about 10 and about 75 mg/kg body weight/day.

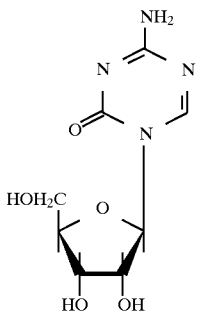

2. Cordycepin (3'-deoxyadenosine)

Cordycepin (Suhudolnik, 1979) inhibits the synthesis of mature rRNA, ribosomal precursor 45S RNA and tRNA in Hela cells; DNA and protein synthesis are not affected. Cordycepin at 200 μg/ml totally inhibits RNA synthesis and at lower concentrations, rRNA and tRNA syntheses are selectively inhibited, but protein synthesis is not effected. Cordycepin is commercially available from Sigma Chemical Company and it's structure is shown below. It is proposed for use with antibiotics at doses of between about 1 and about 250 mg/kg body weight/day, and preferably, between about 5 and about 75 mg/kg body weight/day.

3. Toyocamycin and Analogues Suhadolnik (1979) indicated that tubercidin, toyocamycin and 6-thioguanosine inhibit the formation of mature 28S and 18in Novikoff hepatoma cells. Similarly, toyocamycin was reported to inhibit the maturation of rRNA in S. cerevisiae, and is proposed for use with, e.g., MLS antibiotics, at doses of between about 0.1 and about 100 mg/kg body weight/day, and preferably, between about 0.1 and about 50 mg/kg body weight/day.

EXAMPLE XII

ANTISENSE OLIGONUCLEOTIDES

Cohen & Hogan (1994; incorporated herein by reference) describe the general approach used to develop synthetic oligonucleotides as drugs.

1. Translation Inhibition

DNA or RNA antisense oligonucleotides are also contemplated as another means of inhibiting bacterial methylation. In such methods, oligonucleotides capable of hybridizing with those portions of the mRNA sequences that are involved in binding to the ribosome or to the methylation site of the rRNA may be employed. This will block the induction of the bacterial methylase synthetase and thus reduce antibiotic resistance when used in combination with an antibiotic. Exemplary sequences are set forth below, modifications of which may be readily designed using the teaching herein and the known sequences and structural information, such as that described by Dubnau (1984; 1985) and Denoya et al. (1986).

ermC is known to specify an rRNA methyltransferase that confers resistance to erythromycin. The transferase $N^6,N^6$-dimethylates an adenine residue at position 2058 on the 23S rRNA, thereby decreasing ribosomal affinity for erythromycin. Basically the ermC mRNA exists in an inactive conformation in which the ribosome binding site for methylase synthesis, the Shine Delgarno sequence 2 (SD2), is sequestered by base pairing. Stalling of a ribosome under the influence of erythromycin binding during translation of a 19-amino acid leader peptide causes the inactive mRNA structure to open, and free the sequestered SD2 permitting initiation of methylase synthesis.

The structure of the ermC mRNA regulatory region is shown in FIG. 1 of Dubnau (1985) and FIG. 4 of Dubnau (1984). In this region, the ribosomal binding site for the putative leader peptide is defined as SD1. SD1 has the sequence AGGAGGA, which is followed six residues down by the initiation codon ATG (also referred to as AUG). The complete SD1 site, AGGAGGAAAAATATG (SEQ ID NO:1), is the primary target proposed for antisense inhibition.

The inventors have designed complementary oligonucleotide sequences against this region that will hybridize to the SD1+initiation codon region, thus preventing binding of this mRNA to the ribosome. A candidate complementary, or antisense, oligonucleotide is: TCCTCCTTTTTTATAC (SEQ ID NO:2), or UCCUCCUUUUUUAUAC (the ribooligonucleotide, SEQ ID NO:3).

In the ermC mRNA region, there is also an additional ribosomal binding site, SD2. This has a regulatory role and is usually translationally inactive due to base pairing. SD2 and the initiation codon has the sequence AGAGGGTTATAATG (SEQ ID NO:4). Since the ermC mRNA structure in the regulatory region can re-arrange into different conformations, and thus open the SD2 sequence, an oligonucleotide complementary to the SD2+initiation codon region is also proposed for use in arresting translation of the methylase enzyme. An appropriate candidate antisense deoxy oligonucleotide is: TCTCCCAACACTAC (SEQ ID NO:5).

Oligonucleotides will be designed and synthesized (Gait, 1984; Zon & Geiser, 1991). The appropriate length of the oligonucleotide to allow efficient hybridization at physiological salt concentration and temperature will be determined by computer analysis (Rychlik & Rhoads, 1989; Van Ness & Chen, 1991). These oligonucleotide will contain appropriate modifications that will allow sufficient stability in vivo and allow adequate transport into the cell. These oligonucleotide will be evaluated in vitro by their ability to prevent synthesis of the rRNA methylase. Active compound identified in vitro will then be evaluated in vivo as a "new antibiotic", as described by Lorian (1991).

2. Decoy Substrates

Oligoribonucleotides with sufficient stability are also contemplated for use as decoys to serve as substrates for the methylase enzyme. The "decoy oligos" would have tight binding properties and function to bind with, and saturate, the active-site of the methylase enzyme. Appropriate decoy sequences are those surrounding the target site of dimethylation on the 23S rRNA and the autoregulatory site on the ermC mRNA. The oligos used may have the sequences as taught below or variations thereof designed using this disclosure and the sequences and structural information described in the literature, e.g., FIG. 6 of Denoya et al. (1986; incorporated herein by reference).

Particular inhibitory structures proposed by the inventors are set forth below and are represented by SEQ ID NO:6, SEQ ID NO:7 and SEQ ID NO:8. Binding to the double stranded sequence is preferred. The sequence will depend on the organisms targeted and may contain degenerated sequences. These structures can also contain any group or modification that the enzyme will tolerate.

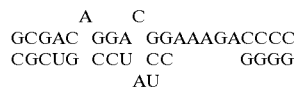

and

Additionally, the potency of the decoy oligos can be improved by designing a group into the molecule that has the ability to covalently attach to the enzyme and permanently inactivate it. Many different groups that function in this capacity are known in the art. For example, the reactive oligonucleotide derivatives used as gene-targeted biological active compounds, that are currently in use in this field, have recently been reviewed Knorre & Vlassov (1991). These authors indicated that since it appears that binding of deoxyribonucleotides to the coding region of mRNAs does not effect translation, because the translating ribosome displaces bound oligonucleotides, coupling of reactive groups that crosslink to form covalent bonds with the target will create an insurmountable block for the ribosome. Examples of modifications coupled to oligonucleotides that crosslink to target are 2-chlorethylamino-, EDTA Fe- and o-phenanthroline Cu-groups. Additionally groups that increase binding to nucleic acid targets could also be used, such as phenazinium-conjugated oligonucleotides.

3. Specific Bacterial Targets

It will be understood that, generally, the sequence of methylase mRNAs and rRNAs from different bacteria will not be identical. The sequence variations will need to be considered when designing oligonucleotides for use in connection with specific bacteria. Sequences are readily available from data bases, such as GenBank.

4. Modifications

Depending on the Tm' of the oligonucleotide:mRNA hybrid, the length of the oligonucleotide will be optimized for maximum activity.

In addition to any of the common bases, the oligonucleotides may also contain other naturally occurring or modified bases. For example, both deoxyribonucleotides and ribonucleotides may contain backbone modifications, including methylphosphonates, phosphorothioates, phosphorodithioates and PNAs (protein nucleic acids; sugar modifications, including 2'-alkyl groups; base modifications, including inosine, alphanucleoside, and 3' and 5' blocking groups, including cholesterol, 3' and 5' alkylhydroxyl groups, and interchelators.

Such modifications, individually or in combination, are proposed for use in designing an oligonucleotide that hybridizes specifically to the initiation target and additionally contains sufficient stability against nuclease degradation. Certain preferred oligonucleotides include 3'- and/or 5'-blocked oligodeoxynucleic acids. The advantage of such oligodeoxynucleotides is that the endogenous RNase H, would degrade the complementary mRNA when the oligodeoxynucleotide/mRNA hybrid. This is contemplated to allow permanent inhibition of the translation of this particular methylase mRNA.

5. Oligonucleotide Delivery

A technology that allows the transport of oligonucleotides into bacteria has recently been developed (Couvreur et al., 1991; incorporated herein by reference) and is commercially available from Genta Corporation, San Diego, Calif.

EXAMPLE XIII

PHARMACEUTICAL COMPOSITIONS

Compositions of the present invention may comprise a combined effective amount of an antimicrobial agent or antibiotic and an agent that inhibits rRNA methylation or maturation, or such agents may be provided as distinct compositions, intended for use in combination. The antibiotics, second agent inhibitors or combinations thereof, may be dissolved or dispersed in a pharmaceutically acceptable carrier or aqueous medium, or may be provided in solid form.

The phrases "pharmaceutically or pharmacologically acceptable" refer to molecular entities and compositions that do not produce adverse, allergic or other untoward reactions when administered to an animal, or a human, as appropriate. As used herein, "pharmaceutically acceptable carrier" includes any and all solvents, dispersion media, coatings, additional antibacterial and antifungal agents, isotonic and absorption delaying agents, and the like (USP XXII, The United States Pharmacopeia, 1990; incorporated herein by reference).

The use of such media and agents for pharmaceutical active substances is well known in the art. Except insofar as any conventional media or agent is incompatible with the active ingredient, its use in the therapeutic compositions is contemplated. Supplementary active ingredients, particularly other non-MLS antibiotics, can also be incorporated into the compositions.

In addition to the detailed information provided herein, the teachings of Eliopoulos & Moellering (1991) and Shungu (1991) are incorporated by reference for the purposes of further describing appropriate antimicrobial combinations and the use of antibiotics in medicine.

Kits for use in the present invention are contemplated to include various combinations of solutions, tablets, ointments and other formulations, and also to encompass two component systems. One component will be at least one inhibitor that will be administered, generally at a predetermined time before the MLS antibiotic (the second component). Additional components may be used in the context of the therapeutic methods provided by this invention, although they may not be included in a kit per se. For example, $N_2O$, used extensively in dentistry, may be employed in essentially in the same way, and given simultaneously and/or as a pretreatment to antibiotic therapy.

1. Parenteral Formulations

The active compounds, whether antibiotics, second agent inhibitors, or combinations thereof, may be formulated for parenteral administration, e.g., formulated for injection via the intravenous, intramuscular, sub-cutaneous, or even intraperitoneal routes (USP XXII, The United States Pharmacopeia, 1990). The preparation of an aqueous composition that contains such active ingredients, or combinations thereof, will be known to those of skill in the art in light of the present disclosure. Typically, such compositions can be prepared as injectables, either as liquid solutions or suspensions. Solid forms suitable for using to prepare solutions or suspensions upon the addition of a liquid prior to injection can also be prepared, and the preparations can also be emulsified.

Solutions of each or both of the active compounds as free base or pharmacologically acceptable salts can be prepared in water suitably mixed with a surfactant (USP XXII, The United States Pharmacopeia, 1990) such as hydroxypropylcellulose. Dispersions can also be prepared in glycerol, liquid polyethylene glycols, in mixtures thereof and in oils. Under ordinary conditions of storage and use, these preparations will contain a preservative to prevent the growth of microorganisms.

The pharmaceutical forms suitable for injectable use include: aqueous solutions or dispersions, formulations including sesame oil, peanut oil or aqueous propylene glycol and powders for the extemporaneous preparation of injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The antibiotics and second inhibitory agents can be formulated into one or more compositions in a neutral or salt form. Pharmaceutically acceptable salts, include the acid addition salts (formed with the free amino groups of the protein) which are formed with inorganic acids such as, for example, hydrochloric or phosphoric acids, or such organic acids as acetic, oxalic, tartaric, mandelic, lactic and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filter sterilization. Generally, dispersions are prepared by incorporating the various sterilized active ingredients into a sterile vehicle which contains the basic dispersion medium and the required other ingredients from those enumerated above. In the case of sterile powders for the preparation of injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for intramuscular injection is also contemplated. This is envisioned to have particular utility in cases where either the antibiotic or the inhibitor is sensitive to digestive conditions. In this regard, the use of DMSO as solvent is preferred as this will result in extremely rapid penetration, delivering high concentrations of the active agents to a small area.

Upon formulation, solutions will be administered in a manner compatible with the dosage formulation and in such amount as are therapeutically effective, as outlined in the foregoing examples. The formulations are easily administered in a variety of dosage forms. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1033 and 1570–1580). Some variation in dosage will necessarily occur depending on the condition of the subject being treated. The person responsible for administration will, in any event, determine the appropriate dose for the individual subject.

In addition to the compounds formulated for parenteral administration, other pharmaceutically acceptable forms are also contemplated for use, including, e.g., tablets or other solids for oral administration; time release capsules; forms for topical administration, including creams and lotions; mouthwashes; aerosols, inhalents and the like.

The components for use with the invention may be prepared in the form a treatment kit wherein the antibiotic and inhibitory agent are located within a suitable container, such as at least one vial, test tube, flask, bottle, syringe or other container, into which the active components are placed, and preferably, suitably allocated. Where desired, the antibiotic and inhibitor may be provided in distinct containers, such that the kit will contain two vials, or other containers, each of which contains only one of the active agents. These "therapeutic kits" will also typically include a means for containing the vials or the containers in close confinement for commercial sale, such as, e.g., injection or blow-molded plastic containers into which the desired vials are retained.

2. Oral Formulations

In certain embodiments, active compounds may be administered orally. This is contemplated for agents that are generally resistant, or have been rendered generally resistant, to proteolysis by digestive enzymes. Such compounds are comtemplated to include the antibiotics and most of the inhibitory second agents disclosed herein. Naturally, the preferred inhibitors will be the more active compounds and those already cleared by the FDA for other uses, as will be known to those of skill in the art in light of the present disclosure.

For oral administration, the active compounds and/or combinations thereof may be administered, for example, with an inert diluent or with an assimilable edible carrier, or they may be enclosed in hard or soft shell gelatin capsule, or compressed into tablets, or incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compounds or combinations thereof. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings to modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

3. Topical Formulations

The formulation of antimicrobial agents, such as antibiotics, and second, inhibitory agents for topical use, such as in creams, ointments and gels is also contemplated. The preparation of oleaginous or water-soluble ointment bases is also well known to those in the art. For example, these compositions may include vegetable oils, animal fats, and more preferably, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates. Even delivery through the skin may be employed if desired, e.g., by using transdermal patches, ionophoresis or electrotransport. Examples of hydrophilic and hydrophobic ointments are known in the art, (e.g., USP XXII, The United States Pharmacopeia, 1990).

4. Nasal Solutions and Inhalants

One may also use nasal solutions or sprays, aerosols or inhalants with the antimicrobials and second agents described herein. Nasal solutions are usually aqueous solutions designed to be administered to the nasal passages in drops or sprays. Nasal solutions are prepared so that they are similar in many respects to nasal secretions, so that normal ciliary action is maintained. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known and include, for example, those for use with various antibiotics and antihistamines.

Inhalations and inhalants are pharmaceutical preparations designed for delivering a drug or compound into the respiratory tree of a patient. A vapor or mist is administered and reaches the affected area to give relief from symptoms of bronchial and nasal congestion. Inhalations may be administered by the nasal or oral respiratory routes. The administration of inhalation solutions is only effective if the droplets are sufficiently fine and uniform in size so that the mist reaches the bronchioles.

Another group of products, also known as inhalations, and sometimes called insufflations, consists of finely powdered or liquid drugs that are carried into the respiratory passages by the use of special delivery systems, such as pharmaceutical aerosols, that hold a solution or suspension of the drug in a liquefied gas propellant. When released through a suitable valve and oral adapter, a metered does of the inhalation is propelled into the respiratory tract of the patient.

Particle size is of major importance in the administration of this type of preparation. It has been reported that the optimum particle size for penetration into the pulmonary cavity is of the order of 0.5 to 7 $\mu$m. Fine mists are produced by pressurized aerosols and hence their use in considered advantageous. The active compounds described above, whether antibiotics, second agent inhibitors, or combinations thereof, may be formulated for nasal administration in any of these methods.

5. Ophthalmic Solutions

The antimicrobials and agents that inhibit rRNA methylation or maturation may also be used in preparations of pharmaceutical compositions suitable for use as ophthalmic solutions. The preparation of ophthalmic formulations in accordance with conventional pharmaceutical practice is well known, see for example "Remington's Pharmaceutical Sciences" 15th Edition, pages 1488 to 1501 (Mack Publishing Co., Easton, Pa.).

The ophthalmic preparations may contain antibiotics and/ or second agents, or pharmaceutically acceptable salts thereof, in a concentration from about 0.01 to about 1% by weight, preferably from about 0.05 to about 0.5% in a pharmaceutically acceptable solution, suspension or ointment. Some variation in concentration will necessarily occur, depending on the particular compound employed, the condition of the subject to be treated and the like, and the person responsible for treatment will determine the most suitable concentration for the individual subject. The ophthalmic preparation will preferably be in the form of a sterile aqueous solution containing, if desired, additional ingredients, for example preservatives, buffers, tonicity agents, antioxidants and stabilizers, nonionic wetting or clarifying agents, viscosity-increasing agents and the like.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH between about 6 and 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfate, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, carboxymethylcellulose and the like. The ophthalmic preparation will be administered topically to the eye of the subject in need of treatment by conventional methods, for example in the form of drops or by bathing the eye in the ophthalmic solution.

6. Liposomes and Nanoparticles

Couvreur et al. (1991) review the potential of liposomes and nanoparticles in the targeted antibiotic therapy of intracellular bacterial infections and diseases. Nanoparticles can generally entrap antibiotics in a stable and reproducible way (Henry-Michelland et al., 1987). To avoid side effects due to intracellular polymeric overloading, such ultrafine particles (sized around 0.1 $\mu$m) should be designed using polymers able to be degraded in vivo. Biodegradable polyalkylcyanoacrylate nanoparticles that meet these requirements are proposed for use in the present invention. They are easily made, as described by Couvreur et al. (1984; 1988). In serum, the liberation of ampicillin from nanoparticles was found to follow zero-order kinetics (Fattal et al., 1991a, 1991b).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 $\mu$m. Sonication of MLVs results in the formation of small unilamellar vesicles (SUVs) with diameters in the range of 200 to 500 Å, containing an aqueous solution in the core.

Liposomes bear many resemblances to cellular membranes and are contemplated for use in connection with the present invention as carriers for the antibiotics and/or second agents. They are widely suitable as both water- and lipid-soluble substances can be entrapped, i.e., in the aqueous spaces and within the bilayer itself, respectively. It is possible that drug-bearing liposomes may even be employed for site-specific delivery of active agents by selectively modifying the liposomal formulation.

The formation and use of liposomes is generally known to those of skill in the art. For example, Couvreur et al. (1991; incorporated herein by reference) describe the use of liposomes and nanoparticles in the targeted antibiotic therapy of intracellular bacterial infections and diseases. Recently, liposomes were developed with improved serum stability and circulation half-times (Gabizon & Papahadjopoulos, 1988; Allen & Choun, 1987).

In addition to the teachings of Couvreur et al. (1991), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins such as cytochrome c bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity and surface charge. They may persist in tissues for hours or days, depending on their composition, and half lives in the blood range from minutes to several hours. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Using the combined antimicrobial formulations described herein in liposomal formulations will lead to further particular advantages that relate to targeting. The properties of liposomes and nanoparticles will likely improve therapy in a number of bacterial infections that are presently difficult to cure. As set forth by Couvreur et al. (1991), liposomes and nanoparticles themselves cannot escape from the circulation because of the endothelial barrier, with exception to tissues with discontinuous endothelia lining their capillaries (i.e., liver, spleen, and bone marrow). This leads to the rapid clearance of these ultrafine particulate carriers from the blood and to their capture by the cells of the reticuloendothelial system (Poste, 1933; Grislain et al., 1983). This corresponds exactly to the sane tissue distribution pattern as that of the majority of the bacteria responsible for intracellular infection. In addition, it has been shown that liposomes are taken up by circulating blood monocytes, which are known to infiltrate some infectious lesions (Tulkens, 1985). Also, as with bacteria, both liposomes and nanoparticles will likely penetrate cells by endocytosis, first forming phagosomes, which in turn fuse with lysosomes to form phagolysosomes or secondary lysosomes (Couvreur et al., 1977).

The advantages of liposomes and nanoparticles has been described for various cases. Liposome-associated cephalothin has been shown to be more effective than free drug in the treatment of experimental murine salmonellosis (Desiderio and Campbell, 1933). The therapeutic index of ampicillin, calculated on the basis of mouse mortality, has been reported to be increased by 120-fold upon binding to nanoparticles (Fattal et al., 1989). Guinea pigs infected by *Brucella canis* and treated with liposome-entrapped streptomycin were found to be free of bacteria (2×10 mg/kg), whereas animals treated with the free drug, for the same schedule of administration, showed only a minor reduction in the number of surviving bacteria (Fountain et al., 1985). The delivery of antibacterial drugs to phagocytic cells has also been demonstrated to be feasible with amikacin (Düzgünes et al., 1988), kanamycin and tobramycin (Fountain et al., 1985).

7. Therapeutic Kits

Therapeutic kits comprising antimicrobial agents and methylation inhibitors are contemplated and will generally contain, in suitable container means, any of the previously described or other suitable pharmaceutically acceptable formulations of one or more antibiotics and inhibitors. The kit may have a single container means for both (or all) components or it may have more than one distinct container means.

When the components of the kit are provided in one or more liquid solutions, the liquid solution will generally be an aqueous solution, with a sterile aqueous solution being particularly preferred. However, the components may also be formulated into a syringable composition. In which case, the container means may itself be a syringe, pipette, eye dropper, or other such like apparatus, from which the formulation may be applied to an infected area of the body, injected into an animal, or even applied to and mixed with the other components of the kit.

The components of the kit may also be provided as dried powder(s). When reagents or components are provided as a dry powder, the powder can be reconstituted by the addition of a suitable solvent. It is envisioned that the solvent may also be provided in another container means. The container means will generally include at least one vial, test tube, flask, bottle, syringe or other container means, into which the antibiotics and methylation inhibitors may be placed, preferably, suitably allocated. The kits may also comprise the second/third container means mentioned above for containing a sterile, pharmaceutically acceptable buffer or other diluent.

The kits of the present invention will also typically include a means for containing the vials in close confinement for commercial sale, such as, e.g., injection or blow-molded plastic containers into which the desired vials are retained. Irrespective of the number or type of containers, the kits of the invention may also comprise, or be packaged with, an instrument for assisting with the administration, placement or injection of the components or combined composition within the body of an animal. Such an instrument may be a syringe, pipette, forceps, measured spoon, eye dropper or any such medically approved delivery vehicle or device.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Acar & Goldstein, Disk Susceptibility Test, In: *Antibiotics in Laboratory Medicine*, Lorian, V. Ed., Williams & Wilkins, Philadelphia, 17–52, 1991.

Allen and Choun, FEBS Lett., 223:42–46, 1987.

Ansfield et. al., *Infec. Immum.*, 17:195–204, 1977.

Arka & Balows, In: *Experimental Models in Antimicrobial Chemotherapy*, Zak & Sande Eds., Academic Press, London, Vol. 1, pp. 355–369, 1986.

Aswad et al., *J. Bacteriol.*, 118:640–645, 1974

Avila et al., *Am. J. Trop, Med. Hyg.*, 43:139–145, 1990.

Backlund et al., *Eur. J. Biochem.*, 160:243–251, 1986.

Baden & Monk, *Toxicol. Let.*, 7:259–262, 1981.

Baker & Vermeulen, *J. Med. Chem.*, 12:680–684, 1969.

Baker & Vermeulen, *J. Med. Chem.*, 13:1154–1160, 1970a.

Baker & Vermeulen, *J. Med. Chem.*, 13:82–86, 1970b.

Barbes et al., *FEMS Microbiol. Letters*, 69:239–244, 1990.

Barton et al., *J. Chem. Soc.*, Perkin Trans., 1:981–985, 1991.

Barton et al., *J. Med. Chem.*, 35:63–67, 1992.

Bauer et al., *Am. J. Clin. Pathol.*, 45:493–496, 1966.

Berkelman et al., *Science*, 264:368–370, 1994.

Berkow et al. Ed., *The Merck Manual of Diagnosis and Therapy*, Sixteenth Edition, Merck Research Laboratories, Merck & Co, Rahway, N.J., pp 48; 52–53; 1278–1279; 1718; 1992.

Beskid et. al., *Antimicrob. Agents Chemother.*, 20:159–167, 1981.

Blaney et al., *Chem. Rev.*, 84:333–407, 1984.

Bona et al., *Biochem. Biophys. Res. Comm.*, 70:622–628, 1976.

Borchardt et al., *J. Biol. Chem.*, 259:4353–4358, 1984.

Bowden et al., *J. Chemother.*, 5:377–388, 1993

Brogden et al., *Drugs*, 46:652–677, 1993

Budavari et al., Eds, In: *The Merck Index,* 11th Ed., Merck & Co., Inc., Rahway, N.J., 1989.

Buckle et al., *Naunyn-Schmiedebergs Arch. Pharmacol.,* 316:64–68, 1981.
Butler & Gotschlich, *J. Bacteriol.,* 173:5793–5799, 1991.
Caboche & Bachellerie, *Eur. J. Biochem.,* 74:19–29, 1977.
Campbell et al., *Anal. Biochem.,* 194:268–277, 1991.
Chang & Coward, *J. Med. Chem.,* 19:684–691, 1976.
Cleeland & Squires, In: Lorian, *Antibiotics in Laboratory Medicine*, Satterfield (Ed), Williams & Wilkins, Philadelphia, 1991
Cohen & Saint-Girons, In *Escherichia coli and Salmonella typhimurium*, Neidhardt (Editor), ASM, Washington D.C., vol. 1, pp. 429–444, 1987.
Cohen & Hogan, *Scientific American,* 271:76–82, 1994.
Corbeil et. al., *Infect. Immun.,* 26:984–990, 1979.
Corbett et al., *Canc. Res.,* 42:1707–1715, 1982.
Corrales et al., *Hepatology,* 14:528–533, 1991.
Couvreur et al., *FEBS Lett.,* 84:323–326, 1977.
Couvreur et al., U.S. Pat. No 4:489,555, 1984.
Couvreur, *Crit. Rev. Ther. Drug Carrier Syst.,* 5:1–20, 1988.
Couvreur et al., *Pharm. Res.,* 8:1079–1086, 1991.
Coward et al., *J. Med. Chem.,* 17:1286–1289, 1994.
Cunliffe, In: *The Ribosome: Structure, Function and Evolution*, Hill et al., Eds., 479–490, 1990.
Dacey & Sande, *Antimicrob. Agents Chemother.,* 6:437–441, 1974.
Davies, *FEMS Microbiology Reviews,* 39:363–371, 1986.
Davis et. al., *Arch. Ophthalmol.,* 95:1638–1643, 1977.
De Clercq, *Biochemical Pharmacology,* 36:2567–2575, 1987.
De Clercq & Cools, *Biochem. Biophys. Res. Comm.,* 129:306–311, 1985.
De Clercq & Cools, *Biochem. Pharmacol.,* 38:1061, 1989.
Denoya et al., *J. Bacter.,* 168:1133–1141, 1986.
Desiderio and Campbell, *J. Reticuloendothel. Soc.,* 34:279–287, 1983.
Devlin, In: *Textbook of Biochemistry with Clinical Correlations*, Wiley Medical Publications, NY., pp 745, 1986.
Diliberto et al., *Proc. Nat. Acad. Sci.,* 73:4050–4054, 1976.
Drew et al., *Biochem. Pharmacol.,* 33:2989–2994, 1984.
Dubnau, *CRC Critical Reviews in Biochemistry,* 16:103–132, 1984.
Dubnau, *EMBO J.,* 4:533–547, 1985.
Düzgünes et al., *Antimicrob. Agents Chemother.,* 32:1404–1411, 1988.
Eliopoulos & Moellering, In: *Antibiotics in Laboratory Medicine*, Satterfield (Ed), Williams & Wilkins, Philadelphia, pp. 432–492, 1991.
Ernst & Sande, In: *Action of Antibiotics in Patients*, Sabath, Ed., Hans Huber Publishers, Bern, Switzerland, pp. 68–73, 1981.
Fattal et al., *Antimicrob. Agents Chemother.,* 33:1540–1543, 1989.
Fattal et. al., *J Microencapsul,* 8(1):29–36, 1991a.
Fattal et. al., *Antimicrob Agents Chemother,* 35(4):770–772, 1991b.
Finkel & Groner, *Virol.,* 131:409–425, 1983.
Fischer et al., *J. Antibiot.,* 15:873–881, 1987.
Fleming & Schilsky, *Semin. Oncol.,* 19:707–719, 1992.
Fountain et al., *J. Infect Dis.,* 152–529–535, 1985.
Gabizon and Papahadjopoulos, *Proc. Natl. Acad. Sci. USA,* 85:6949–6953, 1988.
Gait, Oligonucleotide synthesis. A practical approach. IRL Press, Washington D.C., 1984.
Garrett & Kredich, *J. Biol. Chem.,* 256:12705–12709, 1981.
Garrison & Freedman, *Yale J. Biol. Med.,* 42:394–410, 1970.
Gillet et al., *Experientia,* 35:1007–1009, 1979.
Glazer & Knode, *J. Biol. Chem.,* 259:12964–12969, 1984.
Glazer et al., *Biochem. Pharmacol.,* 35:4523–4527, 1986.
Grislain et al., *Int. J. Pharm.,* 15:335–345, 1983.
Grunberg et al., *Chemotherapia,* 12:272–281, 1967.
Grunberg & Cleeland, *J. Antimicrob. Chemother.,* 3(Suppl. B):59–68, 1977.
Helland & Ueland, *Canc. Res.,* 42:1130–1136, 1982.
Henry-Michelland et al., *Int. J. Pharm.,* 35:121–127, 1987.
Hershfield, *J. Biol. Chem.,* 254:22–25, 1979.
Hoffman, *J. Biol. Chem.,* 253:2905–2907, 1978.
Houston et al., *J. Med. Chem.,* 28:478–482, 1985a.
Houston et al., *J. Med. Chem.,* 28:471–477, 1985b.
Igarashi et al., *Eur. J. Biochem.,* 93:345–353, 1979.
Jacquemont & Huppert, *J. Virol.,* 22:160–167, 1977.
Johnson et. al., *Antimicrob. Agents Chemother.,* 21:984–989, 1982.
Kaehaler et al., *Biochem.,* 16:5770–5775, 1977.
Kallio et. al., *Biochemistry,* 20:3163–3166, 1981.
Kane et al., *Ann. Pharmacotherap.,* 26:939–947, 1992.
Kappler et al., *J. Med. Chem.,* 29:318–322, 1986a.
Kappler et al., *J. Med. Chem.,* 29:1030–1038, 1986b.
Kappler et al., *J. Med. Chem.,* 30:1599–1603, 1987.
Kappler et al., *J. Med. Chem.,* 31:384–389, 1988.
Kato et al., *J. Biochem. Tokyo,* 101:207–215, 1987.
Keller & Borchardt, *Amer. Soc. Pharm. & Exp. Therpeut.,* 31:485–492, 1987.
Kim et al., *Biochem. Biophys. Acta,* 82:150–155, 1985.
Kitaoka et al., *Antiviral Research,* 6:57–65, 1986.
Klaassen, In: *The Pharmacological Basis of Therapeutics*, Goodman & Gilman, Eds., Pergamon Press, 8th Ed., pp. 49–61, 1990.
Knorre & Vlassov, *Gentica,* 85:53–63, 1991.
Kramer et al., *Biochem. J.,* 247:259–265, 1987.
Kramer et al., *Biochem. J.,* 249:581–586, 1988.
Kroes et al., *Br. J. Cancer,* 50(6):793–800, 1984.
Lasierra et al., *Trombosis Research,* 53:347–355, 1989.
Law et al., *Mol. Cell Biol.,* 12:103–111, 1992.
Lawrence & Robert-Gero, *J. Euk. Microbiol.,* 40:581–589, 1993.
LeClercq & Courvalin, *Antimicrobial Agents and Chemotherapy,* 35:1267–1272, 1991.
Lemeteil et al., *J.Infect. Dis.,* 167:766–768, 1993.
Levy & Merrigan, *Antimicrobial Agents and Chemotherap.,* 11:122–125, 1977.
Lhoest & Colson, In: *Protein Methylation*, Ch. 9, pp. 155–178, 1990
Li et al., *Archives Biochem. Biophys.,* 240:613–620, 1985.
Liau et al., *Canc. Res.,* 33:323–331, 1973.
Lim et al., *J. Med. Chem.,* 29:1743–1748, 1986.
Lim & Marquez, *Tetrahedron Lett.,* 24:5559–5562, 1983.
Lindley & Pisoni, *Biochem. J.,* 29:457–462, 1993.
Lombardini & Sufrin, *Biochem. Pharmacol.,* 32:489–495, 1983.
Lorian, In: *Antibiotics in Laboratory Medicine*, Satterfield (Ed), Williams & Wilkins, Philadelphia, pp. 558–559; 718, 1991.
Lyon et al., *Molecular and Cellular Biology,* 7:1759–1763, 1987.
McCann & Pegg, *Pharmacol Ther,* 54(2):195–215, 1992.
Ma et al., *Biochemistry,* 29:1412–1416, 1990.
Mach et al., *Biochem. J.,* 202:153–162, 1982.
Madell & Sande, Antimicrobial Agents In *Gilman, Rall, Nies, Taylor; Goodman and Gilman's, The Pharmacological Basis of Therapeutics*. Pergamon Press, 1047–1057, 1990.
Maylath and Leopold, *Am. J. Ophthalmol.,* 40:86–101, 1955.

Med. Let., "The choice of antibacterial drugs," *Med. Lett. Drugs Ther.* 34:49, 1992.
Minnick & Kenyon, *J. Org. Chem.,* 53:4952–4961, 1988.
Moore, *Can. J. Biochem.,* 48:702–705, 1970.
Muzutani et al., *Cancer,* 73:730–737 (1994
NCCLS Document M2-A5, Volume 13 (No. 24):11–32, 1993.
Nesher et al., *Ann. Rheum. Dis.,* 50:637–641, 1991.
Norden, *J. Infect. Dis.,* 122:410–418, 1970.
O'Dwyer et al., *Ann. Intern. Med.,* 108:733–743, 1988.
Onderdonk et al., *Infect. Immun.,* 10:1256–1259, 1974.
Ostreicher, NY State *Dent. J.,* 60(3):47–49, 1994.
Pandit et al., *Mol. Gen. Genet.,* 234:412–422, 1992.
Park et al., *J. Biol. Chem.,* 262:14702–14708, 1987.
Patil & Schneller, *J. Med. Chem.,* 35:3372–3377, 1992.
Pegg & McCann, *Pharmac. Ther.,* 56(3):359–357, 1992.
Porter et al., *Biochem. Biophys. Res. Commun.,* 122:350–357, 1984.
Poste, *Biol. Cell.,* 47:19–39, 1983.
Pugh et al., *J. Biol. Chem.,* 253:4075–4077, 1978.
Pugh & Bochardt, *Biochemistry,* 21:1535–1541, 1982.
Rapley and Walker Editors, in *Molecular Diagnostics,* Blackwell Scientific Publications, Boston, 1993. pp 371–381.
Razin et al., *Nucl. Acid Res.,* 2:1967–1974, 1975.
Reese & Betts, In: *A Practical Approach to Infectious Diseases,* (3rd ed.), Boston, Little Brown, 1991.
Reese & Betts, In: *Handbook of Antibiotics,* 2nd Ed., Little, Brown and Company, Boston, 1993.
Robert-Gero, *Biochem. Biophys. Res. Comm.,* 65:1242–1249, 1975.
Roth, Federation Proceedings, 45:2765–2772, 1986.
Ryan, In: *Chemotherapy,* Vol. 2, Williams & Gedes, Eds., Plenum, New York, pp. 205–215, 1976.
Rychlik & Rhoads, *Nucl. Acid Res.,* 17:8543–9551, 1989.
Sacks et al., *J. Clin. Invest.,* 69:226–230, 1982.
Salim & Madden, *Nature,* 244:334–366, 1973.
Schanche et al., *Mol. Pharmacol.,* 26:553–558, 1984.
Scheld et al., *Antimicrob. Agents Chemother.,* 13:899–904, 1978.
Schmidt et al., *J. Bacteriol.,* 129:15–21, 1977.
Schor et al., *J. Pharm. Sci.,* 80:311–312, 1991.
Sekura et al., *J. Biol. Chem.* 251:2263–70, 1976.
Shimizu et al., *Eur. J. Biochem.,* 141:385–392, 1984.
Shungu, In: *Antibiotics in Laboratory Medicine,* Satterfield (Ed), Williams & Wilkins, Philadelphia, Ch. 22, pp 787–828; 1991.
Shuto et al., *J. Med. Chem.,* 35:324–331, 1992.
Skinner et al., *The Journal of Biological Chemistry,* 258:12702–12706, 1983.
Spratt, *Science,* 264:388–393, 1994.
Stein et al., *Infect. Immun.,* 56:112–116, 1988.
Sufrin et al., *Mol. Pharmacol.,* 15:661–677, 1979.
Sufrin et al., *Biochim. Biophys. Acta,* 1202:87–91, 1993.
Suhadolnik, Progress in *Nucleic Acid Res.,* 22:193–291, 1979.
Svardal et al., *Canc. Chemother. Pharmacol.,* 21:313–318, 1988.
Swiatek et al., *Biochem.,* 12:4670–4674, 1973.
Thakker-Varia et al., *Plasmid,* 14:152–161, 1985.
Thong et al., *Molecular and Biochem. Parasit.,* 17:35–44, 1985.
Travis, *Science,* 264:360–362, 1994.
Tsai et al., *Chemotherapy,* 21:342–357, 1975.
Tseng et al., *J. Med. Chem.,* 32:1442–1446, 1989.
Tsujino et al. Proceedings of the 11th International Congress on Chemotherapy, 2:1559–1561, 1979.
Tulkens, In P. Buri and R. Gumma (eds.), aims, Potentialities and Problems in Drug Targeting, Elsevier, Amsterdam, 1985, pp. 179–194
Tyms et al., *J. Antimicrobial Chemotherapy,* 22:403–427, 1988.
USP XXII, The United States Pharmacopeia, The National Formulary, USP Convention, Inc. Rockville, Md., 1990 pp 975; 1688–1696; 1857–1859.
Van Ness & Chen, *Nucl. Acid. Res.,* 19:5143–5151, 1991.
Vedel & Robert-Gero, *FEBS Letters,* 128:87–89, 1981.
Vogelman et al., *J. Infect. Dis.,* 157:287–298, 1988.
Vrudhula et al., *J. Med. Chem.,* 30:888–894, 1987.
Vrudhula et al., *J. Med. Chem.,* 32:885–890, 1989.
Wainfan & Borek, *Mol. Pharmacol.,* 3:595–598, 1967.
Waksman et al., *Proc. Natl. Acad. Sci. USA,* 31:157, 1945.
Walker & Duerre, *Can. J. Biochem.,* 53:312–319, 1975.
Weideman & Atkinson, Susceptibility to Antibiotics: Species Incidence and Trends Test, in *Antibiotics in Laboratory Medicine,* Lorian, V. (Editor), Williams & Wilkins, Philadelphia, 17–52; 76–77, 1991.).
Weisblum, *British Medical Bulletin,* 40:47–53, 1984.
Whaun et. al., *Jrn. of Pharm. and Exp. Ther.,* 236:277–283, 1986.
Windholz et al, Editors, in *The Merck Index, Tenth Edition,* Merck & Co, Rahway, N.J., 1983, pp 1025–1026; 1400; 1427; 2723.
Wolfe & Borchardt, *J. Med. Chem.,* 34:1521–1530, 1991.
Wolford et al., *Exp. Hematol.,* 12:867–871, 1984.
Yagiela, *Anest. Prog.,* 38:1–11, 1991.
Yaginuma et al., *Proceedings of the* 11th International Congress on Chemotherapy, 2:1555–1559, 1979.
Yaginuma et al., *J. Antibiot.,* (Tokyo) 34:359–366, 1981.
Yamaki et al., *Nucleic Acids Res.,* 6:5067–5073, 1988.
Yamanaka et al., *Cancer Res.,* 47:1771–1774, 1987.
Yebra et al., *J. Antibiot.,* 44:1141–1147, 1991.
Zalacain & Cundliffe, Europ. *J. Biochem.,* 189:67–72, 1990.
Zak & Sande, In: *Action of Antibiotics in Patients,* Sabath, Ed., Hans Huber Publications, Bern, Switzerland, pp. 555–67, 1981.
Zappia et al., *J. Biol. Chem.,* 244:4499–4509, 1969.
Zon & Geiser, *Anti-Cancer Drug Design,* 6:539–568, 1991.
Zyskind et al., *Cell,* 69:5–8, 1992.

What is claimed is:

1. A method for reducing the resistance of an MLS-susceptible bacterium to an MLS antibiotic selected from the group consisting of a macrolide, lincosamide and streptogramin B antibiotic, the method comprising contacting said MLS-susceptible bacterium with an effective amount of said MLS antibiotic and an amount of a methylation inhibitor effective to inhibit RNA methylation or maturation in said MLS-susceptible bacterium.

2. A method for reducing the resistance of a non-viral microorganism to an antimicrobial agent, comprising contacting said non-viral microorganism with an effective amount of said antimicrobial agent in combination with an amount of a methylation inhibitor effective to inhibit methylation in said non-viral microorganism; said methylation inhibitor being selected from the group consisting of S-adenosylhomocysteine (SAH), an SAH analogue, homocysteine, an adenine derivative, a SAM analogue, a sulphonium SAM derivative, sinefungin, a sinefungin analogue, nicotinamide, a nicotinamide analogue, polyinosinate, S-N$^6$-methyladenosylhomocysteine, S-aristeromycinyl-L-homocysteine, an S-aristeromycinyl-L-homocysteine analogue, SIBA, S-Tubercidinylhomocysteine (STH), an STH analogue, A9145c, methylnicotinamide, MTA, xylosyladenine, (S)-DPHA, (D)-eritadenine, (RS)-AHPA, adenosine dialdehyde, C$^3$Ado, aristeromycin (Ari), an aristeromycin analogue, DHCeA, c$^3$-DHCeA, DHCaA, 3-deazaneplanocin A (c$^3$-NpcA), c$^3$-Ari, 6'C-methylneplanocin A, 2'deoxyadenosine, Ara-A and tubercidin.

3. A method for reducing the resistance of a non-viral microorganism to an antimicrobial agent, comprising contacting said non-viral microorganism with an effective amount of said antimicrobial agent in combination with an amount of a methylation inhibitor effective to inhibit methylation in said non-viral microorganism; wherein said methylation inhibitor inhibits S-adenosylmethionine (SAM) synthetase (SAMS), glutathione synthetase, methionine synthetase (MS), homocysteine transmethylase, adenosine deaminase (ADA), dihydrofolate reductase (DHFR), dihydropteroate synthetase, polyamine synthesis, S-adenosylmethionine decarboxylase (SAM-DC), ornithine decarboxylase (ODC) or arginine decarboxylase (ADC).

4. A method for killing a non-viral microorganism, comprising contacting said non-viral microorganism with an effective amount of an antimicrobial agent in combination with an amount of a methylation inhibitor effective to inhibit methylation in said non-viral microorganism; wherein said methylation inhibitor inhibits S-adenosylmethionine (SAM) synthetase (SAMS), glutathione synthetase, methionine synthetase (MS), homocysteine transmethylase, adenosine deaminase (ADA), dihydrofolate reductase (DHFR), dihydropteroate synthetase, polyamine synthesis, S-adenosylmethionine decarboxylase (SAM-DC), ornithine decarboxylase (ODC) or arginine decarboxylase (ADC).

5. A method for reducing the resistance of a non-viral microorganism to an antimicrobial agent other than AZT, comprising contacting said non-viral microorganism with an effective amount of an antimicrobial agent other than AZT in combination with an amount of a methylation inhibitor effective to inhibit methylation in said non-viral microorganism.

6. A method for reducing the resistance of a non-viral microorganism to an antimicrobial agent other than AZT, comprising selecting a methylation inhibitor, and contacting said non-viral microorganism with an effective amount of an antimicrobial agent other than AZT in combination with an amount of said inhibitor effective to inhibit methylation in said non-viral microorganism.

7. A method for killing a non-viral microorganism, comprising contacting said non-viral microorganism with an effective amount of an antimicrobial agent other than AZT in combination with an amount of a methylation inhibitor effective to inhibit methylation in said non-viral microorganism.

8. A method for killing a non-viral microorganism, comprising selecting a methylation inhibitor, and contacting said non-viral microorganism with an effective amount of an antimicrobial agent other than AZT in combination with an amount of said inhibitor effective to inhibit methylation in said non-viral microorganism.

9. A method for treating a non-viral microorganism infection, comprising administering to an animal with a non-viral microorganism infection a therapeutically effective amount of an antimicrobial agent other than AZT in combination with an amount of a methylation inhibitor effective to inhibit methylation in said non-viral microorganism.

10. A method for treating a non-viral microorganism infection, comprising selecting a methylation inhibitor, and administering to an animal with a non-viral microorganism infection a therapeutically effective amount of an antimicrobial agent other than AZT in combination with an amount of said inhibitor effective to inhibit methylation in said non-viral microorganism.

11. The method of any one of claims 5–10, wherein said non-viral microorganism is a bacterium.

12. The method of any one of claims 5–10, wherein said non-viral microorganism is a fungus.

13. The method of any one of claims 5–10, wherein said non-viral microorganism is a yeast.

14. The method of any one of claims 5–10, wherein said non-viral microorganism is a parasitic microbe.

15. The method of claim 11, wherein said non-viral microorganism is a macrolide lincosamide streptogramin B (MLS)-susceptible bacterium.

16. The method of claim 15, wherein said non-viral microorganism is an MLS-susceptible bacterium and said antimicrobial agent is a macrolide lincosamide streptogramin B (MLS) antiboiotic.

17. The method of claim 16, wherein said MLS antibiotic is a macrolide antibiotic.

18. The method of claim 17, wherein said MLS antibiotic is erythromycin, azithromycin, clarithomycin, roxithromycin, oleandomycin, spiramycin, josamycin, miocamycin, midecamycin, rosaramycin, troleandomycin, flurithromycin, rokitamycin or dirithromycin.

19. The method of claim 16, wherein said MLS antibiotic is a lincosamide antibiotic.

20. The method of claim 19, wherein said MLS antibiotic is lincomycin, clindamycin or celesticetin.

21. The method of claim 16, wherein said MLS antibiotic is a streptogramin B antibiotic.

22. The method of claim 21, wherein said MLS antibiotic is pristinamycin or virginiamycin.

23. The method of any one of claims 5–10, wherein said methylation inhibitor inhibits RNA methylation in said non-viral microorganism.

24. The method of claim 23, wherein said methylation inhibitor inhibits an RNA methyltransferase.

25. The method of claim 24, wherein said methylation inhibitor is S-adenosylhomocysteine (SAH), an SAH analogue, homocysteine, an adenine derivative, a SAM analogue, a sulphonium SAM derivative, sinefungin, a sinefungin analogue, nicotinamide, a nicotinamide analogue or polyinosinate.

26. The method of claim 25, wherein said methylation inhibitor is S-$N^6$-methyladenosylhomocysteine, S-aristeromycinyl-L-homocysteine, an S-aristeromycinyl-L-homocysteine analogue, SIBA, S-Tubercidinylhomocysteine (STH), an STH analogue, A9145c, methylnicotinamide, MTA or xylosyladenine.

27. The method of any one of claims 5–10, wherein said methylation inhibitor inhibits S-adenosylhomocysteine (SAH) hydrolase (SAHH).

28. The method of claim 27, wherein said methylation inhibitor is adenosine, an adenosine analogue, neplanocin A (NPA) or an NPA analogue.

29. The method of claim 28, wherein said methylation inhibitor is (S)-DPHA, (D)-eritadenine, (RS)-AHPA, adenosine dialdehyde, $C^3$Ado, aristeromycin (Ari), an aristeromycin analogue DHACeA, $c^3$-DHCeA, DHCaA, 3-deazaneplanocin A ($c^3$-NpcA), $c^3$- Ari, 6'methylneplanocin A, 2'deoxyadenosine, Ara-A or tubercidin.

30. The method of any one of claims 5–10, wherein said methylation inhibitor inhibits S-adenosylmethionine (SAM) synthetase (SAMS).

31. The method of claim 30, wherein said methylation inhibitor is cycloleucine, a cycloleucine analogue, a methionine analogue AMPNPP.

32. The method of claim 31, wherein said methylation inhibitor is L-cis-AMB, L-cis-AMTB or 5'(R)-(C)-[(L-homocysteine-S-yl)methyl]adenosine 5'-($\beta,\gamma$)-imidotriphosphate.

33. The method of claim 30, wherein said methylation inhibitor inhibits glutathione synthetase.

34. The method of claim 33, wherein said methylation inhibitor is buthionine sulfoximine, 7,8-dihydrofolate, $\alpha$-aminomethylglutarate or SAPH-3.

35. The method of any one of claims 5–10, wherein said methylation inhibitor inhibits methionine synthetase (MS) or homocysteine transmethylase.

36. The method of claim 35, wherein said methylation inhibitor is nitrous oxide ($N_2O$).

37. The method of any one of claims 5–10, wherein said methylation inhibitor inhibits adenosine deaminase (ADA).

38. The method of claim 37, wherein said methylation inhibitor is coformycin, a coformycin isomer, 1,6-dihydro-6-hydroxy-methylpurine nucleoside, erythro-9-(2-hydroxy-3 nonyl)adenine, 6-methylaminopurine riboside or 2'-3'-isopropylidene-adenosine.

39. The method of any one of claims 5–10, wherein said methylation inhibitor inhibits dihydrofolate reductase (DHFR).

40. The method of claim 39, wherein said methylation inhibitor is methotrexate (MTX), aminopterin, trimethoprim, a 4,6-diamino-2,2-dimethyl-s-triazine analogue or a 2,4-diamino-5-(3,4-dichlorophenyl)pyrimidine analogue.

41. The method of claim 39, wherein said methylation inhibitor is a sulfonamide inhibitor of dihydropteroate synthetase.

42. The method of any one of claims 5–10, wherein said methylation inhibitor inhibits polyamine synthesis.

43. The method of claim 42, wherein said methylation inhibitor is $\alpha$-methylornithine, 1,3-diaminopropan-2-ol, DFMO or DFMA.

44. The method of claim 42, wherein said methylation inhibitor inhibits S-adenosylmethionine decarboxylase (SAM-DC).

45. The method of claim 44, wherein said methylation inhibitor is AMA, MHZPA, MAOEA, AbeAdo, AdoMac, MGBG, CGP-39'937 or CGP-33'829.

46. The method of claim 42, wherein said methylation inhibitor inhibits ornithine decarboxylase (ODC).

47. The method of claim 42, wherein said methylation inhibitor inhibits arginine decarboxylase (ADC).

48. The method of any one of claims 5–10, wherein said methylation inhibitor inhibits RNA maturation in said non-viral microorganism.

49. The method of claim 48, wherein said methylation inhibitor is 5-azacitidine, cordycepin or toyocamycin.

50. The method of any one of claims 5–10, wherein said non-viral microorganism is located within an animal and said antimicrobial agent and said methylation inhibitor are administered to said animal in a pharmaceutically acceptable form.

51. A method for killing a non-viral microorganism, comprising contacting said non-viral microorganism with an effective amount of an antimicrobial agent in combination with an amount of a methylation inhibitor effective to inhibit methylation in said non-viral microorganism; said methylation inhibitor being selected from the group consisting of S-adenosylhomocysteine (SAH), an SAH analogue, homocysteine, an adenine derivative, a SAM analogue, a sulphonium SAM derivative, sinefungin, a sinefungin analogue, nicotinamide, a nicotinamide analogue, polyinosinate, S-$N^6$-methyladenosylhomocysteine, S-aristeromycinyl-L-homocysteine, an S-aristeromycinyl-L-homocysteine analogue, SIBA, S-Tubercidinylhomocysteine (STH), an STH analogue, A9145c, methylnicotinamide, MTA, xylosyladenine, (S)-DPHA, (D)-eritadenine, (RS)-AHPA, adenosine dialdehyde, $C^3$Ado, aristeromycin (Ari), an aristeromycin analogue, DHCeA, $c^3$-DHCeA, DHCaA, 3-deazaneplanocin A ($c^3$-NpcA), $c^3$-Ari, 6'C-methylneplanocin A, 2'deoxyadenosine, Ara-A and tubercidin.

52. A method for killing an MLS-susceptible bacterium, comprising contacting said MLS-susceptible bacterium with an effective amount of an MLS antibiotic selected from the group consisting of a macrolide, lincosamide and streptogramin B antibiotic, in combination with an amount of a methylation inhibitor effective to inhibit RNA methylation or maturation in said bacterium.

53. A method for treating a non-viral microorganism infection, comprising administering to an animal with a non-viral microorganism infection a therapeutically effective amount of an antimicrobial agent in combination with a therapeutic amount of a methylation inhibitor effective to inhibit methylation in said non-viral microorganism; said methylation inhibitor being selected from the group consisting of S-adenosylhomocysteine (SAH), an SAH analogue, homocysteine, an adenine derivative, a SAM analogue, a sulphonium SAM derivative, sinefungin, a sinefungin analogue, nicotinamide, a nicotinamide analogue, polyinosinate, S-$N^6$-methyladenosylhomocysteine, S-aristeromycinyl-L-homocysteine, an S-aristeromycinyl-L-homocysteine analogue, SIBA, S-Tubercidinylhomocysteine (STH), an STH analogue, A9145c, methylnicotinamide, MTA, xylosyladenine, (S)-DPHA, (D)-eritadenine, (RS)-AHPA, adenosine dialdehyde, $C^3$Ado, aristeromycin (Ari), an aristeromycin analogue, DHCeA, $c^3$-DHCeA, DHCaA, 3-deazaneplanocin A ($c^3$-NpcA), $c^3$-Ari, 6'C-methylneplanocin A, 2'deoxyadenosine, Ara-A and tubercidin.

54. The method of claim 9 or 10, wherein said antimicrobial agent is administered to the animal at an effective time prior to said methylation inhibitor.

55. The method of claim 9 or 10, wherein said methylation inhibitor is administered to the animal at an effective time prior to said antimicrobial agent.

56. The method of claim 9 or 10, wherein said antimicrobial agent and said methylation inhibitor are administered to the animal simultaneously.

57. The method of claim 56, wherein a single composition comprising said antimicrobial agent and said methylation inhibitor is administered to the animal.

58. The method of claim 56, wherein a first composition comprising said antimicrobial agent and a second composition comprising said methylation inhibitor are administered to the animal.

59. The method of claim 9 or 10, wherein said antimicrobial agent and said methylation inhibitor are administered in the form of a parenteral, topical, liposomal, nasal or ophthalmic preparation.

60. The method of claim 9 or 10, wherein said antimicrobial agent and said methylation inhibitor are administered orally.

61. The method of claim 9 or 10, wherein between two and about five distinct antimicrobial agents are administered to the animal in combination with said methylation inhibitor.

62. The method of claim 9 or 10, wherein said antimicrobial agent is administered to the animal in combination with between two and about ten distinct methylation inhibitors.

63. A method for treating an MLS bacterial infection, comprising administering to an animal with an MLS-susceptible bacterial infection a therapeutically effective amount of an MLS antibiotic selected from the group consisting of a macrolide, lincosamide and streptogramin B antibiotic, in combination with an amount of a methylation inhibitor effective to inhibit RNA methylation or maturation in said bacterium.

64. The method of any one of claims 1, 52 or 63, wherein said methylation inhibitor is SAH, an SAH analogue, homocysteine, an adenine derivative, a SAM analogue, sinefungin, a sinefungin analogue, polyinosinate, nicotinamide, adenosine, an adenosine analogue, NPA, an NPA analogue, tubercidin, cycloleucine, a cycloleucine analogue, a methionine analogue, AMPNPP, buthionine sulfoximine, 7,8-dihydrofolate, a-aminomethylglutarate, SAPH-3, $N_2O$, conformycin, a conformycin isomer, methotrexate (MTX), aminopterin, trimethoprim, α-methylornithine, 1,3-diaminopropan-2-ol, DFMO, DFMA, 5-azacitidine, cordycepin, toyocamycin, AMA, MHZPA, MAOEA, AbeAdo, AdoMac, MGBG, CGP-39'937 or CGP-33'829.

65. The method of any one of claims 1, 52 or 63, wherein said MLS antibiotic is, azithromycin, clarithromycin lincomycin or clindamycin.

66. The method of claim 18, wherein said MLS antibiotic is erythromycin.

67. The method of any one of claims 1, 52 or 63, wherein said MLS antibiotic is a macrolide antibiotic.

68. The method of claim 67, wherein said MLS antibiotic is erythromycin.

69. The method of any one of claims 1, 52 or 63, wherein said methylation inhibitor inhibits S-adenosylhomocysteinehydrolase (SAHH).

70. The method of claim 25, wherein said methylation inhibitor is S-adenosylhomocysteine (SAH) or an SAH analogue.

71. The method of claim 25, wherein said methylation inhibitor is homocysteine.

72. The method of claim 25, wherein said methylation inhibitor is an adenine derivative.

73. The method of claim 25, wherein said methylation inhibitor is a SAM analogue or a sulphonium SAM derivative.

74. The method of claim 25, wherein said methylation inhibitor is sinefungin or a sinefungin analogue.

75. The method of claim 25, wherein said methylation inhibitor is nicotinamide or a nicotinamide analogue.

76. The method of claim 25, wherein said methylation inhibitor is polyinosinate.

77. The method of claim 26, wherein said methylation inhibitor is S-$N^6$-methyladenosylhomocysteine, S-aristeromycinyl-L-homocysteine or an S-aristeromycinyl-L-homocysteine analogue.

78. The method of claim 26, wherein said methylation inhibitor is SIBA.

79. The method of claim 26, wherein said methylation inhibitor is S-Tubercidinylhomocysteine (STH) or an STH analogue.

80. The method of claim 26, wherein said methylation inhibitor is A9145c.

81. The method of claim 26, wherein said methylation inhibitor is methylnicotinamide.

82. The method of claim 27, wherein said methylation inhibitor is MTA.

83. The method of claim 27, wherein said methylation inhibitor is xylosyladenine.

84. The method of claim 29, wherein said methylation inhibitor is (S)-DPHA or (RS)-AHPA.

85. The method of claim 29, wherein said methylation inhibitor is (D)-eritadenine.

86. The method of claim 29, wherein said methylation inhibitor is adenosine dialdehyde or 2'deoxyadenosine.

87. The method of claim 29, wherein said methylation inhibitor is $C^3$Ado.

88. The method of claim 29, wherein said methylation inhibitor is aristeromycin (Ari), an aristeromycin analogue or $c^3$-Ari.

89. The method of claim 29, wherein said methylation inhibitor is DHCeA, $c^3$-DHCeA, or DHCaA.

90. The method of claim 29, wherein said methylation inhibitor is 3-deazaneplanocin A ($c^3$-NpcA), 6'C-methylneplanocin A or Ara-A.

91. The method of claim 29, wherein said methylation inhibitor is tubercidin.

92. The method of claim 31, wherein said methylation inhibitor is cycloleucine or a cycloleucine analogue.

93. The method of claim 31, methylation inhibitor is a methionine analogue.

94. The method of claim 31, methylation inhibitor is AMPNPP.

95. The method of claim 32, wherein said methylation inhibitor is L-cis-AMB or L-cis-AMTB.

96. The method of claim 32, wherein said methylation inhibitor is 5'(R)-(C)-[(L-homocysteine-S-yl)methyl] adenosine 5'-($\beta,\gamma$)-imidotriphosphate.

97. The method of claim 34, wherein said methylation inhibitor is buthionine sulfoximine.

98. The method of claim 34, wherein said methylation inhibitor is 7,8-dihydrofolate.

99. The method of claim 34, wherein said methylation inhibitor is $\alpha$-aminomethylglutarate.

100. The method of claim 34, wherein said methylation inhibitor is SAPH-3.

101. The method of claim 38, wherein said methylation inhibitor is coformycin or a coformcyin isomer.

102. The method of claim 38, wherein said methylation inhibitor is 1,6-dihydro-6-hydroxy-methylpurine nucleoside.

103. The method of claim 38, wherein said methylation inhibitor is erythro-9-(2-hydroxy-3 nonyl)adenine.

104. The method of claim 38, wherein said methylation inhibitor is 6-methylaminopurine riboside.

105. The method of claim 38, wherein said methylation inhibitor is 2'-3'-isopropylidene-adenosine.

106. The method of claim 40, wherein said methylation inhibitor is methotrexate (MTX).

107. The method of claim 40, wherein said methylation inhibitor is aminopterin.

108. The method of claim 40, wherein said methylation inhibitor is trimethoprim.

109. The method of claim 40, wherein said methylation inhibitor is a 4,6-diamino-2,2-dimethyl-s-triazine analogue or a 2,4-diamino-5-(3,4-dichlorophenyl)pyrimidine analogue.

110. The method of claim 43, wherein said methylation inhibitor is $\alpha$-methylornithine.

111. The method of claim 43, wherein said methylation inhibitor is 1,3-diaminopropan-2ol.

112. The method of claim 43, wherein said methylation inhibitor is DFMO or DFMA.

113. The method of claim 43, wherein said methylation inhibitor is AMA.

114. The method of claim 45, wherein said methylation inhibitor is MHZPA.

115. The method of claim 45, wherein said methylation inhibitor is MAOEA.

116. The method of claim 45, wherein said methylation inhibitor is AbeAdo.

117. The method of claim 45, wherein said methylation inhibitor is AdoMac.

118. The method of claim 45, wherein said methylation inhibitor is MGBG.

119. The method for treating a non-viral microorganism infection, comprising administering to an animal with a non-viral microorganism infection a therapeutically effective amount of an antimicrobial agent in combination with a therapeutic amount of a methylation inhibitor effective to inhibit methylation in said non-viral microorganism; wherein said methylation inhibitor inhibits S-adenosylmethionine (SAM) synthetase (SAMS), glutathione synthetase, methionine synthetase (MS), homocysteine transmethylase, adenosine deaminase (ADA), dihydrofolate reductase (DHFR), dihydropteroate synthetase, polyamine synthesis, S-adenosylmethionine decarboxylase (SAM-DC), ornithine decarboxylase (ODC) or arginine decarboxylase (ADC).

120. The method of any one of claims 3, 4 or 119, wherein said methylation inhibitor inhibits S-adenosylmethionine (SAM) synthetase (SAMS).

121. The method of any one of claims 3, 4 or 119, wherein said methylation inhibitor inhibits glutathione synthetase.

122. The method of any one of claims 3, 4 or 119, wherein said methylation inhibitor inhibits methionine synthetase (MS) or homocysteine transmethylase.

123. The method of any one of claims 3, 4 or 119, wherein said methylation inhibitor inhibits adenosine deaminase (ADA).

124. The method of any one of claims 3, 4 or 119, wherein said methylation inhibitor inhibits dihydrofolate reductase (DHFR).

125. The method of any one of claims 3, 4 or 119, wherein said methylation inhibitor is a sulfonamide inhibitor of dihydropteroate synthetase.

126. The method of any one of claims 3, 4 or 119, wherein said methylation inhibitor inhibits polyamine synthesis.

127. The method of any one of claims 3, 4 or 119, wherein said methylation inhibitor inhibits S-adenosylmethionine decarboxylase (SAM-DC).

128. The method of any one of claims 3, 4 or 119, wherein said methylation inhibitor inhibits ornithine decarboxylase (ODC).

129. The method of any one of claims 3, 4 or 119, wherein said methylation inhibitor inhibits arginine decarboxylase (ADC).

130. The method of claim 90, wherein said methylation inhibitor is 3-deazaneplanocinA ($c^3$-NpcA).

131. The method of claim 45, wherein said methylation inhibitor is CGP-39'937 or CGP-33'829.

132. The method of claim 64, wherein said methylation inhibitor is 3-deazaneplanocinA ($c^3$-NpcA).

* * * * *

UNITED STATES PATENT AND TRADEMARK OFFICE
CERTIFICATE OF CORRECTION

PATENT : 5,872,104                                Page 1 of 6
DATED : February 16, 1999
INVENTOR(S) : Vermeulen et al.

It is certified that error appears in the above-identified patent and that said Letters Patent is hereby corrected as shown below:

On the title page, under item [56] References Cited, Other Publications, insert the following:

---

Avila et al., "Sinefungin as Treatment for American *Leishmania* in Sensitive BALB/c and Resistant C57BL/6 Mice," *Am. J. Trop. Med. Hyg.*, 43(2):139-145, 1990.

Barbés et al., "Effects of Sinefungin and S-adenosylhomocysteine on DNA and Protein Methyltransferases from *Streptomyces* and Other Bacteria," *FEMS Microbiology Letters*, 69:239-244, 1990.

Borchardt et al., "Neplanocin A, A Potent Inhibitor of S-adenosylhomocysteine Hydrolase and of Vaccinia Virus Multiplication in Mouse L929 Cells," *J. Biol. Chem.*, 259(7):4353-4358, 1984.

Busby, "Molecular Basis of Antibiotic Resistance," Molecular Diagnostics, Rapley & Walker, Blackwell Sci. Pubs., London, Ch. 24, pp. 371-381, 1993.

Davies, "Inactivation of Antibiotics and the Dissemination of Resistance Genes," *Science*, 264:375-382, 1994.

De Clercq & Cools, "Antiviral Potency of Adenosine Analogues: Correlation with Inhibition of S-adenosylhomocysteine Hydrolase," *Biochemical and Biophysical Research Communications*, 129(1):306-311, 1985.

De Clercq, "Targets for the Antiviral and Antitumor Activities of Nucleoside, Nucleotide and Oligonucleotide Analogues," *Nucleosides & Nucleotides*, 4(1&2):3-11, 1985.

De Clercq, "S-adenosylhomocysteine Hydrolase Inhibitors as Broad-Spectrum Antiviral Agents," *Biochemical Pharmacology*, 36(16):2567-2575, 1987.

UNITED STATES PATENT AND TRADEMARK OFFICE
CERTIFICATE OF CORRECTION

PATENT : 5,872,104

DATED : February 16, 1999

INVENTOR(S) : Vermeulen et al.

It is certified that error appears in the above-identified patent and that said Letters Patent is hereby corrected as shown below:

On the title page, under item [56] References Cited, Other Publications, insert the following:

---

De Clercq et al., "Broad-Spectrum Antiviral activities of Neplanocin A, 3-Deazaneplanocin A, and Their 5'-Nor Derivatives," *Antimicrobial Agents and Chemotherapy*, 33(8):1291-1297, 1989.

Dubnau, "Translational Attenuation: The Regulation of Bacterial Resistance to the Macrolide-Lincosamide-Streptogramin B Antibiotics," *CRC Critical Reviews in Biochemistry*, 16(2):103-132, 1983.

Eliopoulos & Moellering, "Antimicrobial Combinations," *Antibiotics in Laboratory Medicine*, Ch. 13, pp. 432-492, 1991.

Glazer et al., "3-Deazaneplanocin A: A New Inhibitor of S-adenosylhomocysteine Synthesis and its Effects in Human Colon Carcinoma Cells," *Biochemical Pharmacology*, 35(24):4523-4527, 1986.

Glazer & Knode, "Neplanocin A, A Cyclopentenyl Analog of Adenosine with Specificity for Inhibiting RNA Methylation," *J. Biol. Chem.*, 259(21):12964-12969, 1984.

Horinouchi & Weisblum, "Posttranscriptional modification of mRNA conformation: mechanism that regulates erythromycin induced resistance," *Proc. Natl. Acad. Sci. USA*, 77(12):7079-7083, 1980.

Horinouchi et al., "A Complex Attenuator Regulates Inducible Resistance to Macrolides, Lincosamides, and Streptogramin Type B Antibiotics in *Streptococcus sanguis*," *J. of Bacteriology*, 154(3):1252-1262, 1983.

Lai & Weisblum, "Altered Methylation of Ribosomal RNA in an Erythromycin-Resistant Strain of *Staphylococcus aureus*," *Proc. Nat. Acad. Sci. USA*, 68(4):856-860, 1971.

UNITED STATES PATENT AND TRADEMARK OFFICE
CERTIFICATE OF CORRECTION

PATENT : 5,872,104  
DATED : February 16, 1999  
INVENTOR(S) : Vermeulen et al.

Page 3 of 6

It is certified that error appears in the above-identified patent and that said Letters Patent is hereby corrected as shown below:

On the title page, under item [56] References Cited, Other Publications, insert the following:

---

Lawrence & Robert-Gero, "Distribution of Macromolecular Methylations in Promastigotes of *Leishmania donovani* and Impact of Sinefungin," *J. Euk. Microbiol.*, 40(5)-581-589, 1993.

Leclercq & Courvalin, "Bacterial Resistance to Macrolide, Lincosamide, and Streptogramin Antibiotics by Target Modification," *Antimicrobial Agents and Chemotherapy*, 35(7):1267-1272, 1991.

Lhoest & Colson, "Ribosomal Protein Methylation," Protein Methylation, Chapter 9:155-178, 1990.

Lombardini & Sufrin, "Chemotherapeutic Potential of Methionine Analogue Inhibitors of Tumor-Derived Methionine Adenosyltransferases," *Biochemical Pharmacology*, 32(3):489-495, 1983.

Moore, "Differential Inhibition of Bacterial tRNA Methylases by S-adenosylethionine and Other Adenine Derivatives," *Canadian Journal of Biochemistry*, 48:702-705, 1970.

Nikaido, "Prevention of Drug Access to Bacterial Targets: Permeability Barriers and Active Efflux," *Science*, 264:382-388, 1994.

O'Dwyer et al., "2'-Deoxycoformycin (Pentostatin) for Lymphoid Malignancies," *Annals of Internal Medicine*, 108:733-743, 1988.

Ranzini & Dubin, "The 'Erythromycin-Resistance' Methylated Sequence of *Staphylococcus aureus* Ribosomal RNA," *Plasmid*, 10:293-295, 1983.

UNITED STATES PATENT AND TRADEMARK OFFICE
CERTIFICATE OF CORRECTION

PATENT : 5,872,104

DATED : February 16, 1999

INVENTOR(S) : Vermeulen et al.

It is certified that error appears in the above-identified patent and that said Letters Patent is hereby corrected as shown below:

On the title page, under item [56] References Cited, Other Publications, insert the following:

---

Skinner et al., "Site of Action of a Ribosomal RNA Methylase Responsible for Resistance to Erythromycin and Other Antibiotics," *J. Biol. Chem.*, 258(20):12702-12706, 1983.

Spratt, "Resistance to Antibiotics Mediated by Target Alterations," *Science*, 264:388-393, 1994.

Sufrin et al., "Differential Kinetic Properties of L-2-amino-4-methylthio-*cis*-but-3-enoic acid, a methionine Analog Inhibitor of *S*-adenosylmethionine Synthetase," *Biochimica et Biophysica Acta*, 1202:87-91, 1993.

Suhadolnik, "Naturally Occurring Nucleoside and Nucleotide Antibiotics," *Progress in Nucleic Acid Research and Molecular Biology*," 22:193-291, 1979.

Thakker-Varia et al., "Ribosomal RNA Methylation in *Staphylococcus aureus* and *Escherichia coli*: Effect of the 'MLS' (Erythromycin Resistance) Methylase," *Plasmid*, 14:152-161, 1985.

Travis, "Reviving the Antibiotic Miracle?", *Science*, 264:360-362, 1994.

Tseng et al., "Synthesis of 3-Deazaneplanocin A, a Powerful Inhibitor of *S*-Adenosylhomocysteine Hydrolase with Potent and Selective *in Vitro* and *In Vivo* Antiviral Activities," *J. Med. Chem.*, 32:1442-1446, 1989.

Tyms et al., "Polyamine Inhibitors in Antimicrobial Chemotherapy," *Journal of Antimicrobial Chemotherapy*, 22:403-427, 1988.

UNITED STATES PATENT AND TRADEMARK OFFICE
CERTIFICATE OF CORRECTION

PATENT : 5,872,104

DATED : February 16, 1999

INVENTOR(S) : Vermeulen et al.

It is certified that error appears in the above-identified patent and that said Letters Patent is hereby corrected as shown below:

On the title page, under item [56] References Cited, Other Publications, insert the following:

| |
|---|
| Vedel & Robert-Géro, "Comparative Effect of S-Adenosyl-Homocysteine (SAH) and Sinefungin on tRNA-bae Methylation in Whole Cells and *In Vitro*," *FEBS Letters*, 128(1):87-89, 1981. |
| Wainfan & Borek, "Differential Inhibitors of tRNA Methylases," *Mol. Pharmacol.*, 3:595-598, 1967. |
| Weisblum, "Inducible Erythromycin Resistance in Bacteria," *British Medical Bulletin*, 40(1):47-53, 1984. |
| Whaun et al., "Antimalarial Activity of Neplanocin A with Perturbations in the Metabolism of Purines, Polyamines and S-Adenosylmethionine," *Journal Pharmacology and Experimental Therapeutics*, 236(1):277-283, 1986. |
| Wolfe & Borchardt, "S-Adenosyl-L-homocysteine Hydrolase as a Target for Antiviral Chemotherapy," *Journal of Medicinal Chemistry*, 34(5):1521-1530, 1991. |

UNITED STATES PATENT AND TRADEMARK OFFICE
CERTIFICATE OF CORRECTION

PATENT : 5,872,104

DATED : February 16, 1999

INVENTOR(S) : Vermeulen et al.

It is certified that error appears in the above-identified patent and that said Letters Patent is hereby corrected as shown below:

On the title page, under item [56] References Cited, Other Publications,
insert the following:

---

Yebra *et al.*, "The Effect of Sinefungin and Synthetic Analogues on RNA and DNA Methyltransferases from *Streptomyces*," *J. Antibiotics*, 44(10):1141-1147, 1991.

Zalacain & Cundliffe, "Methylation of 23S Ribosomal RNA Due to *carB*, an Antibiotic-resistance Determinant from the Carbomycin Producer, *Streptomyces thermotolerans*," *Eur. J. Biochem.*, 189:67-72, 1990.

---

Signed and Sealed this

Sixteenth Day of November, 1999

*Attest:*

Q. TODD DICKINSON

*Attesting Officer*  *Acting Commissioner of Patents and Trademarks*

UNITED STATES PATENT AND TRADEMARK OFFICE
CERTIFICATE OF CORRECTION

PATENT NO. : 5,872,104  
APPLICATION NO. : 08/364246  
DATED : February 16, 1999  
INVENTOR(S) : Vermeulen et al.

Page 1 of 5

It is certified that error appears in the above-identified patent and that said Letters Patent is hereby corrected as shown below:

Please delete old claims and rekey new claims from column 85-92.

Signed and Sealed this

Tenth Day of October, 2006

JON W. DUDAS  
*Director of the United States Patent and Trademark Office*

What is claimed is:

1. A method for reducing the resistance of a non-viral microorganism to an antimicrobial agent other than AZT, comprising contacting said non-viral microorganism with an effective amount of an antimicrobial agent other than AZT in combination with an amount of a methylation inhibitor effective to inhibit methylation in said non-viral microorganism.

2. A method for reducing the resistance of a non-viral microorganism to an antimicrobial agent other than AZT, comprising selecting a methylation inhibitor, and contacting said non-viral microorganism with an effective amount of an antimicrobial agent other than AZT in combination with an amount of said inhibitor effective to inhibit methylation in said non-viral microorganism.

3. A method for killing a non-viral microorganism, comprising contacting said non-viral microorganism with an effective amount of an antimicrobial agent other than AZT in combination with an amount of a methylation inhibitor effective to inhibit methylation in said non-viral microorganism.

4. A method for killing a non-viral microorganism, comprising selecting a methylation inhibitor, and contacting said non-viral microorganism with an effective amount of an antimicrobial agent other than AZT in combination with an amount of said inhibitor effective to inhibit methylation in said non-viral microorganism.

5. A method for treating a non-viral microorganism infection, comprising administering to an animal with a non-viral microorganism infection a therapeutically effective amount of an antimicrobial agent other than AZT in combination with an amount of a methylation inhibitor effective to inhibit methylation in said non-viral microorganism.

6. A method for treating a non-viral microorganism infection, comprising selecting a methylation inhibitor, and administering to an animal with a non-viral microorganism infection a therapeutically effective amount of an antimicrobial agent other than AZT in combination with an amount of said inhibitor effective to inhibit methylation in said non-viral microorganism.

7. The method of any one of claims 1–4, wherein said non-viral microorganism is located within an animal and said antimicrobial agent and said methylation inhibitor are administered to said animal in a pharmaceutically acceptable form.

8. The method of any one of claims 1–6, wherein said non-viral microorganism is a fungus.

9. The method of any one of claims 1–6, wherein said non-viral microorganism is a yeast.

10. The method of any one of claims 1–6, wherein said non-viral microorganism is a parasitic microbe.

11. The method of any one of claims 1–6, wherein said non-viral microorganism is a bacterium.

12. The method of claim 11, wherein said non-viral microorganism is a macrolide lincosamide streptogramin B (MLS)-susceptible bacterium.

13. The method of claim 12, wherein said non-viral microorganism is an MLS-susceptible bacterium and said antimicrobial agent is a macrolide lincosamide streptogramin B (MLS) antibiotic.

14. The method of claim 13, wherein said MLS antibiotic is a macrolide antibiotic.

15. The method of claim 14, wherein said MLS antibiotic is erythromycin, azithromycin, clarithromycin, roxithromycin, oleandomycin, spiramycin, josamycin, miocamycin, midecamycin, rosaramycin, troleandomycin, flurithromycin, rokitamycin or dirithromycin.

16. The method of claim 15, wherein said MLS antibiotic is erythromycin.

17. The method of claim 13, wherein said MLS antibiotic is a lincosamide antibiotic.

18. The method of claim 17, wherein said MLS antibiotic is lincomycin, clindamycin or celesticetin.

19. The method of claim 14, wherein said MLS antibiotic is a streptogramin B antibiotic.

20. The method of claim 19, wherein said MLS antibiotic is pristinamycin or virginiamycin.

21. The method of any one of claims 1–6, wherein said methylation inhibitor inhibits RNA methylation in said non-viral microorganism.

22. The method of claim 21, wherein said methylation inhibitor inhibits an RNA methyltransferase.

23. The method of claim 22, wherein said methylation inhibitor is S-adenosylhomocysteine (SAH), an SAH analogue, homocysteine, an adenine derivative, a SAM analogue, a sulphonium SAM derivative, sinefungin, a sinefungin analogue, nicotinamide, a nicotinamide analogue or polyinosinate.

24. The method of claim 23, wherein said methylation inhibitor is S-adenosylhomocysteine (SAH) or an SAH analogue.

25. The method of claim 23, wherein said methylation inhibitor is homocysteine.

26. The method of claim 23, wherein said methylation inhibitor is an adenine derivative.

27. The method of claim 23, wherein said methylation inhibitor is a SAM analogue or a sulphonium SAM derivative.

28. The method of claim 23, wherein said methylation inhibitor is sinefungin or a sinefungin analogue.

29. The method of claim 23, wherein said methylation inhibitor is nicotinamide or a nicotinamide analogue.

30. The method of claim 23, wherein said methylation inhibitor is polyinosinate.

31. The method of claim 23, wherein said methylation inhibitor is $S-N^6$-methyladenosylhomocysteine, S-aristeromycinyl-L-homocysteine, an S-aristeromycinyl-L-homocysteine analogue, SIBA, S-Tubercidinylhomocysteine (STH), an STH analogue, A9145c, methylnicotinamide, MTA or xylosyladenine.

32. The method of claim 31, wherein said methylation inhibitor is $S-N^6$-methyladenosylhomocysteine, S-aristeromycinyl-L-homocysteine or an S-aristeromycinyl-L-homocysteine analogue.

33. The method of claim 31, wherein said methylation inhibitor is SIBA.

34. The method of claim 31, wherein said methylation inhibitor is S-Tubercidinylhomocysteine (STH) or an STH analogue.

35. The method of claim 31, wherein said methylation inhibitor is A9145c.

36. The method of claim 31, wherein said methylation inhibitor is methylnicotinamide.

37. The method of claim 31, wherein said methylation inhibitor is MTA.

38. The method of claim 31, wherein said methylation inhibitor is xylosyladenine.

39. The method of any one of claims 1–6, wherein said methylation inhibitor inhibits S-adenosylhomocysteine (SAH) hydrolase (SAHH).

40. The method of claim 39, wherein said methylation inhibitor is adenosine, an adenosine analogue, neplanocin A (NPA) or an NPA analogue.

41. The method of claim 40, wherein said methylation inhibitor is (S)-DPHA, (D)-eritadenine, (RS)-AHPA, adenosine dialdehyde, C³Ado, aristeromycin (Ari), an aristeromycin analogue, DHCeA, c³-DHCeA, DHCaA, 3-deazaneplanocin A (c³-NpcA), c³-Ari, 6'C-methylneplanocin A, 2'deoxyadenosine, Ara-A or tubercidin.

42. The method of claim 41, wherein said methylation inhibitor is (S)-DPHA or (R,S)-AHPA.

43. The method of claim 41, wherein said methylation inhibitor is (D)-eritadenine.

44. The method of claim 41, wherein said methylation inhibitor is adenosine dialdehyde or 2'deoxyadenosine.

45. The method of claim 41, wherein said methylation inhibitor is C³Ado.

46. The method of claim 41, wherein said methylation inhibitor is aristeromycin (Ari), an aristeromycin analogue or c³-Ari.

47. The method of claim 41, wherein said methylation inhibitor is DHCeA, c³-DHCeA, or DHCaA.

48. The method of claim 41, wherein said methylation inhibitor is 3-deazaneplanocin A (c³-NpcA), 6'C-methylneplanocin A or Ara-A.

49. The method of claim 48, wherein said methylation inhibitor is 3-deazaneplanocin A (c³-NpcA).

50. The method of claim 41, wherein said methylation inhibitor is tubercidin.

51. The method of any one of claims 1–6, wherein said methylation inhibitor inhibits S-adenosylmethionine (SAM) synthetase (SAMS).

52. The method of claim 51, wherein said methylation inhibitor is cycloleucine, a cycloleucine analogue, a methionine analogue or AMPNPP.

53. The method of claim 52, wherein said methylation inhibitor is cycloleucine or a cycloleucine analogue.

54. The method of claim 52, wherein said methylation inhibitor is a methionine analogue.

55. The method of claim 52, wherein said methylation inhibitor is AMPNPP.

56. The method of claim 52, wherein said methylation inhibitor is L-cis-AMB, L-cis-AMTB or 5'(R)-(C)-[(L-homocysteine-S-yl) methyl]adenosine 5'-(β,γ)-imidotriphosphate.

57. The method of claim 56, wherein said methylation inhibitor is L-cis-AMB or L-cis-AMTB.

58. The method of claim 56, wherein said methylation inhibitor is 5'(R)-(C)-[(L-homocysteine-S-yl) methyl]adenosine 5'-(β,γ)-imidotriphosphate.

59. The method of claim 51, wherein said methylation inhibitor inhibits glutathione synthetase.

60. The method of claim 59, wherein said methylation inhibitor is buthionine sulfoximine, 7,8-dihydrofolate, α-aminomethylglutarate or SAPH-3.

61. The method of claim 60, wherein said methylation inhibitor is buthionine sulfoximine.

62. The method of claim 60, wherein said methylation inhibitor is 7,8-dihydrofolate.

63. The method of claim 60, wherein said methylation inhibitor is α-aminomethylglutarate.

64. The method of claim 60, wherein said methylation inhibitor is SAPH-3.

65. The method of any one of claims 1–6, wherein said methylation inhibitor inhibits methionine synthetase (MS) or homocysteine tansmethylase.

66. The method of claim 65, wherein said methylation inhibitor is nitrous oxide (N₂O).

67. The method of any one of claims 1–6, wherein said methylation inhibitor inhibits adenosine deaminase (ADA).

68. The method of claim 67, wherein said methylation inhibitor is coformycin, a coformycin isomer, 1,6-dihydro-6-hydroxy-methylpurine nucleoside, erythro-9-(2-hydroxy-3 nonyl)adenine, 6-methylaminopurine riboside or 2'-3'-isopropylidene-adenosine.

69. The method of claim 68, wherein said methylation inhibitor is coformycin or a coformycin isomer.

70. The method of claim 68, wherein said methylation inhibitor is 1,6-dihydro-6-hydroxy-methylpurine nucleoside.

71. The method of claim 68, wherein said methylation inhibitor is erythro-9-(2-hydroxy-3 nonyl)adenine.

72. The method of claim 68, wherein said methylation inhibitor is 6-methylaminopurine riboside.

73. The method of claim 68, wherein said methylation inhibitor is 2'-3'-isopropylidene-adenosine.

74. The method of any one of claims 1–6, wherein said methylation inhibitor inhibits dihydrofolate reductase (DHFR).

75. The method of claim 74, wherein said methylation inhibitor is methotrexate (MTX), aminopterin, trimethoprim, a 4,6-diamino-2,2-dimethyl-s-triazine analogue or a 2,4-diamino-5-(3,4-dichlorophenyl)pyrimidine analogue.

76. The method of claim 75, wherein said methylation inhibitor is methotrexate (MTX).

77. The method of claim 75, wherein said methylation inhibitor is aminopterin.

78. The method of claim 75, wherein said methylation inhibitor is trimethoprim.

79. The method of claim 75, wherein said methylation inhibitor is a 4,6-diamino-2,2-dimethyl-s-triazine analogue or a 2,4-diamino-5-(3,4-dichlorophenyl)pyrimidine analogue.

80. The method of claim 74, wherein said methylation inhibitor is a sulfonamide inhibitor of dihydropteroate synthetase.

81. The method of any one of claims 1–6, wherein said methylation inhibitor inhibits polyamine synthesis.

82. The method of claim 81, wherein said methylation inhibitor is α-methylornithine, 1,3-diaminopropan-2-ol, DFMO or DFMA.

83. The method of claim 82, wherein said methylation inhibitor is α-methylornithine.

84. The method of claim 82, wherein said methylation inhibitor is 1,3-diaminopropan-2-ol.

85. The method of claim 82, wherein said methylation inhibitor is DFMO or DFMA.

86. The method of claim 81, wherein said methylation inhibitor inhibits S-adenosylmethionine decarboxylase (SAM-DC).

87. The method of claim 86, wherein said methylation inhibitor is AMA, MHZPA, MAOEA, AbeAdo, AdoMac, MGBG, CGP-39'937 or CGP-33'829.

88. The method of claim 87, wherein said methylation inhibitor is AMA.

89. The method of claim 87, wherein said methylation inhibitor is MHZPA.

90. The method of claim 87, wherein said methylation inhibitor is MAOEA.

91. The method of claim 87, wherein said methylation inhibitor is AbeAdo.

92. The method of claim 87, wherein said methylation inhibitor is AdoMac.

93. The method of claim 87, wherein said methylation inhibitor is MGBG.

94. The method of claim 87, wherein said methylation inhibitor is CGP-39'937 or CGP-33'829.

95. The method of claim 81, wherein said methylation inhibitor inhibits ornithine decarboxylase (ODC).

96. The method of claim 81, wherein said methylation inhibitor inhibits arginine decarboxylase (ADC).

97. The method of any one of claims 1–6, wherein said methylation inhibitor inhibits RNA maturation in said non-viral microorganism.

98. The method of claim 97, wherein said methylation inhibitor is 5-azacitidine, cordycepin or toyocamycin.

99. The method of claim 5 or 6, wherein said antimicrobial agent is administered to the animal at an effective time prior to said methylation inhibitor.

100. The method of claim 5 or 6, wherein said methylation inhibitor is administered to the animal at an effective time prior to said antimicrobial agent.

101. The method of claim 5 or 6, wherein said antimicrobial agent and said methylation inhibitor are administered to the animal simultaneously.

102. The method of claim 101, wherein a single composition comprising said antimicrobial agent and said methylation inhibitor is administered to the animal.

103. The method of claim 101, wherein a first composition comprising said antimicrobial agent and a second composition comprising said methylation inhibitor are administered to the animal.

104. The method of claim 5 or 6, wherein said antimicrobial agent and said methylation inhibitor are administered in the form of a parenteral, topical, liposomal, nasal or ophthalmic preparation.

105. The method of claim 5 or 6, wherein said antimicrobial agent and said methylation inhibitor are administered orally.

106. The method of claim 5 or 6, wherein between two and about five distinct antimicrobial agents are administered to the animal in combination with said methylation inhibitor.

107. The method of claim 5 or 6, wherein said antimicrobial agent is administered to the animal in combination with between two and about ten distinct methylation inhibitors.

108. A method for reducing the resistance of a non-viral microorganism to an antimicrobial agent, comprising contacting said non-viral microorganism with an effective amount of said antimicrobial agent in combination with an amount of a methylation inhibitor effective to inhibit methylation in said non-viral microorganism; wherein said methylation inhibitor inhibits S-adenosylmethionine (SAM) synthetase (SAMS), glutathione synthetase, methionine synthetase (MS), homocysteine transmethylase, adenosine deaminase (ADA), dihydrofolate reductase (DHFR), dihydropteroate synthetase, polyamine synthesis, S-adenosylmethionine decarboxylase (SAM-DC), ornithine decarboxylase (ODC) or arginine decarboxylase (ADC).

109. A method for killing a non-viral microorganism, comprising contacting said non-viral microorganism with an effective amount of an antimicrobial agent in combination with an amount of a methylation inhibitor effective to inhibit methylation in said non-viral microorganism; wherein said methylation inhibitor inhibits S-adenosylmethionine (SAM) synthetase (SAMS), glutathione synthetase, methionine synthetase (MS), homocysteine transmethylase, adenosine deaminase (ADA), dihydrofolate reductase (DHFR), dihydropteroate synthetase, polyamine synthesis, S-adenosylmethionine decarboxylase (SAM-DC), ornithine decarboxylase (ODC) or arginine decarboxylase (ADC).

110. A method for treating a non-viral microorganism infection, comprising administering to an animal with a non-viral microorganism infection a therapeutically effective amount of an antimicrobial agent in combination with a therapeutic amount of a methylation inhibitor effective to inhibit methylation in said non-viral microorganism; wherein said methylation inhibitor inhibits S-adenosylmethionine (SAM) synthetase (SAMS), glutathione synthetase, methionine synthetase (MS), homocysteine transmethylase, adenosine deaminase (ADA), dihydrofolate reductase (DHFR), dihydropteroate synthetase, polyamine synthesis, S-adenosylmethionine decarboxylase (SAM-DC), ornithine decarboxylase (ODC) or arginine decarboxylase (ADC).

111. The method of any one of claims 108, 109 or 110, wherein said methylation inhibitor inhibits S-adenosylmethionine (SAM) synthetase (SAMS).

112. The method of any one of claims 108, 109 or 110, wherein said methylation inhibitor inhibits glutathione synthetase.

113. The method of any one of claims 108, 109 or 110, wherein said methylation inhibitor inhibits methionine synthetase (MS) or homocysteine transmethylase.

114. The method of any one of claims 108, 109 or 110, wherein said methylation inhibitor inhibits adenosine deaminase (ADA).

115. The method of any one of claims 108, 109 or 110, wherein said methylation inhibitor inhibits dihydrofolate reductase (DHFR).

116. The method of any one of claims 108, 109 or 110, wherein said methylation inhibitor is a sulfonamide inhibitor of dihydropteroate synthetase.

117. The method of any one of claims 108, 109 or 110, wherein said methylation inhibitor inhibits polyamine synthesis.

118. The method of any one of claims 108, 109 or 110, wherein said methylation inhibitor inhibits S-adenosylmethionine decarboxylase (SAM-DC).

119. The method of any one of claims 108, 109 or 110, wherein said methylation inhibitor inhibits ornithine decarboxylase (ODC).

120. The method of any one of claims 108, 109 or 110, wherein said methylation inhibitor inhibits arginine decarboxylase (ADC).

121. A method for reducing the resistance of a non-viral microorganism to an antimicrobial agent, comprising contacting said non-viral microorganism with an effective amount of said antimicrobial agent in combination with an amount of a methylation inhibitor effective to inhibit methylation in said non-viral microorganism; said methylation inhibitor being selected from the group consisting of S-adenosylhomocysteine (SAH), an SAH analogue, homocysteine, an adenine derivative, a SAM analogue, a sulphonium SAM derivative, sinefungin, a sinefungin analogue, nicotinamide, a nicotinamide analogue, polyinosinate, S-$N^6$-methyladenosylhomocysteine, S-aristeromycinyl-L-homocysteine, an S-aristeromycinyl-L-homocysteine analogue, SIBA, S-Tubercidinylhomocysteine (STH), an STH analogue, A9145c, methylnicotinamide, MTA, xylosyladenine, (S)-DPHA, (D)-eritadenine, (RS)-AHPA, adenosine dialdehyde, $C^3$Ado, aristeromycin (Ari), an aristeromycin analogue, DHCeA, $c^3$-DHCeA, DHCaA, 3-deazaneplanocin A ($c^3$-NpcA), $c^3$-Ari. 6'C-methylneplanocin A, 2'deoxyadenosine, Ara-A and tubercidin.

122. A method for killing a non-viral microorganism, comprising contacting said non-viral microorganism with an effective amount of an antimicrobial agent in combination with an amount of a methylation inhibitor effective to inhibit methylation in said non-viral microorganism; said methylation inhibitor being selected from the group consisting of S-adenosylhomocysteine (SAH), an SAH analogue, homocysteine, an adenine derivative, a SAM analogue, a sulphonium SAM derivative, sinefungin, a sinefungin analogue, nicotinamide, a nicotinamide analogue, polyinosinate, S-N-$^6$-methyladenosylhomocysteine, S-aristeromycinyl-L-homocysteine, an S-aristeromycinyl-L-homocysteine analogue, SIBA, S-Tubercidinylhomocysteine (STH), an STH analogue, A9145c, methylnicotinamide, MTA, xylosyladenine, (S)-DPHA, (D)-eritadenine, (RS)-AHPA, adenosine dialdehyde, $C^3$-Ado, aristeromycin (Ari), an aristeromycin analogue, DHCeA, $c^3$-DHCeA, DHCaA, 3-deazaneplanocin A ($c^3$-NpcA), $c^3$-Ari, 6'C-methylneplanocin A, 2'deoxyadenosine, Ara-A and tubercidin.

123. A method for treating a non-viral microorganism infection, comprising administering to an animal with a non-viral microorganism infection a therapeutically effective amount of an antimicrobial agent in combination with a therapeutic amount of a methylation inhibitor effective to inhibit methylation in said non-viral microorganism; said methylation inhibitor being selected from the group consisting of S-adenosylhomocysteine (SAH), an SAH analogue, homocysteine, an adenine derivative, a SAM analogue, a sulphonium SAM derivative, sinefungin, a sinefungin analogue, nicotinamide, a nicotinamide analogue, polyinosinate, S-N$^6$-methyladenosylhomocysteine, S-aristeromycinyl-L-homocysteine, an S-aristeromycinyl-L-homocysteine analogue, SIBA, S-Tubercidinylhomocysteine (STH), an STH analogue, A9145c, methylnicotinamide, MTA, xylosyladenine, (S)-DPHA, (D)-eritadenine, (RS)-AHPA, adenosine dialdehyde, $C^3$-Ado, aristeromycin (Ari), an aristeromycin analogue, DHCeA, $c^3$-DHCeA, DHCaA, 3-deazaneplanocin A ($c^3$-NpcA), $c^3$-Ari, 6'C-methylneplanocin A, 2'deoxyadenosine, Ara-A and tubercidin.

124. A method for reducing the resistance of an MLS-susceptible bacterium to an MLS antibiotic selected from the group consisting of a macrolide, lincosamide and streptogramin B antibiotic, the method comprising contacting said MLS-susceptible bacterium with an effective amount of said MLS antibiotic and an amount of a methylation inhibitor effective to inhibit RNA methylation or maturation in said MLS-susceptible bacterium.

125. A method for killing an MLS-susceptible bacterium, comprising contacting said MLS-susceptible bacterium with an effective amount of an MLS antibiotic selected from the group consisting of a macrolide, lincosamide and streptogramin B antibiotic, in combination with an amount of a methylation inhibitor effective to inhibit RNA methylation or maturation in said bacterium.

126. A method for treating an MLS bacterial infection, comprising administering to an animal with an MLS-susceptible bacterial infection a therapeutically effective amount of an MLS antibiotic selected from the group consisting of a macrolide, lincosamide and streptogramin B antibiotic, in combination with an amount of a methylation inhibitor effective to inhibit RNA methylation or maturation in said bacterium.

127. The method of any one of claims 124, 125 or 126, wherein said MLS antibiotic is a macrolide antibiotic.

128. The method of claim 127, wherein said MLS antibiotic is erythromycin.

129. The method of any one of claims 124, 125 or 126, wherein said MLS antibiotic is azithromycin, clarithromycin lincomycin or clindamycin.

130. The method of any one of claims 124, 125 or 126, wherein said methylation inhibitor inhibits S-adenosylhomocysteinehydrolase (SAHH).

131. The method of any one of claims 124, 125 or 126, wherein said methylation inhibitor is SAH, an SAH analogue, homocysteine, an adenine derivative, a SAM analogue, sinefungin, a sinefungin analogue, polyinosinate, nicotinamide, adenosine, an adenosine analogue, NPA, an NPA analogue, tubercidin, cycloleucine, a cycloleucine analogue, a methionine analogue, AMPNPP, buthionine sulfoximine, 7,8-dihydrofolate, a-aminomethylglutarate, SAPH-3, $N_2O$, conformycin, a conformycin isomer, methotrexate (MTX), aminopterin, trimethoprim, α-methylornithine, 1,3-diaminopropan-2-ol, DFMO, DFMA, 5-azacitidine, cordycepin, toyocamycin, AMA, MHZPA, MAOEA, AbeAdo, AdoMac, MGBG, CGP-39'937 or CGP-33'829.

132. The method of claim 131, wherein said methylation inhibitor is 3-deazaneplanocin A ($c^3$-NpcA).

\* \* \* \* \*